(12) United States Patent
Henderson et al.

(10) Patent No.: US 9,551,021 B2
(45) Date of Patent: Jan. 24, 2017

(54) METHODS AND COMPOSITIONS FOR DETECTING PATHOGENIC BACTERIA

(71) Applicant: Washington University, St. Louis, MO (US)

(72) Inventors: Jeffrey P. Henderson, St. Louis, MO (US); Chia Hung, St. Louis, MO (US); Kaveri Chaturvedi, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 14/689,868

(22) Filed: Apr. 17, 2015

(65) Prior Publication Data
US 2015/0218614 A1 Aug. 6, 2015

Related U.S. Application Data

(63) Continuation-in-part of application No. 13/897,869, filed on May 20, 2013, now Pat. No. 9,017,953.

(60) Provisional application No. 61/648,939, filed on May 18, 2012.

(51) Int. Cl.
| | | |
|---|---|---|
| *A61K 39/00* | (2006.01) | |
| *C07K 14/24* | (2006.01) | |
| *C12Q 1/00* | (2006.01) | |
| *C12Q 1/10* | (2006.01) | |
| *G01N 33/569* | (2006.01) | |

(52) U.S. Cl.
CPC .......... *C12Q 1/10* (2013.01); *G01N 33/56916* (2013.01); *G01N 2333/245* (2013.01); *G01N 2800/52* (2013.01)

(58) Field of Classification Search
None
See application file for complete search history.

(56) References Cited

PUBLICATIONS

Miller et al. 2001 (Yersiniabactin Synthetase: Probing the Recognition of Carrier Protein Domains by the Catalytic Heterocyclization Domains, Cy1 and Cy2, in the chain-initiating HMWP2 Subunit; Biochemistry, 40: 5313-5321).*
McLoughlin et al. 2005 (Monitoring Multiple Active Sites on Thiotemplate Enzymes in Parallel: A Molecular Movie of Yersiniabactin Bioassembly; JACS 127: 14984-14985).*
Hancock et al. 2008 (The ferric yersiniabactin uptake receptor FyuA is required for efficient biofilm formation by urinary tract infectious *Escherichia coli* in human urine).*
Bautzova et al., "Multiparticulate systems containing 5-aminosalicylic acid for the treatment of inflammatory bowel disease", Drug Development and Industrial Pharmacy, 2011, pp. 1100-1109, vol. 37, No. 9.
Bertolini et al., "A New Rational Hypothesis for the Pharmacophore of the Active Metabolite of Leflunomide, a Potent Immunosuppressive Drug", Journal of Medicinal Chemistry, 1997, pp. 2011-2016, vol. 40, No. 13.
Bodor, "Novel Approaches to the Design of Safer Drugs: Soft Drugs and Site-Specific Chemical Delivery Systems", Advances in Drug Research, 1984, pp. 255-331, vol. 13.
Bultreys et al., Yersiniabactin Production by Pseudomonas syringae and *Escherichia coli* and Description of a Second Yersiniabactin Locus Evolutionary Group, Appl. Environ, Microbiology, 2006, pp. 3814-3825, vol. 72, No. 6.
Brumbaugh et al., "Preventing urinary tract infection: progress toward an effective *Escherichia coli* vaccine," Expert Rev Vaccines, 2012, pp. 663-676, vol. 11, No. 6.
Cai et al., "The Role of Asymptomatic Bacteriuria in Young Women With Recurrent Urinary Tract Infections: To Treat or Not to Treat?," Asymptomatic Bacteria and UTI, 2012, pp. 771-777, vol. 55.
Chaturvedi et al., "The siderophore yersiniabactin binds copper to protect pathogens during infection," Nat Chem Biol., 2012, pp. 731-736, vol. 8, No. 8.
Clatworthy et al., "Targeting virulence: a new paradigm for antimicrobial therapy," Nature Chemical Biology, 2007, pp. 541-548, vol. 3, No. 9.
Clermont et al., "Rapid and Simple Determination of the *Escherichia coli* Phylogenetic Group," Applied and Environmental Microbiology, 2000, pp. 4555-4558, vol. 66, No. 10.
Cusumano et al., "Treatment and Prevention of Urinary Tract Infection with Orally Active FimH Inhibitors," Sci Transl Med., 2011, pp. 1-22, vol. 3, No. 109.
Chaturvedi et al., "Pathogenic adaptations to host-derived antibacterial copper," Frontiers in Cellular and Infection Microbiology, 2014, pp. 1-12, vol. 4, No. 3.
Engelhart et al., "Synthesis of Chromone, Quinolone, and Benzoxazinone Sulfonamide Nucleosides as Conformationally Constrained Inhibitors of Adenylating Enzymes Required for Siderophore Biosynthesis," J Org Chem., 2013, pp. 7470-7481, vol. 78, vol. 15.
Fischbach et al., "Antibiotics for Emerging Pathogens," Science, 2009, pp. 1089-1093, vol. 325, No. 5944.
Gorska et al., "Siderophore-drug complexes: potential medicinal applications of the 'Trojan horse' strategy," Trends in Pharmacological Sciences, 2014, vol. 35, No. 9.
Henderson et al., "Quantitative Metabolomics Reveals an Epigenetic Blueprint for Iron Acquisition in Uropathogenic *Escherichia coli*", PLoS Pathogens, 2009, e1000305, 11 pgs., vol. 5, No. 2.
Johnson et al., "Extended Virulence Genotypes and Phylogenetic Background of *Escherichia coli* Isolates from Patients with Cystitis, Pyelonephritis, or Prostatitis," The Journal of Infectious Diseases, 2005, pp. 46-50, vol. 191.
Lee et al., "New Synthetic Cluster Ligands for Galactose/N-Acetylgalactosamine-Specific Lectin of Mammalian Liver", Biochemistry, 1984, pp. 4255-4261, vol. 23, No. 18.
Lichtenstein et al. "Review article: 5-aminosalicylate formulations for the treatment of ulcerative colitis—methods of comparing release rates and delivery of 5-aminosalicylate to the colonic mucosa", Alimentary Pharmacology & Therapeutics, 2008, pp. 663-673, vol. 28.

(Continued)

*Primary Examiner* — Gary Nickol
*Assistant Examiner* — Mary Lyons
(74) *Attorney, Agent, or Firm* — Polsinelli PC

(57) ABSTRACT

The present invention encompasses methods and compositions for detecting pathogenic bacteria. Additionally, the present invention encompasses methods and compositions for catalyzing the dismutation of superoxide radicals. Further, the present invention encompasses methods for determining the antibiotic susceptibility of pathogenic bacteria.

6 Claims, 61 Drawing Sheets
(25 of 61 Drawing Sheet(s) Filed in Color)

(56) References Cited

PUBLICATIONS

Litwin et al., "Outcomes/Epidemiology/Socioeconomics/ Urologic Diseases in America Project: Analytical Methods and Principal Findings," The Journal of Urology, 2005, pp. 933-937, vol. 173.

Lukacik et al., "Structural engineering of a phage lysin that targets Gram-negative pathogens," PNAS, 2012, pp. 9857-9862, vol. 109, No. 25.

Marschall et al., "Both Host and Pathogen Factors Predispose to *Escherichia coli* Urinary-Source Bacteremia in Hospitalized Patients", Clinical Infectious Diseases, 2012, pp. 1692-1698, vol. 54, No. 12.

Madeira et al., Biclustering Algorithms for Biological Data Analysis: A Survey, IEEE Transactions on Computational Biology and Bioinformatics, 2004, vol. 1, No. 1.

Marschall et al., "Both Host and Pathogen Factors Predispose to *Escherichia coli* Urinary-Source Bacteremia in Hospitalized Patients," Clinical Infectious Diseases, 2012, pp. 1692-1698, vol. 54.

Nagachar et al., "Knocking out salicylate biosynthesis genes in *Mycobacterium smegmatis* induces hypersensitivity to p-aminosalicylate (PAS)", FEMS Microbiol Lett., 2010, pp. 193-199, vol. 311, No. 2.

Nagel et al., "Ninth Annual NIH Interdisciplinary Womens Health Research Symposium," Journal of Women's Health, 2012, pp. 985-1013, vol. 21.

Notice of Allowance and Fee(S) Due, related to U.S. Appl. No. 13/897,869, dated Aug. 12, 2014, 11 pages.

Office Action, U.S. Appl. No. 13/897,869 dated Jun. 24, 2014, 25 pages.

Olesen et al., "Three-Decade Epidemiological Analysis of *Escherichia coli* O15:K52:H1," Journal of Clinical Microbiology, 2009, pp. 1857-1862, vol. 47, No. 6.

Olesen et al., "Temporal Trends in Antimicrobial Resistance and Virulence-Associated Traits within the *Escherichia coil* Sequence Type 131 Clonal Group and Its H30 and H30-Rx Subclones, 1968 to 2012," Antimicrobial Agents and Chemotherapy, 2014, pp. 6886-6895, vol. 58, No. 11.

Platell et al., "Prominence of an O75 Clonal Group (Clonal Complex 14) among Non-ST131 Fluoroquinolone-Resistant *Escherichia coli* Causing Extraintestinal Infections in Humans and Dogs in Australia," Antimicrobial Agents and Chemotherapy, 2012, pp. 3898-3904, vol. 56, No. 7.

Pramanik et al., "Albomycin is an effective antibiotic , as exemplified with Yersinia enterocolitica and *Streptococcus pneumoniae*," International Journal of Medical Microbiology, 2007, pp. 459-469, vol. 297.

Ratledge et al., "Inhibition of Mycobactin Formation in *Mycobacterium smegmatis* by p-Aminosalicylate. A New Proposal for the Mode of Action of p-Aminosalicylate", American Review of Respiratory Disease, 1972, pp. 774-776, vol. 106, No. 5.

Roberts et al., "Total (Bio)Synthesis: Strategies of Nature and of Chemists", Top Curr Chem., 2010, pp. 149-203, vol. 297.

Ronald et al., "Urinary tract infection in adults: research priorities and strategies," International Journal of Antimicrobial Agents, 2001, pp. 343-348, vol. 17.

Shan et al., "Prodrug Strategies Based on Intramolecular Cyclization Reactions", Journal of Pharmaceutical Sciences, 1997, pp. 765-767, vol. 86, No. 7.

Simplicio et al., "Prodrugs for Amines", Molecules, 2008, pp. 519-547, vol. 13.

Snyder et al., "Transcriptome of Uropathogenic *Escherichia coli* during Urinary Tract Infection", Infection and Immunity, 2004, pp. 6373-6381, vol. 72, No. 11.

Silverman et al., "From Physiology to Pharmacy: Developments in the Pathogenesis and Treatment of Recurrent Urinary Tract Infections," Curr Urol Rep., 2013, pp. 448-456, vol. 14, No. 5.

Wiles et al., "Origins and Virulence Mechanisms of Uropathogenic *Escherichia coli*," Exp Mol Pathol., 2008, pp. 11-19, vol. 85, No. 1.

Yue et al., "Toleration and Absorption of Sodium Para-Aminosalicylate and Para-Aminosalicylic Acid (Neopasalate)*, Comparison with Other Forms of Para-Aminosalicylic Acid," Diseases of the Chest, 1966, pp. 165-174, vol. 49, No. 2.

Zheng et al., "Enterobactin-Mediated Delivery of B-Lactam Antibiotics Enhances Antibacterial Activity against Pathogenic *Escherichia coil*," Journal of the American Chemical Society, 2014, pp. 9677-9691, vol. 136.

\* cited by examiner

HPTT
*m/z*=307

Yersiniabactin (Ybt)

METHODS AND COMPOSITIONS FOR DETECTING PATHOGENIC BACTERIA

CROSS REFERENCE TO RELATED APPLICATIONS

This application is a continuation-in-part of U.S. application Ser. No. 13/897,869, filed May 20, 2013, which claims priority to U.S. provisional application No. 61/648,939, filed May 18, 2012, each of which is hereby incorporated by reference in its entirety.

GOVERNMENTAL RIGHTS

This invention was made with government support under NIH grant numbers K12 HD001459-09, AI 07172-24, P30 HL101263-01, P50 DK64540, U01 DK082315, and UL1 RR024992. The government has certain rights in the invention.

FIELD OF THE INVENTION

The present invention encompasses methods and compositions for detecting pathogenic bacteria. Additionally, the present invention encompasses methods and compositions for catalyzing the dismutation of superoxide radicals. Further, the present invention encompasses methods for determining the antibiotic susceptibility of bacteria.

BACKGROUND OF THE INVENTION

Urinary tract infection (UTI) caused by uropathogenic *Escherichia coli* (UPEC) is one of the most common infectious diseases in women. The morbidity and economic impact are enormous, with over $2.5 billion spent annually on treatment. Further, recurrent infections are a significant problem despite appropriate antibiotic therapy of the index case. The high rates of recurrence, and the large numbers of women that end up in urology clinics due to their chronic recurrent UTIs highlights the need for a better understanding of the pathogenic mechanisms involved in this disease and the development of new and better therapies. The high frequency of same-strain recurrences supports the notion that a UPEC quiescent intracellular reservoir (QIR) can exist in the affected individual, and persist even after antibiotic therapy and urine cultures become sterile. Current diagnostic schemes for these bacteria are based on culture and do not distinguish between strains with high or low virulence potential.

Therefore, there is a need for an effective biomarker for urinary tract infections that avoids false negative results that occur when culture-based methods are applied during antibiotic therapy or when culture or nucleic acid-based methods are applied to patients in which bacteria are not actively shed into sampled fluids. In addition, there is a need for effective treatments that can cure urinary tract infections and prevent infection by quiescent intracellular reservoirs of pathogenic bacteria that are the source of so many recurrent urinary tract infections.

Further, due to the high incidence of UTI, antibiotic resistance is common. As clinicians struggle with the paucity of mechanistically new antibiotics targeting Gram-negative pathogens and dramatic increases in antibiotic resistance, UTIs are increasingly difficult to manage. As a result, UTIs present a high economic burden marked by increasing healthcare costs. The potential for Gram-negative UTIs to progress to systemic infections motivates aggressive antibiotic use, which drives the selective evolution of antibiotic resistant strains among gut microbiota. Along with concerns of treatment-resistant infections, there is a growing appreciation that current broad-spectrum antibiotic strategies cause detrimental changes to the human microbiome. Thus, there is a need to strategically treat UTI such that if the causative strain is susceptible to a narrower spectrum antibiotic, then that antibiotic is used thereby saving use of broad spectrum antibiotics to only when necessary. Further, strategic treatment of UTI by treating with an antibiotic in which the causative strain is susceptible reduces the likelihood of treatment failures thereby reducing the incidence of developing a systemic infection due to spread of the resistant organism.

SUMMARY OF THE INVENTION

One aspect of the present invention encompasses a method for detecting the presence of yersiniabactin-expressing bacteria in a subject. The method comprises the steps of: a) obtaining a sample from the subject; b) analyzing the sample, in vitro, for the presence or absence of cupric yersiniabactin, wherein the presence of cupric yersiniabactin is determined by contacting the sample with an antibody specific for cupric yersiniabactin; and c) identifying the presence of yersiniabactin-expressing bacteria in the subject when cupric yersiniabactin is present in the sample.

Another aspect of the present invention encompasses a method for detecting the presence of yersiniabactin-expressing bacteria in a subject. The method comprises the steps of: a) obtaining a sample from the subject; b) analyzing the sample, in vitro, for the presence or absence of hydroxphenyl-thiazolinyl-thaizolinyl (HPTT); and c) identifying the presence of yersiniabactin-expressing bacteria in the subject when HPTT is present in the sample.

Yet another aspect of the present invention encompasses a method for determining the antibiotic susceptibility of pathogenic bacteria in a subject. The method comprises: (a) obtaining a sample for the subject; (b) analyzing the sample, in vitro, for the presence or absence of siderophores selected from the group comprising yersiniabactin, salmochelin and aerobactin; (c) identifying the combination of siderophores present wherein the combination indicates susceptibility according to the following: (i) the presence of yersiniabactin only indicates susceptibility to ciprofloxacin (cipro); (ii) the presence of yersiniabactin+aerobactin indicates resistance to cipro and trimepthoprim-sulfamethoxazole (TMP-SMZ); (iii) the presence of yersiniabactin+salmochelin indicates susceptibility to cipro and TMP-SMZ; (iv) the presence of yersiniabactin+aerobactin+salmochelin indicates susceptibility to cipro; (v) the presence of aerobactin indicates resistance to cipro; and (vi) the absence of yersiniabactin+ aerobactin+salmochelin indicates susceptibility to cipro.

Other aspects and iterations of the invention are described in more detail below.

BRIEF DESCRIPTION OF THE FIGURES

The application file contains at least one photograph executed in color. Copies of this patent application publication with color photographs will be provided by the Office upon request and payment of the necessary fee.

FIG. 1A depicts the triscatecholate siderophore enterobactin and FIG. 1B depicts the siderophore yersiniabactin, characterized by a phenolate moiety and thiazoline rings.

(FIG. 2A) A common neutral loss of 187 amu was evident in MS/MS product ion spectra of ferric-yersiniabactin (Fe(III)-Ybt) at m/z 535, aluminum-yersiniabactin (Al(III)-Ybt) at m/z 506, and gallium-yersiniabactin (Ga(III)-Ybt) at m/z 548. (FIG. 2B) This 187 amu neutral loss is consistent with the proposed rearrangement and loss of the third, carboxylated thiazoline ring. A constant neutral loss (CNL) scan based on this conserved fragmentation pathway was used as a metallomic screen to identify physiologic yersiniabactin binding partners. Representative constant neutral loss chromatograms of urine samples in the presence (FIG. 2C) and absence (FIG. 2D) of purified apo-yersiniabactin are shown. The combination of apo-yersiniabactin and urine results in a prominent new peak (peak 1). Peaks corresponding to ferric-yersiniabactin (Fe-Ybt) and internal standard (int. std) are indicated. These results were confirmed in three independent experiments.

(FIG. 3A) MS/MS analysis of the m/z 543 and 545 ions from peak 1 confirms the 187 amu neutral loss and shows comparable fragmentation patterns, consistent with natural $^{63}Cu$ and $^{65}Cu$ isotope abundances. Addition of cupric sulfate to yersiniabactin-containing culture supernatant generated a robust new peak 1 signal, which was collected for analysis. (FIG. 3B) High resolution positive ion ESI mass spectrum is consistent with the empiric formula for singly charged Cu(II)-Ybt and demonstrates the prominent M+2 ion expected from $^{65}Cu$. (FIG. 3C) Competitive binding experiments were conducted by titration of cupric sulfate into solutions containing a fixed concentration of 0.01 M ferric chloride and 0.01 M apo-yersiniabactin. Data indicate competitive binding between cupric and ferric ion for the ligand. Cu(II)-Ybt/Fe(III)-Ybt ratios were quantified by generating a calibration curve of known ratios of each metal-yersiniabactin complex, and analyzing the samples by LC-MS. (FIG. 3D) Cu(II)-Ybt complexes are stable and bound copper is not displaced by ferric ions over a period of 24 hours. Cu(II)-Ybt is expressed as its ratio to trace Fe(III)-Ybt impurity in apo-Ybt.

(FIG. 4C) In the infected urine samples, the median Cu(II)-Ybt:Fe(III)-Ybt ratio is 15.3, indicating that yersiniabactin preferentially binds copper (II) in vivo.

(FIG. 5A) A scanning constant neutral loss spectrum reveals the spectrum for Cu(II)-Ybt at its expected retention time. The expected copper isotope peaks at m/z 543 for $^{63}Cu$ and m/z 545 for 65Cu peak are indicated. (FIG. 5B) Urinary Cu(II)-Ybt was detected in 13 of 15 patients infected with a yersiniabactin-expressing pathogen and in none of the patients with yersiniabactin non-expressors. Cu(II)-Ybt levels are reported as a fraction of the corresponding $^{13}C$ internal standard peak height. (FIG. 5C) In urine samples with detectable yersiniabactin complexes, the median Cu(II)-Ybt (m/z 543) to Fe(III)-Ybt (m/z 535) ratio is 2.941, indicating preferential in vivo copper (II) binding.

(FIG. 6A) Urinary strains demonstrate greater resistance to copper toxicity that coexisting rectal strains. For each patient, the number of viable bacteria from the non-urinary source was subtracted from the number of viable coincident urinary strains to yield a difference. In the four patients from whom multiple coincident urinary and non-urinary strains were recovered, the mean difference in siderophore production is reported. The median value of these differences was $2.11 \times 10^7$ CFU/mL, with a range of $-5.4 \times 10^3$ to $1.66 \times 10^8$. (FIG. 6B) Yersiniabactin-expressors were more resistant to copper toxicity than non-expressors (p<0.0013). These results were confirmed in three independent experiments. (FIG. 6C) Yersiniabactin-expressor (UT189) and non-expressor (UTI89ΔybtS) cultures treated with 0-25 M copper (II) sulfate revealed an average of ten-fold survival advantage for the yersiniabactin expressor (p=0.0044, t-test). (FIG. 6D) Purified apo-yersiniabactin or Cu(II)-Ybt was added in 1.5-fold molar excess over 10 M copper (II) sulfate to yersiniabactin-deficient (UTI89ΔybtS) culture. Samples containing copper alone demonstrated a >3 log CFU/mL decrease in viability. Apo-yersiniabactin (apo-Ybt) addition restores growth to untreated wild type levels (p=ns). This cytoprotective effect is unique to apo-yersiniabactin, and is not observed upon addition of pre-formed Cu(II)-Ybt. These results were confirmed in three independent experiments.

(FIG. 7A) Growth of wild type (UT189), yersiniabactin (ΔybtS), catecholate siderophore (ΔentB), or total siderophore (ΔentBΔybtS) expression mutants in the presence of copper was determined. Results were consistent with copper-dependent cytoprotective effect for yersiniabactin and cytotoxic effect for catecholate siderophores. (FIG. 7B) Exogenous addition of 20 µM of the siderophore enterobactin, or its catecholate moiety 2,3-dihydroxybenzoate (DHB) enhances copper (II) sulfate toxicity in UT189. (FIG. 7C, FIG. 7D) Apo-yersiniabactin prevents catechol-dependent reduction of copper (II) sulfate to copper (I) in an order-of-addition dependent manner. The complete reaction system consisted of 17.5 M copper(II) sulfate, either 20 µM enterobactin (ent) or its catecholate moiety 2,3-dihydroxybenzoic acid (DHB), 25 M apo-yersiniabactin (Ybt), and 25 µM of the copper(I) indicator bathocuproine sulfonate. Reagents were added in the order indicated and Cu(I)-bathocuproine absorbance was determined 30 min after addition of the last reagent. Results were confirmed in three independent experiments.

(FIG. 8A) Full scan positive ion ESI spectrum at the Cu(II)-Ybt retention time reveals an $[M+H]^+$ peak at m/z 564 and M+2 at m/z 566, consistent with $^{13}C$-substitution of all 21 carbon atoms in yersiniabactin and the copper M+2 isotope. (FIG. 8B) MS/MS of the m/z 564 ion revealed a shifted dominant MS/MS neutral loss of 195 mass units, corresponding to loss of a fragment containing eight carbons.

(FIG. 9A) Full scan positive ion ESI spectrum at the Fe(III)-Ybt retention time reveals an [M+H]+ peak at m/z 539, consistent with introduction of the four nonexchangable deuterons in $d_6$-salicylate. (FIG. 9B) MS/MS of the m/z 539 ion revealed a dominant 187 m/z unit neutral loss, consistent with neutral loss of a fragment from yersiniabactin's unlabeled carboxylic acid terminus.

(FIG. 13A) SOD activity is observed in the 80% methanolic extracts of copper treated UT189 and ΔentB, but not the ΔybtS culture supernatants. This is the fraction associated with yersiniabactin purification. (FIG. 13B) SOD activity is not observed in UT189, ΔentB or ΔybtS culture supernatants, indicating that this enzymatic activity requires the interaction of copper and yersiniabactin. The data are presented as means±SD of three independent experiments.

(FIG. 14A) Percentage inhibition rate of 63.12% is associated with copper (II)-yersiniabactin, but not with apo-yersiniabactin alone. (FIG. 14B) 41.4% inhibition rate is observed with ferric complexes of yersiniabactin. (FIG. 14C) While SOD activity is observed in cupric and ferric complexes of yersiniabactin, this activity is abolished in redox inert gallium complexes. SOD activity is dependent on the redox state of the metal bound to yersiniabactin. (FIG. 14D) A dose-response relationship is observed in the SOD activity associated with purified copper (II)-yersiniabactin complexes. The data are presented as means±SD of five independent experiments.

(FIG. 15A) The superoxide-dismuting activity of both copper (II) complexes with yersiniabactin and with saliyclate, the synthetic precursor of this siderophore, were determined. The percentage inhibition rate associate with copper (II)-salicylate complexes is 61.6%, compared to 65% for copper (II)-yersiniabactin complexes. (FIG. 15B) The superoxide dismutase activity of these complexes was tested in the presence of 1.0 mg/mL bovine serum albumin (BSA) to determine whether this enzymatic activity is retained in a physiologic environment with high concentration of protein. The superoxide dismutase activity associated with copper (II)-salicylate complexes is quenched in the presence of BSA, while this activity is retained in the copper (II) yersiniabactin complexes. This gives a chemical rationale for the complex synthesis of yersiniabactin, instead of relying on a simpler precursor for similar enzymatic activity.

(FIG. 16A) Survival of UT189 one hour post incubation in RAW264.7 cells is indicated. Note that UT189 survival was significantly increased in DPI untreated, superoxide-replete RAW 264.7 cells compared with untreated controls. Copper pretreatment of these cells was additionally necessary to observe preferential survival of wild type UT189. (FIG. 16B) The survival phenotype is not observed for the ybtS deficient mutant, suggesting that yersiniabactin expression predominantly contributes to the survival phenotype observed in UT189. (FIG. 16C) MG1655, an E. coli commensal strain that does not express yersiniabactin, similarly does not respond to copper challenge and is susceptible to the bactericidal activity of RAW264.7 cells under all conditions tested. These results were confirmed in four independent experiments.

(FIG. 18A) Proposed mechanism for loss of 187 amu unit from m/z 543. As previously reported, this is consistent with the rearrangement of the C13-C14 bond and loss of the third, carboxylated thiazoline ring. (FIG. 18B) Yersiniabactin coordinates copper (II) in a square planar configuration, with two sets of electron pairs donated by the phenolate and secondary alcohol oxygens and two from the neutral nitrogen atoms.

(FIG. 22B) In the ybtS knockout culture supplemented with $^{13}$C-salicylate, an ion with a mass charge ratio of 313 eluted at the same time as the 307 ion in a wildtype UT189 culture. This confirmed that the 307 ion has 6 carbons derived from the benzene ring of salicylate (FIG. 22A).

(FIG. 27A) Virulence factor incidence in the 337 clinical isolates is shown. (FIG. 27B) Each virulence factor (VF) was assigned a score of 1. Any virulence score greater than or equal to 1 indicates the presence of one or more VFs, and 0 is the absence of individual genes. Since the presence and absence of all 16 genes were considered, the VF score ranged from 0 to 16. Next, a data matrix was generated to determine each clinical isolate's VF profile. A bimodal distribution of virulence scores was observed among 337 clinical isolates, with local maxima at one and nine virulence factors.

(FIG. 28A) Three VF communities are evident in an empirical heatmap depicting statistically significant positive correlations between VFs. (FIG. 28B) A force-directed layout illustrates connectivities between individual virulence factors (VFs) organized into three VF communities (colors). (FIG. 28C) Hierarchical clustering of VF genes in a polar coordinate dendrogram colored according to community identification. Each VF community contains a distinct siderophore gene (iroN, fyuA, iucD).

(FIG. 29A) Four distinct communities (identified using modularity maximization) describe the CIs in this population. Color scale (dark blue: VF presence=100%, white ≤5%). (FIG. 29B) A force-directed layout illustrates associations between virulence factor (VF) profiles of individual UPEC clinical isolates (CIs). Each node represents a CI and connecting line (edge) lengths are determined to most closely match the connectivity level between the connected CIs (colored by CI community assignment).

(FIG. 30A) Four biclusters describe 82% of the CIs in this population. Siderophore genes are in bold type. Color scale (dark blue: VF presence=100%, white 5%) (FIG. 30B, FIG. 30C) The force-directed layout for clinical isolates overlaid with each CI's bicluster assignments (FIG. 30B) and siderophore genotype (FIG. 30C) illustrates overall similarities between these CI classification approaches and the communities in FIG. 27B.

FIG. 31A, FIG. 31O, FIG. 31G, and FIG. 31J depict the CI communities. FIG. 31B, FIG. 31E, FIG. 31H, and FIG. 31K depict biclusters. FIG. 31C, FIG. 31F, FIG. 31I, and FIG. 31L depict siderophore genotype. Patient sex and antibiotic resistance (bars) in each clinical isolate subgroup relative to total study population (dashed lines) are shown. Subgroup size (#) is indicated in the bottom row. Small subgroups (<6 CI) were omitted for clarity. fyuA+iucD strategists (community 2, BC1+2) exhibit notable sex and ciprofloxacin resistance associations. Statistical significance determined by Fisher's Exact Test is indicated by number of stars (p-values: 0.05, 0.01 & 0.001, respectively, without correction for multiple testing).

(FIG. 32A) $CIP^R$ rates among E. coli at Barnes-Jewish Hospital from 2000-2013. The grey bar corresponds to the collection period for the clinical isolates examined in this study. (FIG. 32B) Most $CIP^R$ urinary E. coli isolates are fyuA+iucD strategists while (FIG. 32C) all fyuA+iroN strategists are $CIP^S$.

DETAILED DESCRIPTION OF THE INVENTION

Figure 1A:
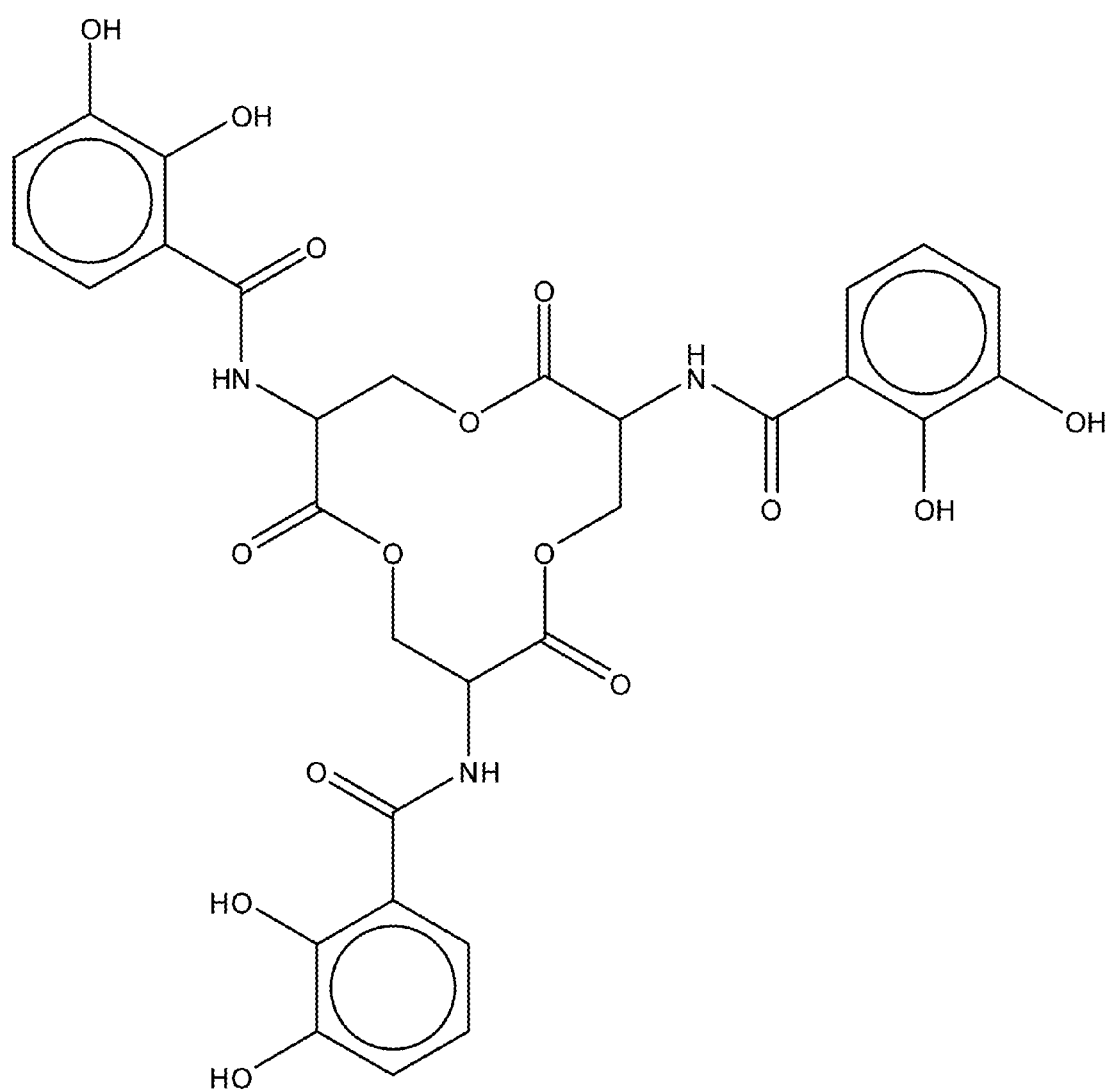
FIG. 1A-B depicts chemical structures of *E. coli* siderophores which are characterized by structural and chemical diversity.

The present invention encompasses the discovery that cupric yersiniabactin is a biomarker for the presence of pathogenic bacteria in a subject. Cupric yersiniabactin is formed when pathogenic bacteria capable of producing yersiniabactin secrete yersiniabactin in a subject. The yersiniabactin subsequently interacts with copper (II) ions from the subject to form cupric yersiniabactin, a stable, detectable organometallic complex. This discovery has led to methods of detecting the presence of pathogenic bacteria in a subject, and methods of determining if a subject would benefit from a yersiniabactin inhibitor. Further, it was discovered that a product produced during the biosynthesis of yersiniabactin, HPTT, may also be used to detect pathogenic bacteria. HPTT was found to be produced at levels roughly equal to yersiniabactin. This is entirely surprising as HPTT is only produced as a transient intermediate in the biosynthetic pathway of yersiniabactin, and according to theory should be covalently attached to HMWP2. It was wholly unexpected that HPTT may be used to detect the presence of pathogenic bacteria given that is known in the art to be a transient intermediate that is covalently attached to a protein involved in the biosynthesis of yersiniabactin.

Additionally, the invention encompasses a compound having superoxide dismutase activity. Advantageously, such a compound may be used to catalyze the dismutation of one or more superoxide radicals.

Further, the invention encompasses a method to determine the susceptibility of pathogenic bacteria to antibiotics based on specific combinations of virulence factors. Such a determination allows more efficient treatment of a subject and reduces the likelihood of treatment failures.

I. Methods of Detecting Pathogenic Bacteria

In one aspect, the present invention encompasses a method for detecting the presence of pathogenic bacteria in a subject. In exemplary embodiments, a method of the invention may be used to detect pathogenic bacteria in the urinary tract of a subject. Advantageously, a method of the invention avoids false negative results that occur when culture-based methods are applied during antibiotic therapy to determine the presence of pathogenic bacteria or when culture or nucleic acid-based methods are applied to subjects in which bacteria are not actively shed into sampled fluids. Generally speaking, the method comprises analyzing a sample for the presence or absence of cupric yersiniabactin or product thereof, such that the presence of cupric yersiniabactin or a product thereof in the sample indicates the presence of pathogenic bacteria in the subject.

Furthermore, pathogenic bacteria that cause symptomatic urinary tract infection (UTI) and pathogenic bacteria that cause UTIs most likely to progress to bacteremia and sepsis both secrete yersiniabactin. Thus, cupric yersiniabactin or a product thereof may identify not only the presence of pathogenic bacteria but may also identify patients at higher risk of progression to more severe disease.

Figure 1B:
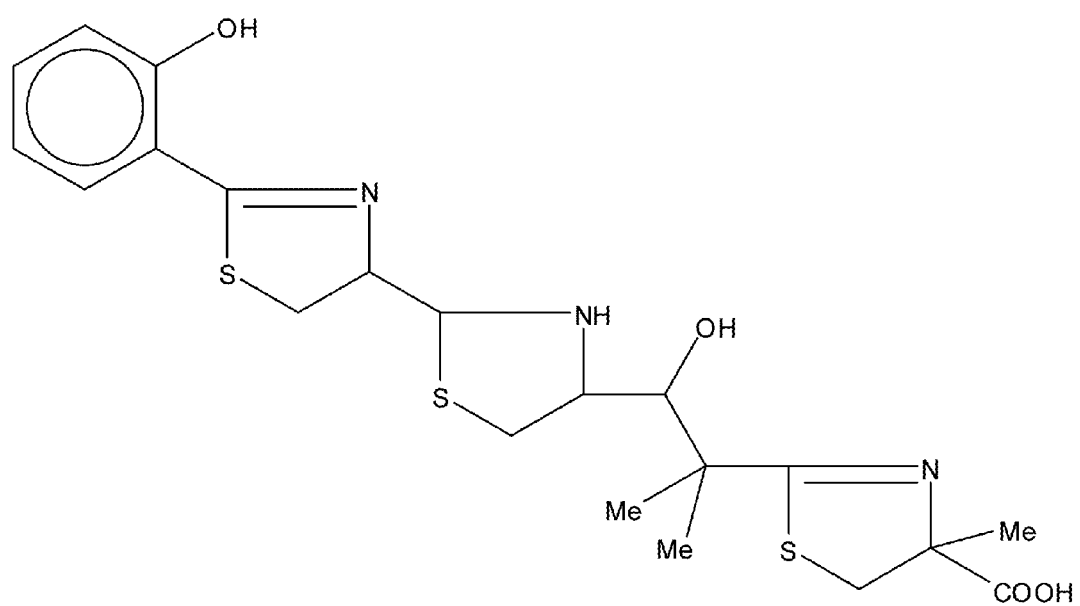
Figure 20A:
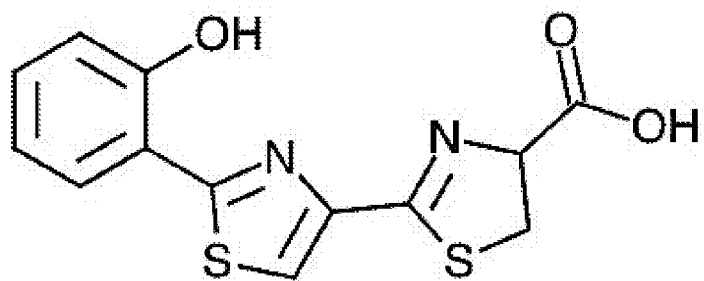
FIG. 20A-B depicts chemical structures of HPTT (FIG. 20A) and yersiniabactin (FIG. 20B).
Figure 24A:
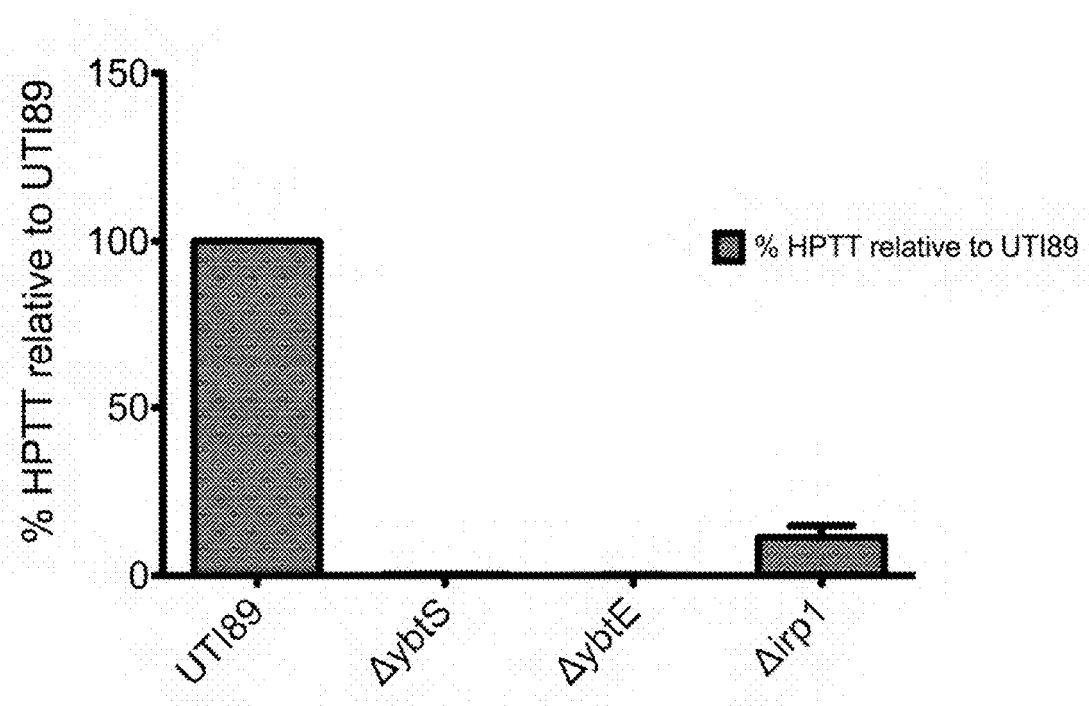
FIG. 24A depicts a graph showing that HPTT is produced in wild type UT189 but not in ybtS and ybtE mutant UT189 suggesting that HPTT is a product of the Ybt biosynthetic machinery.
Figure 24B:
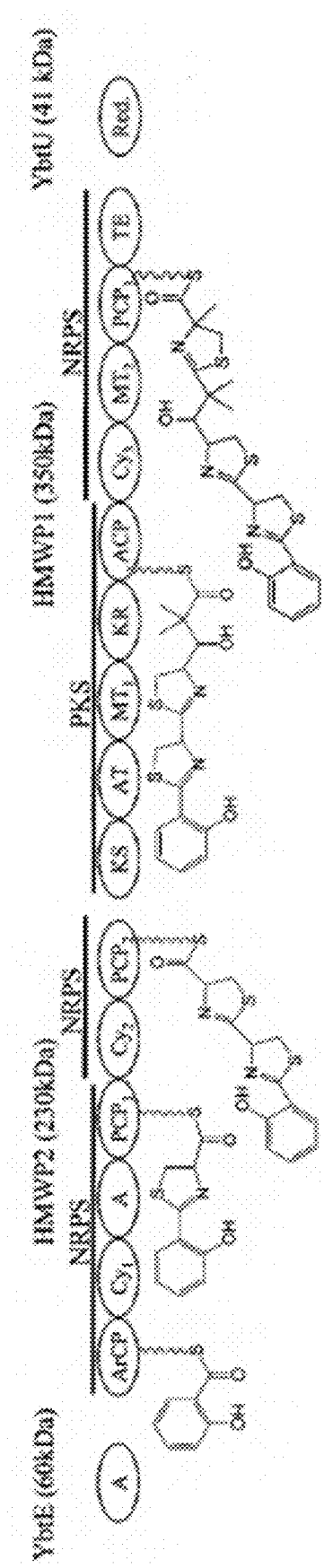
FIG. 24B depicts a diagram showing the biosynthetic pathway of yersiniabactin.

Yersiniabactin (Ybt) is a chemical compound comprising a four ring structure, as illustrated in FIG. 1B. Ybt synthesis occurs by a mixed nonribosomal peptide synthetase (NRPS)/polyketide synthase (PKS) mechanism. Several enzymes, most notably the HMWP2-HMWP1 complex, assemble salicylate, three cysteines, a malonyl linker group and three methyl groups into a four-ring structure made of salicylate, one thiazolidine, and two thiazoline rings with a malonyl linker between the thiazoline and the thiazolidine. YbtD, a phosphopantetheinyl transferase, adds phosphopantetheine tethers to the cysteine, salicylate and malonyl groups to HMWP1 and HMWP2. YbtS synthesizes salicylate from chorismate, which is then adenylated by YbtE and transferred to the HMWP2-HMWP1 assembly complex. HMWP2, which consists of two multidomain NRPS modules, accepts the activated salicylate unit through a carrier protein, then cyclizes and condenses two cysteines to form two thiazoline rings. A malonyl linker is added by the PKS portion of HMWP1, and YbtU reduces the second thiazoline ring to thiazolidine before cyclization and condensation of the final thiazoline ring on HMWP1's NRPs domain. YbtT thioesterase may serve some editing function to remove abnormal molecules from the enzyme complex, and a thioesterase domain of HMWP1 releases the completed siderophore from the enzyme complex. A schematic of the biosynthesis of yersiniabactin is depicted in FIG. 24B. As used herein, a "product thereof" when referring to yersiniabactin may include any of the products produced during the biosynthesis of yersiniabactin. In a specific embodiment, the product thereof is HPTT, as illustrated in FIG. 20A.

Yersiniabactin, while named for being produced by pathogenic *Yersinia* species, is also produced by a number of other pathogenic members of the family Enterobacteriaceae. For instance, yersiniabactin may also be produced by uropathogenic bacteria capable of causing urinary tract infections or *Klebsiella* strains capable of causing pneumonia. In some embodiments, the invention provides a method for detecting the presence of *Klebsiella* strains capable of causing pneumonia in a subject. In other embodiments, the invention provides a method for detecting the presence of *Yersinia* species capable of causing plague in a subject.

In still other embodiments, the invention provides a method for detecting the presence of uropathogenic bacteria capable of causing urinary tract infections in a subject. Non limiting examples of uropathogenic bacteria capable of causing urinary tract infections may include uropathogenic *Escherichia coli* (UPEC) and uropathogenic *Klebsiella* species. In some embodiments, the invention provides a method for detecting the presence of uropathogenic *Klebsiella* species. In exemplary embodiments, the invention provides a method for detecting the presence of uropathogenic *Escherichia coli*.

(a) Subject

Suitable subjects for a method of the invention may include any subject capable of being infected by a yersiniabactin producing pathogen. In some embodiments, the subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an exemplary embodiment, the subject is a human.

In certain embodiments, the subject may be infected by pathogenic bacteria that produce yersiniabactin. For instance, in certain exemplary embodiments, the subject may be suffering from an acute urinary tract infection, or the subject may have a quiescent intracellular reservoir (QIR) after an acute urinary tract infection that persists even after antibiotic therapy and urine cultures become sterile. Alternatively, in some embodiments, the subject may be undergoing antibiotic therapy in which case, bacteria are not shed into sampled fluids for testing and therefore may not detected. In still further embodiments, a subject may suffer from recurrent urinary tract infections.

(b) Sample

A method of the invention comprises obtaining a sample from a subject. Generally speaking, the type of sample obtained is dependent on the type of pathogenic bacteria that is suspected. For instance, if a urinary tract infection is suspected, a urine sample may be collected. Alternatively, if a *Yersinia* infection is suspected, a lymph sample may be collected. A sample may be taken from a subject using any known device or method providing the cupric yersiniabactin or product thereof is not rendered undetectable. Non-limiting examples of devices or methods suitable for taking a sample from a subject include urine sample cups, urethral catheters, swabs, hypodermic needles, thin needle biopsies, hollow needle biopsies, punch biopsies, metabolic cages, and aspiration. A suitable sample may include, but is not limited to, cerebral spinal fluid (CSF), blood plasma, blood serum, urine, saliva, perspiration, lymph, lung lavage fluid, and tears.

In a preferred embodiment, the sample is urine. Methods of collecting a urine sample are known in the art. In essence, urine may be collected midstream into a sterile urine sample cup. The urine sample may be treated for further analysis by adding protease inhibitors and centrifugation to remove cellular material. In addition, the urine sample may be frozen for later analysis.

(c) Analyzing a Sample

A method of the invention comprises analyzing a sample for the presence or absence of cupric yersiniabactin or a product thereof. Suitable methods for the detection of an organometallic compound such as cupric yersiniabactin or product thereof are known in the art, and can and will vary depending upon the nature of the sample.

Methods of detecting cupric yersiniabactin or a product thereof may be indirect or direct. Indirect detection may comprise separating yersiniabactin or a product thereof from other components in the sample, or concentrating yersiniabactin or a product thereof in the sample, followed by detection of cupric yersiniabactin or a product thereof in the purified or concentrated yersiniabactin sample. The yersiniabactin or product thereof may be detected in the apo (unbound form) or in the bound form (i.e. bound to metallic ions such as cupric or ferric ions). The presence of cupric ions in the purified yersiniabactin sample may signify the presence of cupric yersiniabactin or a product thereof bound to copper. Additionally, the presence of ferric ions in the purified yersiniabactin sample may signify the presence of ferric yersiniabactin or a product thereof bound to iron.

In preferred embodiments, cupric yersiniabactin or a product thereof is detected directly by detecting the presence of an organometallic compound. In other embodiments, yersiniabactin is detected indirectly by detecting the presence of a product thereof, specifically HPTT, either bound or unbound to a metallic ion. For instance an epitope binding agent such as an antibody, aptamer, or other molecular beacon that recognizes cupric yersiniabactin or a product thereof of may be used to detect yersiniabactin in the sample as described in more detail below. In an exemplary embodiment, an antibody is used to detect the presence of cupric yersiniabactin. In other embodiments, an antibody is used to detect products from the biosynthesis of yersiniabactin. In a specific embodiment, an antibody is used to detect HPTT. Other non-limiting examples of methods that may be used to detect cupric yersiniabactin or a product thereof in a sample may include enzyme-coupled spectrophotometric assays, HPLC, electrophoresis, and mass spectrometry.

In one embodiment, cupric yersiniabactin or a product thereof is detected using mass spectrometry. In particular, techniques linking a chromatographic step with a mass spectrometry step may be used. Generally speaking, the presence of cupric yersiniabactin or a product thereof may be determined utilizing liquid chromatography followed by mass spectrometry.

In some embodiments, the liquid chromatography is high performance liquid chromatography (HPLC). Non-limiting examples of HPLC may include partition chromatography, normal phase chromatography, displacement chromatography, reverse phase chromatography, size exclusion chromatography, ion exchange chromatography, bioaffinity chromatography, aqueous normal phase chromatography or ultrafast liquid chromatography. In one embodiment, the liquid chromatography may be ultrafast liquid chromatography.

In some embodiments, the mass spectrometry may be constant neutral loss mass spectrometry. In other embodiments, the mass spectrometry may be tandem mass spectrometry (MS/MS). In a different embodiment, the mass spectrometry may be matrix-assisted laser desorption/ionization (MALDI). In a specific embodiment, the mass spectrometry may be electrospray ionization mass spectrometry (ESI-MS).

In an exemplary embodiment, the method comprises liquid chromatography followed by tandem mass spectrometry. In a particularly exemplary embodiment, the method comprises liquid chromatography followed by tandem mass spectrometry as described in the examples. In another exemplary embodiment, the method comprises liquid chromatography followed by constant neutral loss mass spectrometry. In a particularly exemplary embodiment, the method comprises liquid chromatography followed by constant neutral loss mass spectrometry as described in the examples. In still another exemplary embodiment, the method comprises liquid chromatography followed by electrospray ionization mass spectrometry (ESI-MS). In certain embodiments, following mass spectrometry, detection of a peak with a mass-to-charge (m/z) ratio of about 543 indicates the presence of cupric yersiniabactin. In other embodiments, following mass spectrometry, detection of a peak with a mass-to-charge (m/z) ratio of about 307 indicates the presence of HPTT.

In each of the above embodiments, the liquid chromatography followed by mass spectrometry may be used to determine the presence of cupric yersiniabactin or a product thereof in a sample, or the liquid chromatography followed by mass spectrometry may be used to determine the presence and quantity of cupric yersiniabactin or a product thereof in a sample. In preferred embodiments, the liquid chromatography followed by mass spectrometry may be used to determine the presence of cupric yersiniabactin or a product thereof in a sample.

In some embodiments, an epitope binding agent that recognizes cupric yersiniabactin or a product thereof of may be used to detect cupric yersiniabactin in the sample. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to cupric yersiniabactin or a product thereof. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in its binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of assessing the presence or an amount of cupric yersiniabactin or product thereof comprises contacting a sample comprising cupric yersiniabactin or product thereof with an epitope binding agent specific for cupric yersiniabactin or product thereof under conditions effective to allow for formation of a complex between the epitope binding agent and cupric yersiniabactin or product thereof. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-yersiniabactin or product thereof complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, Ni2+, Flag tags, myc tags, heavy metals, and enzymes (including alkaline phosphatase, peroxidase, and luciferase). Methods of detecting an epitope binding agent-yersiniabactin or product thereof complex based on the detection of a label or marker are well known in the art.

In some embodiments, an epitope binding agent-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an epitope binding agent, such as an antibody. Unbound analyte is washed away and the bound analyte is measured. In an alternative embodiment of a competitive immunoassay, an unlabeled analyte in a sample displaces labeled epitope binding agent, such as an antibody, from immobilized analyte. The amount of displaced antibody is measured as an indication of the amount of analyte in the sample. In a non-competitive immunoassay, the epitope binding agent, such as the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In different embodiments, the epitope binding agent-based method is immunohistochemistry (IHC). In alternative embodiments, the epitope binding agent-based method is an array. In different embodiments, the epitope binding agent-based method is a lateral flow assay. A lateral flow assay may be a device intended to detect the presence (or absence) of a target analyte in sample.

II. Antibacterial Therapeutic

In one aspect, the present invention provides a method of treating or preventing infection by pathogenic bacteria capable of producing yersiniabactin. It was discovered that cupric yersiniabactin or a product thereof is associated with virulence in pathogenic bacteria that produce yersiniabactin. For instance, bacterial strains that produce yersiniabactin cause recurring or persistent urinary infections and are most likely to progress to bacteremia and sepsis. As described in the examples, cupric yersiniabactin allows the bacteria to evade the host immune responses by sequestering copper (II) originating from the host, which would otherwise be toxic to the bacteria.

Additionally, it was discovered that para-aminosalicylic acid (PAS) selectively inhibits yersiniabactin biosynthesis without inhibiting growth of the bacterium. Therefore, PAS may be used as a therapeutic or preventive treatment for diseases caused by infections with bacteria that produce yersiniabactin. In preferred embodiments, the method of treating or preventing infection by pathogenic bacteria capable of producing yersiniabactin comprises inhibiting the production of yersiniabactin by administering PAS to the subject.

In certain embodiments, PAS may be administered orally, by inhalation spray, pulmonary, intranasally, rectally, buccally, subcutaneously, intramuscularly, intrasternally intravenously, intravaginally, intrauterinely, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices.

Solid dosage forms for oral administration may include capsules, tablets, pills, powders, and granules. In such solid dosage forms, PAS may be combined with one or more adjuvants appropriate to the indicated route of administration. If administered per oral solid, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings. Tablets or capsules may be coated or otherwise compounded to provide a dosage form affording the advantage of prolonged action. For example, the tablet or capsule may comprise an inner dosage and an outer dosage component, the latter being in the form of an envelope over the former. The two components may be separated by an enteric layer which serves to resist disintegration in the stomach and permit the inner component to pass intact into the duodenum or to be delayed in release. A variety of materials may be used for such enteric layers or coatings, such materials including a number of polymeric acids and mixtures of polymeric acids with such materials as shellac, cetyl alcohol, and cellulose acetate as are known in the art.

Liquid dosage forms for oral administration may include aqueous solutions, suitably flavored syrups, oil suspensions and flavored emulsions with edible oils such as cottonseed oil, sesame oil, coconut oil, or peanut oil as well as elixirs and similar pharmaceutical vehicles. Liquid dosage forms for oral administration may also include pharmaceutically acceptable emulsions, solutions, suspensions, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally or intrathecally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above may also useful.

Other methods of formulating a pharmaceutical composition comprise PAS may be discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Pharmaceutical compositions of the invention comprising PAS may also include pharmaceutically acceptable salts, multimeric forms, prodrugs, active metabolites, precursors and salts of such metabolites.

The term "pharmaceutically acceptable salts" refers to salt forms that are pharmacologically acceptable and substantially non-toxic to the subject being treated with PAS. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multi mer" refers to multivalent or multimeric forms of active forms of PAS. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multi mer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties may include molecular supports comprising a multiplicity of functional groups that can be reacted with functional groups associated with the active compounds of the invention. A variety of carrier moieties may be used to build highly active multimers, including proteins such as BSA (bovine serum albumin) or peptides such as pentapeptides, decapeptides, pentadecapeptides, and the like, as well as non-biological compounds selected for their beneficial effects on absorbability, transport, and persistence within the target organism.

Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art See, e.g., Bertolini, G. et al., (1997) J. Med. Chem. 40:2011 2016; Shan, D. et al., J. Pharm. Sci., 86(7):765 767; Bagshawe K., (1995) Drug Dev. Res. 34:220 230; Bodor, N., (1984) Advances in Drug Res. 13:224 331; Bundgaard, H., Design of Prodrugs (Elsevier Press, 1985); and Larsen, I. K., Design and Application of Prodrugs, Drug Design and Development (Krogsgaard-Larsen et al., eds., Harwood Academic Publishers, 1991). For instance, the prodrug may be any of the PAS prodrug derivatives known in the art. See, e.g., Bautzová et al., (2011) Drug Dev Ind Pharm. 37:1100-9; Lichtenstein et al., (2008) Aliment Pharmacol Ther. 28:663-73; and Simplicio et al., (2008) Molecules, 13:519-547.

The amount of PAS administered will vary depending upon the subject, the suspected pathogenic bacteria, and the particular mode of administration, and may be determined experimentally. For instance, the amount may be about 100 to 200 mg/kg/day. In some embodiments, the amount of PAS may be about 100, 110, 120, 130, 140, 150, 160, 170, 180, 190, or about 200 mg/kg/day. In other embodiments, the amount of PAS may be about 100, 101, 102, 103, 104, 105, 106, 107, 108, 109, 110, 111, 112, 113, 114, or about 115 mg/kg/day. In other embodiments, the amount of PAS may be about 110, 111, 112, 113, 114, 115, 116, 117, 118, 119, 120, 121, 122, 123, 124, or about 125 mg/kg/day. In yet other embodiments, the amount of PAS may be about 120, 121, 122, 123, 124, 125, 126, 127, 128, 129, 130, 131, 132, 133, 134, or about 135 mg/kg/day. In other embodiments, the amount of PAS may be about 130, 131, 132, 133, 134, 135, 136, 137, 138, 139, 140, 141, 142, 143, 144, or about 145 mg/kg/day. In still other embodiments, the amount of PAS may be about 140, 141, 142, 143, 144, 145, 146, 147, 148, 149, 150, 151, 152, 153, 154, or about 155 mg/kg/day. In additional embodiments, the amount of PAS may be about 150, 151, 152, 153, 154, 155, 156, 157, 158, 159, 160, 161, 162, 163, 164, or about 165 mg/kg/day. In other embodiments, the amount of PAS may be about 160, 161, 162, 163, 164, 165, 166, 167, 168, 169, 170, 171, 172, 173, 174, or about 175 mg/kg/day. In still other embodiments, the amount of PAS may be about 170, 171, 172, 173, 174, 175, 176, 177, 178, 179, 180, 181, 182, 183, 184, or about 185 mg/kg/day. In yet other embodiments, the amount of PAS may be about 180, 181, 182, 183, 184, 185, 186, 187, 188, 189, 190, 191, 192, 193, 194, or about 195 mg/kg/day. In other embodiments, the amount of PAS may be about 190, 191, 192, 193, 194, 195, 196, 197, 198, 199, or about 200 mg/kg/day. In preferred embodiments, the amount of PAS may be about 150 mg/kg/day. PAS may be administered in a single daily dose or divided into multiple daily doses. In exemplary embodiments, the amount of PAS may be about 150 mg/kg/day administered in two or three equally divided doses.

Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

As used in a method herein, PAS may be administered in combination with other methods normally used to treat pathogenic bacterial infections. For instance, in some embodiments, PAS may be administered in combination with other methods normally used to treat urinary tract infections. Non-limiting examples of methods normally used to treat urinary tract infections may include the administration of antibiotics.

III. Yersiniabactin Therapeutic

Superoxide radicals ($O_2^-$) may be generated within living cells during both enzymatic and non-enzymatic oxidations. Superoxide radicals present a threat to cellular integrity; they are directly reactive, and may generate secondary free radicals that may also be reactive. Cells counter the threat of superoxide radicals by a family of defensive enzymes, superoxide dismutases (SOD) that catalyze the conversion of $O_2^-$ to $H_2O_2$ and $O_2$. The $H_2O_2$ generated by SOD is disposed of either by catalytic conversion to $O_2$ and $H_2O$ by catalases or by reduction to water at the expense of thiol, amine or phenolic substrates by peroxidases.

It has been shown that yersiniabactin complexed with a redox-active metal comprises a superoxide dismutase activity that catalyzes the dismutation of superoxide anions. In one aspect, the present invention provides a compound comprising a superoxide dismutase activity, wherein the compound is yersiniabactin complexed with a redox-active metal. Non-limiting examples of a redox-active metal may include copper and iron.

In exemplary embodiments, the compound comprising a superoxide dismutase activity is yersiniabactin complexed with copper. In exemplary embodiments, the compound comprising a superoxide dismutase activity is cupric yersiniabactin.

In other embodiments, the compound comprising a superoxide dismutase activity may be yersiniabactin complexed with iron, for instance, ferric yersiniabactin.

Yersiniabactin may be purified from bacteria capable of producing yersiniabactin or from culture supernatants of such bacteria capable of producing yersiniabactin. Alternatively, yersiniabactin may be chemically synthesized. See e.g., Roberts et al., (2010) Top Curr Chem. 297:149-203. In some embodiments, yersiniabactin is chemically synthesized. In other embodiments, yersiniabactin is purified from bacteria capable of producing yersiniabactin or from culture supernatants of such bacteria capable of producing yersiniabactin. In preferred embodiments, yersiniabactin is purified from bacteria capable of producing yersiniabactin or from culture supernatants of such bacteria as described in the Examples.

In another aspect, the invention provides a method of catalyzing the dismutation of a superoxide radical. The method comprises contacting the superoxide radical with yersiniabactin complexed with a redox-active metal. Such a method may be useful to treat, prevent, or reduce the symptoms of a condition caused by superoxide radicals. Superoxide radicals have been shown to be an important causative factor in cellular damage resulting from autoxidation, oxygen toxicity, the oxygen-dependent toxicity of numerous compounds, reperfusion injury, frostbite, an autoimmune condition, a cardiovascular condition, and inflammatory conditions. Each of which is described in more detail below. In an exemplary embodiment, the superoxide radical is produced by a macrophage or other immune system related cell.

Non limiting examples of inflammatory conditions may include allergic rhinitis, ankylosing spondylitis, arthritis, asthma, Behcet syndrome, bursitis, chronic obstructive pulmonary disease (COPD), Churg-Strauss syndrome, dermatitis, gout, Henoch-Schonlein purpura, inflammatory bowel disease (Crohn's disease or ulcerative colitis), inflammatory neuropathy, Kawasaki disease, myositis, neuritis, pericarditis, polyarteritis nodosa, polymyalgia rheumatica, prostatitis, psoriasis, radiation injury, sarcoidosis, shock, systemic inflammatory response syndrome (SIRS), Takayasu's arteritis, temporal arteritis, thromboangiitis obliterans (Buerger's disease), vasculitis, and Wegener's granulomatosis.

Autoimmune conditions are conditions caused by an immune response against the body's own tissues. Autoimmune conditions may result in destruction of one or more types of body tissues, abnormal growth of an organ, or changes in organ function. The autoimmune condition may affect only one organ or tissue type or may affect multiple organs and tissues. Non limiting examples of organs and tissues affected by autoimmune conditions may include but are not limited to blood, blood vessels, connective tissues, muscles, joints, skin, and endocrine glands. Non-limiting examples of autoimmune or autoimmune-related conditions may include Addison's disease, chronic thyroiditis, dermatomyositis, Grave's disease, Hashimoto's thyroiditis, hypersensitivity pneumonitis, insulin-dependent diabetes mellitus, insulin-independent diabetes mellitus, multiple sclerosis, myasthenia gravis, organ transplantation, pernicious anemia, Reiter's syndrome, rheumatoid arthritis, Sjogren's syndrome, systemic lupus erythematosis (SLE), thyroiditis, and urticaria.

Non limiting examples of cardiovascular conditions may include ischemia-reperfusion injury, diabetic retinopathy, diabetic nephropathy, renal fibrosis, hypertension, atherosclerosis, arteriosclerosis, atherosclerotic plaque, atherosclerotic plaque rupture, cerebrovascular accident (stroke), transient ischemic attack (TIA), peripheral artery disease, arterial occlusive disease, vascular aneurysm, ischemia, ischemic ulcer, heart valve stenosis, heart valve regurgitation, intermittent claudication, coronary artery disease, ischemic cardiomyopathy, myocardial ischemia, and ischemic or post-myocardial ischemia revascularization.

Other non limiting examples of conditions that may be caused by superoxide radicals may include cancer, sepsis, pain, cataracts, and the limited viability of transplanted organs and tissues. In some embodiments, the invention provides a method of treating sepsis. In other embodiments, the invention provides a method of treating pain. In yet other embodiments, the invention provides a method of treating cataracts. In other embodiments, the invention provides a method of treating cancer. In still other embodiments, the invention provides a method of treating stroke. In additional embodiments, the invention provides a method of treating myocardial infarction. In other embodiments, the invention provides a method of treating diabetes. In yet other embodiments, the invention provides a method of increasing the viability of transplanted organs and tissues.

As used herein, the term "treat" may be used to describe prophylaxis, amelioration, prevention or cure of a condition and/or one or more of its associated symptoms. For instance, treatment of an existing condition may reduce, ameliorate or altogether eliminate the condition, or prevent it from worsening. Prophylactic treatment may reduce the risk of developing the condition and/or lessen its severity if the condition later develops.

In yet another aspect, the invention provides a pharmaceutical composition comprising yersiniabactin complexed with a redox-active metal. Methods of administering a compound such as yersiniabactin complexed with a redox-active metal are known in the art, and are as described in Section (II).

IV. Method for Determining Whether a Subject would Benefit from a Compound that Inhibits Yersiniabactin Another aspect of the invention encompasses a method for determining whether a subject would benefit from a compound that inhibits yersiniabactin. The method comprises obtaining a sample from the subject, analyzing the sample, in vitro, for the presence or absence of cupric yersiniabactin or a product thereof, and identifying the subject as a subject that would benefit from a compound that inhibits yersiniabactin when cupric yersiniabactin or a product thereof is present in the sample.

As not all pathogenic bacteria produce yersiniabactin, it would not be beneficial to treat all suspected pathogenic bacterial infections with an inhibitor of yersiniabactin. If, however, cupric yersiniabactin or a product thereof were detected in a sample from the subject, then the subject is infected with pathogenic bacteria that produce yersiniabactin, and it stands to reason that the subject would benefit from the administration of a yersiniabactin inhibitor.

In still another aspect, the invention encompasses a method for determining whether a subject would benefit from antimicrobial therapy. The method comprises obtaining a sample from the subject, analyzing the sample, in vitro, for the presence or absence of cupric yersiniabactin or a product thereof, and identifying the subject as a subject that would benefit from antimicrobial therapy when cupric yersiniabactin or a product thereof is present in the sample. As used herein, antimicrobial therapy may include any antibiotic or antibacterial used specifically against bacteria. An antibiotic or antibacterial may either kill or inhibit the growth of bacteria. In certain embodiments, the antibiotic or antibacterial may include sulfamethoxazole-trimethoprim (Bactrim, Septra, others), amoxicillin (Amoxil, Augmentin, others), nitrofurantoin (Furadantin, Macrodantin, others), ampicillin, ciprofloxacin (Cipro), or levofloxacin (Levaquin). Alternatively, antimicrobial therapy may include an antivirulence therapeutic. An antivirulence therapeutic may not kill or inhibit the growth of a bacteria but instead targets a virulence factor of that bacteria such that it cannot cause infection in the host.

Suitable samples, methods of obtaining the samples, and methods of analyzing a sample for the presence or absence of cupric yersiniabactin are as detailed above in Section I.

V. Methods for Determining the Antibiotic Susceptibility of Pathogenic Bacteria

The inventors have discovered that a combination of virulence factors may be used to identify antibiotic susceptibility of pathogenic bacteria. Such identification allows physicians the ability to strategically treat patients such that the incidence of treatment failures due to antibiotic resistance may be greatly reduced. Accordingly, the present invention provides a method for determining the antibiotic susceptibility of pathogenic bacteria, the method generally comprises determining the presence or absence of a group of virulence factors and using the particular combination of virulence factors to identify the antibiotic susceptibility of the pathogenic bacteria. In a specific embodiment, the virulence factors are siderophores. As used herein, "siderophores" are small, high-affinity metal (typically iron) chelating compounds secreted by microorganisms. Non-limiting examples of siderophores include aerobactin, yersiniabactin, salmochelin, enterobactin, ferrichrome, coprogen, vibriobactin, pyoverdin, alcaligin, mycobactin, staphyloferrin A and petrobactin. Iron acquisition systems, such as the hemin uptake system or the iron/manganese transport, may also serve a similar purpose as siderophores and may also be suitable virulence factors for use herein. Preferred siderophores include aerobactin, yersiniabactin, and salmochelin.

In an aspect, the invention encompasses a method for determining the antibiotic susceptibility of pathogenic bacteria in a subject, the method comprising (a) obtaining a sample for the subject; (b) analyzing the sample, in vitro, for the presence or absence of siderophores selected from the group comprising yersiniabactin, salmochelin and aerobactin; (c) identifying the combination of siderophores present wherein the combination indicates susceptibility according to the following: (i) the presence of yersiniabactin only indicates susceptibility to ciprofloxacin (cipro); (ii) the presence of yersiniabactin+aerobactin indicates resistance to cipro and trimepthoprim-sulfamethoxazole (TMP-SMZ); (iii) the presence of yersiniabactin+salmochelin indicates susceptibility to cipro and TMP-SMZ; (iv) the presence of yersiniabactin+aerobactin+salmochelin indicates susceptibility to cipro; (v) the presence of aerobactin indicates resistance to cipro; and (vi) the absence of yersiniabactin+aerobactin+salmochelin indicates susceptibility to cipro. In certain embodiments, siderophores are selected from the group consisting of yersiniabactin, salmochelin and aerobactin. In exemplary embodiments, a method of the invention may be used to determine the antibiotic susceptibility of pathogenic bacteria in the urinary tract of a subject. In other exemplary embodiments, the invention provides a method for determining the antibiotic susceptibility of uropathogenic Escherichia coli. The subject and sample may be as described in Section I(a) and Section I(b) above.

Analyzing the sample, in vitro, for the presence or absence of siderophores may comprise detecting the siderophore or product thereof via mass spectrometry or epitope binding agent methods as described in Section I(c). Specifically, the epitope binding agent-based method may be a lateral flow assay to detect the presence or absence of yersiniabactin, salmochelin and/or aerobactin. Alternatively, analyzing the sample, in vitro, for the presence or absence of siderophores may comprise detecting one or more nucleic acids involved in the biosynthesis of the siderophore. Siderophores, specifically yersiniabactin, aerobactin and salmochelin, are synthesized via large pathogenicity islands. These pathogenicity islands contain multiple genes or nucleic acids that play a role in the biosynthesis of the siderophore. The nucleic acid itself or the protein product from the nucleic acid may play a role in the biosynthesis of the siderophore. Accordingly, the presence or absence of one or more nucleic acids involved in the biosynthesis of the siderophore may indicate the presence or absence of said siderophore. It is within the ability of one with skill in the art to determine the various nucleic acids involved in the biosynthetic pathway of a siderophore. By way of non-limiting example, yersiniabactin may be detected by detecting the presence of the nucleic acid fyuA, ybtS, ybtE, ybtP, ybtQ, ybtX, HMWP1/irp1, HMWP2/irp2, ybtU, ybtA, and/or ybtT; salmochelin may be detected by detecting the presence of the nucleic acid iroN, iroB, iroC, iroD, iroE, and/or sequences within the iroA cassette; and aerobactin may be detected by detecting the presence of the nucleic acid iucD, iucA, iucB, iucC, iucD, and/or iutA. In a specific embodiment, yersinibactin may be detected by detecting the presence of the nucleic acid fyuA; salmochelin may be detected by detecting the presence of the nucleic acid iroN; and aerobactin may be detected by detecting the presence of the nucleic acid iucD. However, it is understood that other nucleic acids with the biosynthetic pathway may be detected to detect the presence of yersiniabactin, salmochelin and aerobactin. Accordingly, in a specific embodiment, the invention encompasses a method for determining the antibiotic susceptibility of pathogenic bacteria in a subject, the method comprising (a) obtaining a sample for the subject; (b) analyzing the sample, in vitro, for the presence or absence of siderophores selected from the group comprising yersiniabactin, salmochelin and aerobactin; (c) identifying the combination of siderophores present wherein the combination indicates susceptibility according to the following: (i) the presence of fyuA only indicates susceptibility to ciprofloxacin (cipro); (ii) the presence of fyuA+iucD indicates resistance to cipro and trimepthoprim-sulfamethoxazole (TMP-SMZ); (iii) the presence of fyuA+iroN indicates susceptibility to cipro and TMP-SMZ; (iv) the presence of fyuA+iucD+iroN indicates susceptibility to cipro; (v) the presence of iucD indicates resistance to cipro; and (vi) the absence of fyuA+iucD+iroN indicates susceptibility to cipro. Methods of detecting a nucleic acid are described below.

Methods for assessing nucleic acid expression in cells are well known in the art, and all suitable methods for assessing nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of DNA expressed or a specific variant or other portion of the DNA, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess nucleic acid expression may include arrays, such as microarrays, PCR, such as RT-PCR (including quantitative RT-PCR), nuclease protection assays and Northern blot analyses. In a specific embodiment, determining the expression of a target nucleic acid comprises, in part, measuring the level of target nucleic acid DNA expression.

In one embodiment, the nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using PCR. Methods of performing PCR are common in the art. In such an embodiment, the primers used for PCR may comprise a forward and reverse primer for a target nucleic acid. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The nucleic acid expression may be measured by measuring an entire coding region for a nucleic acid sequence, or measuring a portion of the coding region for a nucleic acid sequence. For instance, if a nucleic acid array is utilized to measure the nucleic acid expression, the array may comprise a probe for a portion of the coding region of the nucleic acid sequence of interest, or the array may comprise a probe for the full coding region of the nucleic acid sequence of interest. One of skill in the art will recognize that there is more than one set of primers that may be used to amplify either the entire or a portion of the coding region for a nucleic acid sequence of interest. Methods of designing primers are known in the art. Methods of extracting nucleic acid from a biological sample are known in the art.

Once the sample has been analyzed for the presence or absence of siderophores, the combination of siderophores present may be identified to indicate the susceptibility of the pathogenic bacteria. The inventors have discovered that different virulence strategies are linked with antibiotic resistance. Specifically, the inventors have discovered six different virulence strategists with differing combinations of siderophores. These different virulence strategists were evaluated for their susceptibility to two common antibiotics: trimethoprim-sulfamethoxazole (TMP-SMZ) and ciprofloxacin (cipro). The following associations were identified between the combination of siderophores and antibiotic susceptibility: (i) the presence of yersiniabactin only indicates susceptibility to ciprofloxacin (cipro); (ii) the presence of yersiniabactin+aerobactin indicates resistance to cipro and trimepthoprim-sulfamethoxazole (TMP-SMZ); (iii) the presence of yersiniabactin+salmochelin indicates susceptibility to cipro and TMP-SMZ; (iv) the presence of yersiniabactin+aerobactin+salmochelin indicates susceptibility to cipro; (v) the presence of aerobactin indicates resistance to cipro; and (vi) the absence of yersiniabactin+aerobactin+salmochelin indicates susceptibility to cipro. Further, it is noted that (iv) the presence of yersiniabactin+aerobactin+salmochelin is also associated with moderate sensitivity to TMP-SMZ. Additionally, (v) the presence of aerobactin is also associated with moderate resistance to TMP-SMZ.

Based on the combination of siderophores, the subject may be treated with the appropriate antimicrobial therapy. For example, a subject whose sample comprises: (i) the presence of yersiniabactin only may be treated with cipro; (ii) the presence of yersiniabactin+aerobactin may be treated with antimicrobial therapy other than cipro or TMP-SMZ; (iii) the presence of yersiniabactin+salmochelin may be treated with cipro or TMP-SMZ; (iv) the presence of yersiniabactin+aerobactin+salmochelin may be treated with cipro; (v) the presence of aerobactin may be treated with antimicrobial therapy other than cipro or TMP-SMZ; and (vi) the absence of yersiniabactin+aerobactin+salmochelin may be treated with cipro. It is understood that the above example is just a guideline and the subject may be treated with various other antimicrobial therapies provided they are not in the same class as that for which the combination of siderophores indicates resistance. Non-limiting examples of other antimicrobial therapies may include sulfamethoxazole-trimethoprim (Bactrim, Septra, others), amoxicillin (Amoxil, Augmentin, others), nitrofurantoin (Furadantin, Macrodantin, others), ampicillin, ciprofloxacin (Cipro), or levofloxacin (Levaquin). Alternatively, antimicrobial therapy may include an antivirulence therapeutic as described above. Accordingly, using a method of the invention, the subject may be treated with antimicrobial therapy that is more likely to clear the infection from the pathogenic bacteria.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples 1-10

Siderophores are a chemically diverse group of secondary metabolites used extensively by microbes—and possibly higher vertebrates—to bind and acquire ferric iron. While chemists have recognized the ability of some siderophores to bind non-ferric metal ions, investigations into pathophysiologic functions of siderophores have solely addressed their favorable interaction with ferric iron. The marked chemical diversity and differential iron binding affinities among siderophores raises the possibility that some may have evolved to bind non-ferric metal ions to fulfill additional physiologic functions. Indeed, alterations in physiologic metal composition at sites of infection may have driven bacterial pathogens to secrete siderophores with differential metal specificity to maintain fitness within the host. Understanding the functional consequences arising from this chemical coevolution between host and pathogen may provide new insights into the selective pressures driving siderophore chemistry and bacterial pathogenesis.

Genetic and metabolomic studies associate siderophore production with virulence among multiple human pathogens, particularly among *E. coli* and related Gram-negatives.

Although bacterial expression of a single siderophore type is sufficient for iron acquisition in vitro, most uropathogenic *E. coli* (UPEC) express multiple siderophore types, often including the virulence-associated phenolate/thiazolidine siderophore yersiniabactin. All yersiniabactin-expressing UPEC strains described to date co-express the chemically distinct, catecholate siderophore enterobactin (FIG. 1) and occasionally the enterobactin derivative salmochelin. Epidemiologic studies suggest that *E. coli* strains that progress from bladder infection to kidney or bloodstream infection are more likely to carry the fyuA gene, a correlate of yersiniabactin producing strains. Exactly how yersiniabactin expression facilitates invasive infections has been unclear.

The examples below describe a mass spectrometry-based screen devised to determine whether non-ferric metals bind yersiniabactin in physiologically relevant fluids. This approach identified prominent copper (II) binding by yersiniabactin in human urine. Direct mass spectrometric analyses of urine from humans and mice confirm the presence of copper(II)-yersiniabactin complexes during infection with yersiniabactin-expressing strains. Functional studies demonstrate that this binding interaction is competitive with iron (III) and protects uropathogens by binding copper and preventing its catecholate-mediated reduction. Together, these studies reveal a new activity for yersiniabactin as a pathogenic countermeasure to copper-based antibacterial functions in humans.

Example 1

Figure 2A:
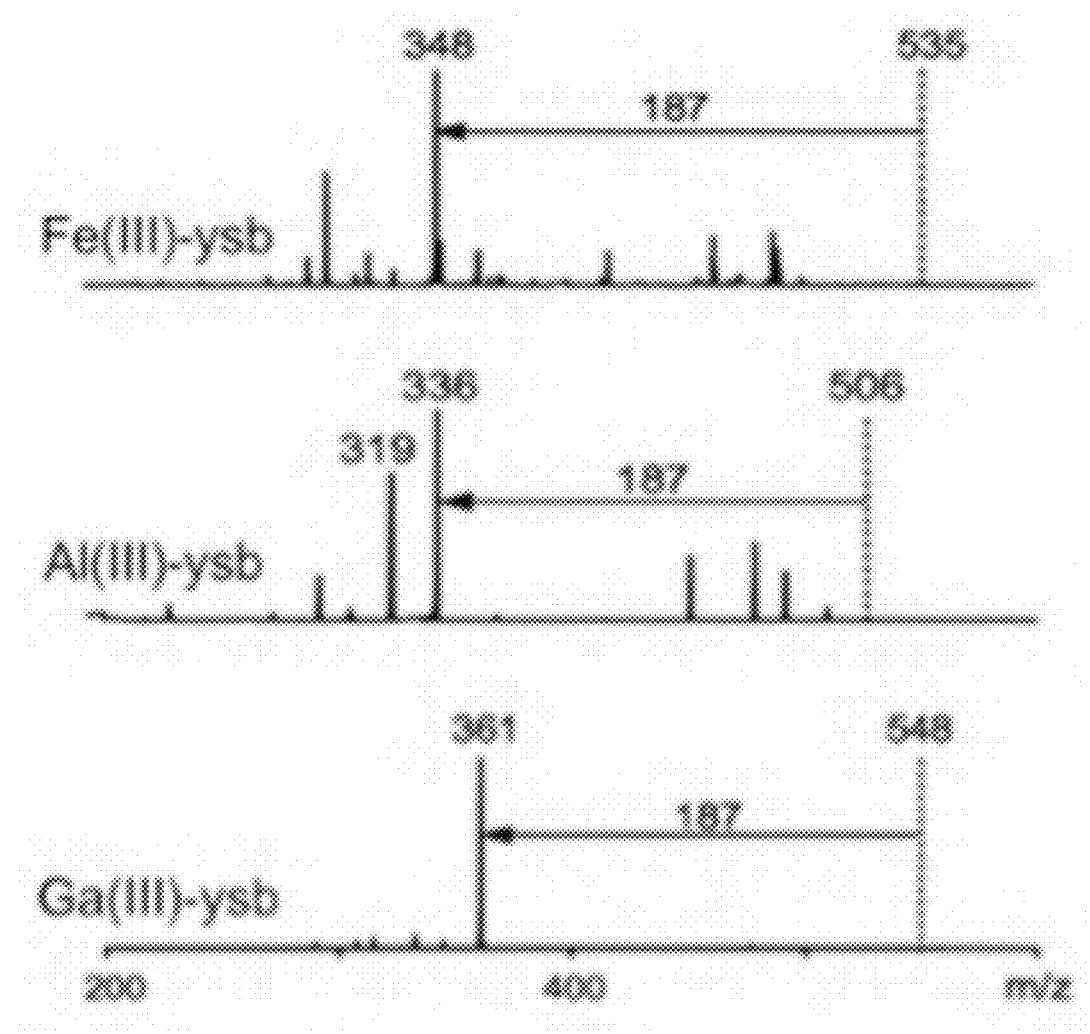
FIG. 2A-D depicts graphs and structures showing a novel metal-yersiniabactin complex is revealed by a LC-constant neutral loss screen.
Figure 2B:
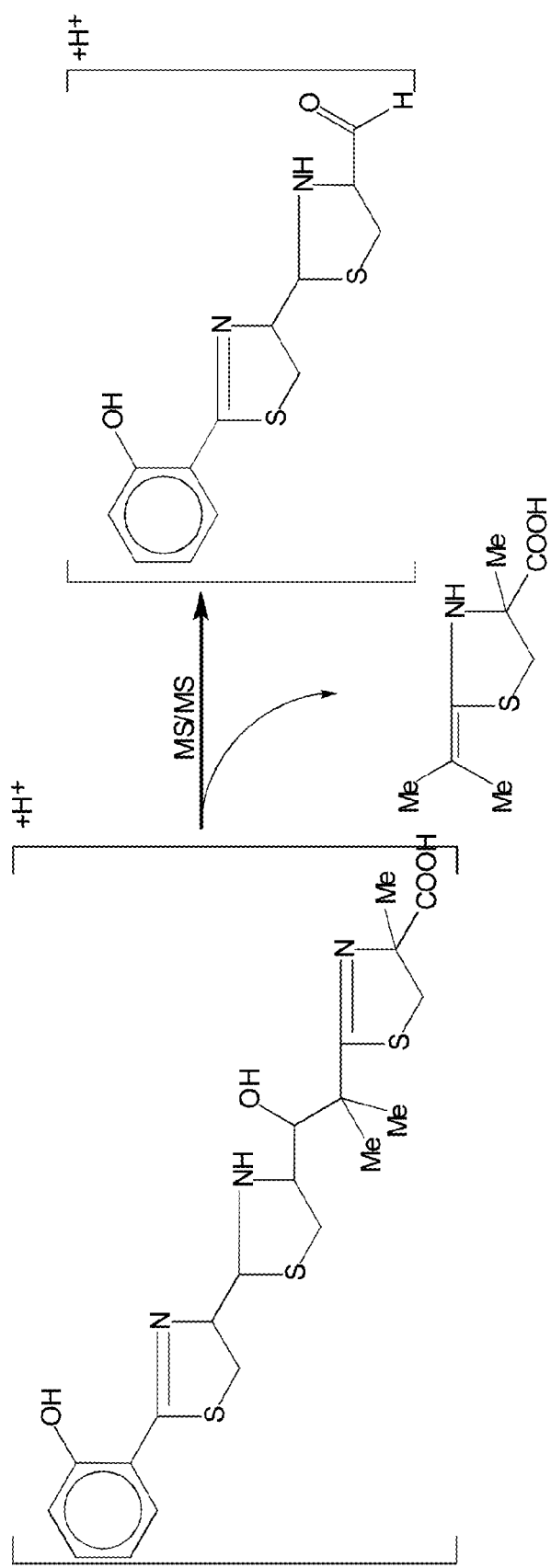
Figure 2C:
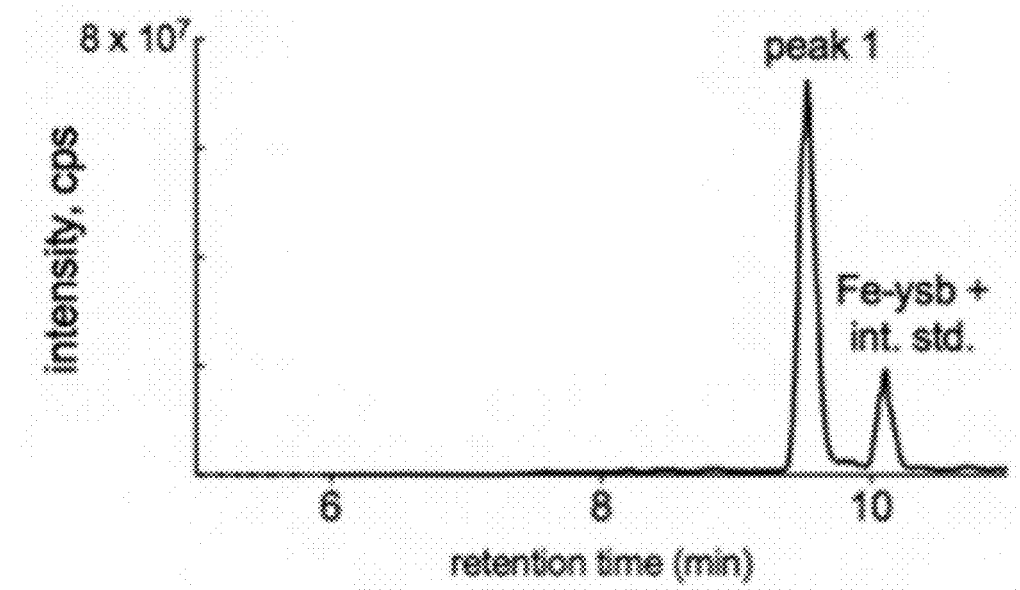
Figure 2D:
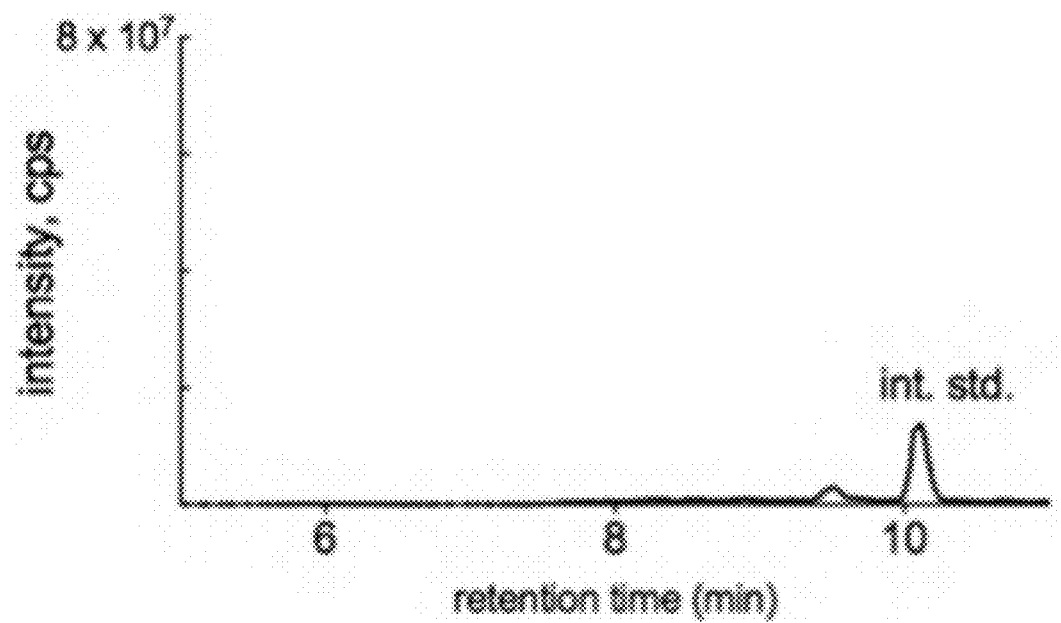

A Liquid Chromatography-Mass Spectrometry Screen Reveals a New Yersiniabactin-Metal Complex To screen for metals that bind yersiniabactin (Ybt) in a biologically relevant environment, a liquid chromatography-constant neutral loss (LC-CNL) mass spectrometric screen based on a common ion fragmentation pathway identified for model metal-yersiniabactin complexes was devised. This fragmentation pathway results in a 187 mass unit neutral loss, consistent with rearrangement of the C13-C14 bond to lose the carboxy-terminal thiazoline ($C_8H_{13}NO_2S$, FIGS. 2A and 2B). To identify biologically relevant metal-Ybt complexes, we added apo-Ybt to pooled urine samples from six healthy donors and analyzed the mixture using LC-CNL over a mass range encompassing the calculated range of naturally-occurring terrestrial metal complexes ($^6Li$ to $^{239}Pu$). The LC-CNL ion chromatogram revealed formation of a dominant, novel analyte with m/z 543 (peak 1, FIG. 2C) in addition to a peak corresponding to Fe(III)-Ybt and its deuterated internal standard. The new peak 1 was absent in urine alone treated with internal standard (FIG. 2D) or when apo-Ybt was added to water (data not shown). Although urine is a highly complex mixture containing thousands of small biomolecules, the simplicity of the resulting chromatograms suggests that the 187 mass unit loss is highly specific to Ybt. Peak 1 matched no previously reported spectra, also exhibited a neutral loss of 187 mass units, and was formed by adding apo-Ybt to urine, suggesting formation of a new and biologically plausible yersiniabactin complex.

Example 2

Yersiniabactin is a Copper (II) Ligand

Figure 3A:
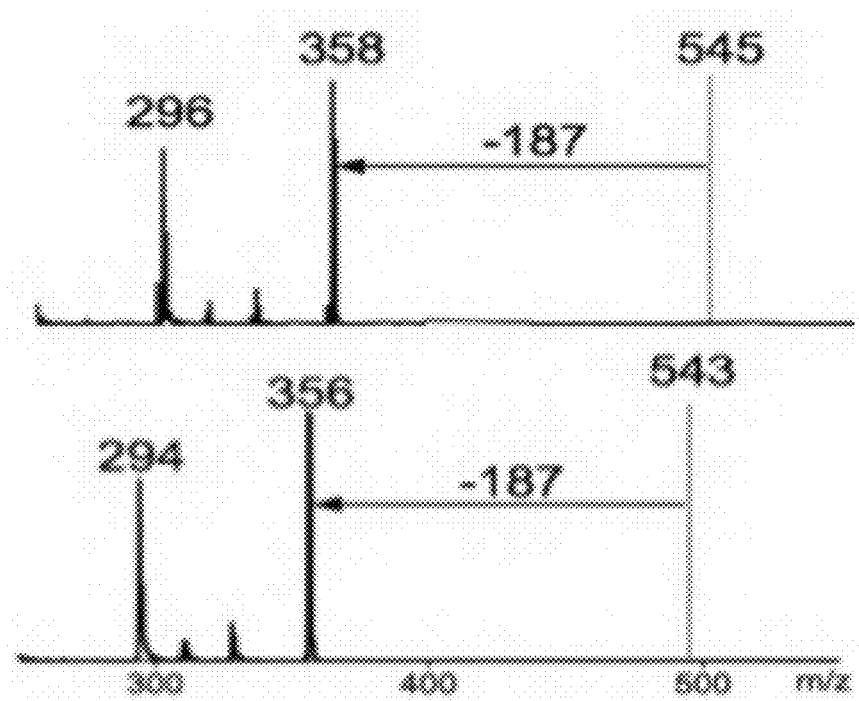
FIG. 3A-D depicts graphs showing Peak 1 is a stable cupric-yersiniabactin complex.

Peak 1 was first subjected to additional mass analyses. The CNL mass spectrum of this complex exhibited a prominent M+2 peak at m/z 545, approximately one third the height of the base peak. MS/MS analysis of the M and M+2 peaks at m/z 543 and 545 exhibited product ion spectra with identical fragmentation patterns differing by 2 mass units (FIG. 3A). The apo-Ybt spectrum lacks this prominent M+2 peak, suggesting a prominent isotope pattern contribution from the unknown Ybt binding partner. A Ybt-derived base peak ion 61 mass units higher than the Ybt [M+H]$^+$ ion with a prominent M+2 isotope peak was consistent with a singly charged cupric complex of the form [Ybt+Cu(II)-H]$^+$. The observed isotopic pattern is consistent with the natural $^{63}Cu$ and $^{65}Cu$ isotope abundances of 77% and 23%, respectively. The m/z value of this complex is consistent with the presence of copper (II), rather than copper (I), which would require an additional proton to yield a singly charged ion at m/z 544, rather than the observed 543.

Figure 3B:
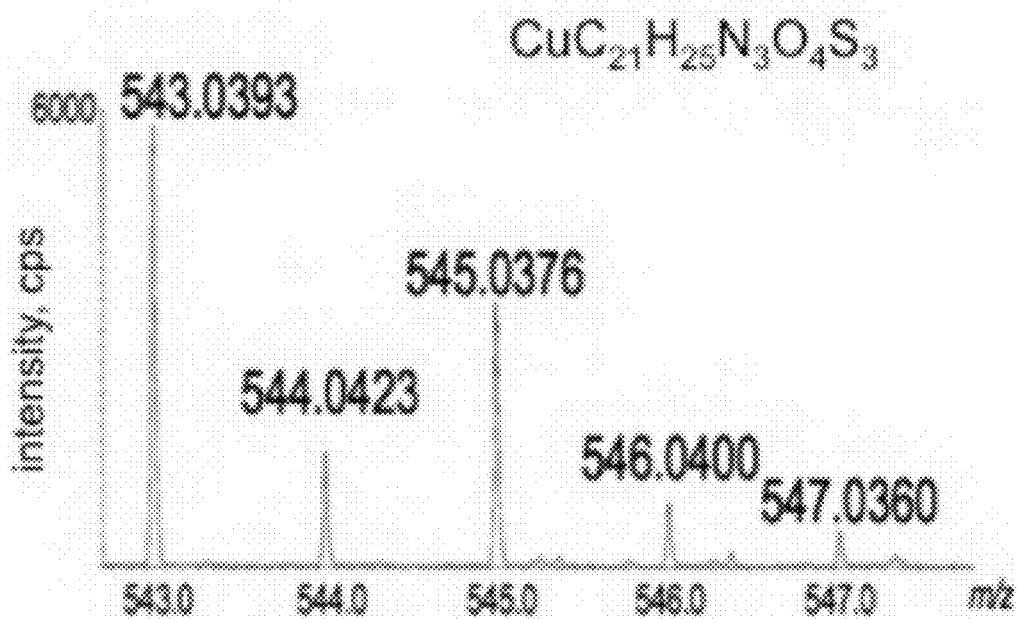

Further confirmation was pursued by adding molar excess of copper (II) sulfate to UT189 ΔentB (which produces Ybt as the only siderophore) culture supernatant, followed by preparative chromatography. Application of this copper(II)-treated supernatant to a preparative C18 column resulted in retention of a blue colored fraction on the column that was eluted with 80% methanol. The LC-MS chromatogram of this blue fraction was dominated by peak 1. This fraction was subjected to accurate mass determination on a Bruker Q-TOF Maxis using positive ion electrospray mode, which again showed the prominent M+2 ion and supported the formula $C_{21}H_{25}CuN_3O_4S_3$ for peak 1 ion at 543.0393 (FIG. 3B). The presence of 21 carbons was confirmed by detection of $^{13}C$-labeled peak 1 at m/z 564 in supernatants from bacteria grown in [$^{13}C_3$] glycerol. MS/MS of this peak 1 isotopologue revealed a new dominant MS/MS neutral loss of 195 mass units, supporting the proposed common $C_8H_{13}NO_2S$ neutral loss. Together, these results support the identity of peak 1 as a stable copper (II) complex of Ybt that forms spontaneously when Ybt is exposed to physiologic concentrations of copper in human urine.

Example 3

Figure 3C:
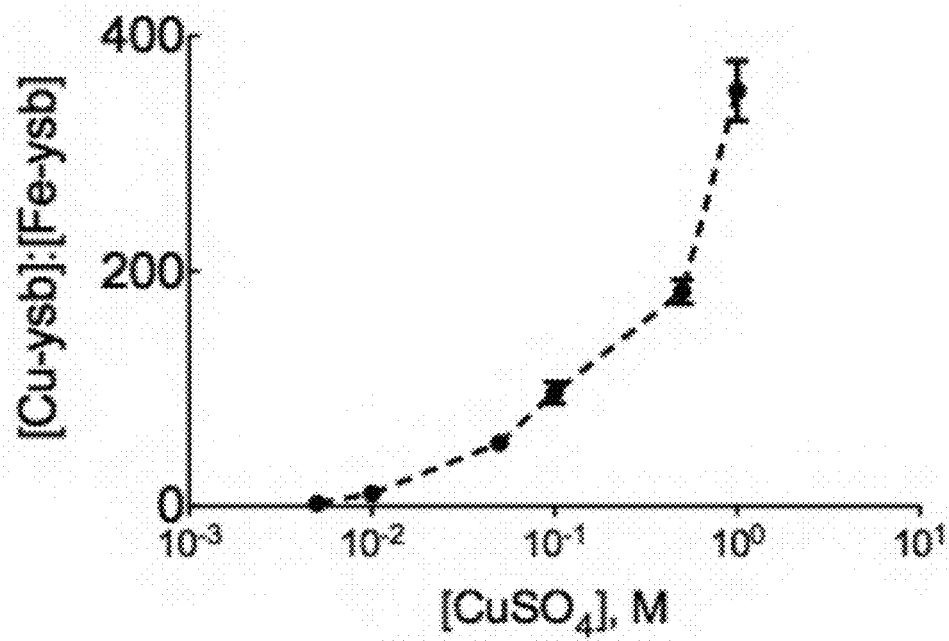

Copper(II) Competes with Iron (III) in Solution to Produce a Stable Cu(II)-Ybt Complex To determine whether cupric and ferric ion species bind competitively to Ybt, relative copper(II)- and iron(III)-yersiniabactin (Cu(II)-Ybt and Fe(III)-Ybt, respectively) yields were quantified in competitive binding experiments. Increasing concentrations of cupric sulfate were added to PBS containing 0.01 M ferric chloride at pH 7.0 at 25° C. for one hour (FIG. 3C). One micromolar apo-yersiniabactin was then added to these samples and the Cu(II)-Ybt/Fe(III)-Ybt ratio was determined by LC-MS following a two-hour incubation. The Cu(II)-Ybt/Fe(III)-Ybt ratio exhibited a positive correlation with copper (II) concentration, consistent with competitive binding between aqueous cupric and ferric species.

Figure 3D:
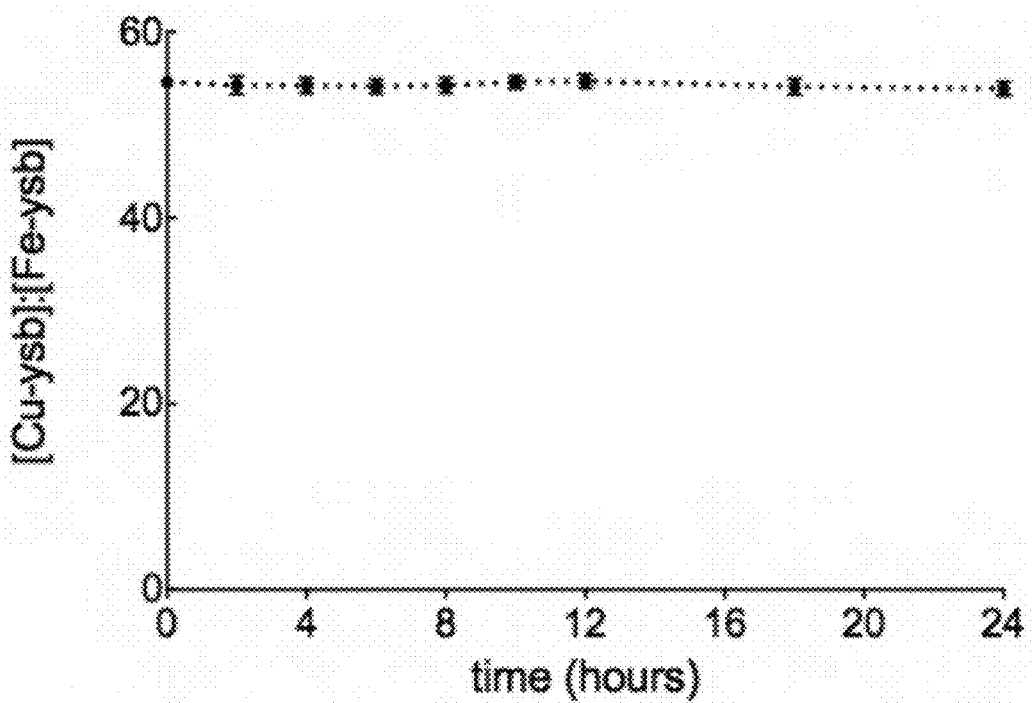

To determine whether iron displaces copper from Cu(II)-Ybt complexes in our experimental conditions, we monitored an extended time course of Cu(II)-Ybt levels in the presence of ferric ions. Twenty five micromolar apo-Ybt was incubated with 25 μM cupric sulfate for one hour to form Cu(II)-Ybt. Next, 0.025 M competing ferric chloride was added and the resulting Cu(II)-Ybt level was followed over a 24 hour time course (FIG. 3D). The Cu(II)-Ybt level was unchanged, consistent with a low rate of ferric ion displacement in our analytical and experimental conditions.

Example 4

Figure 4A:
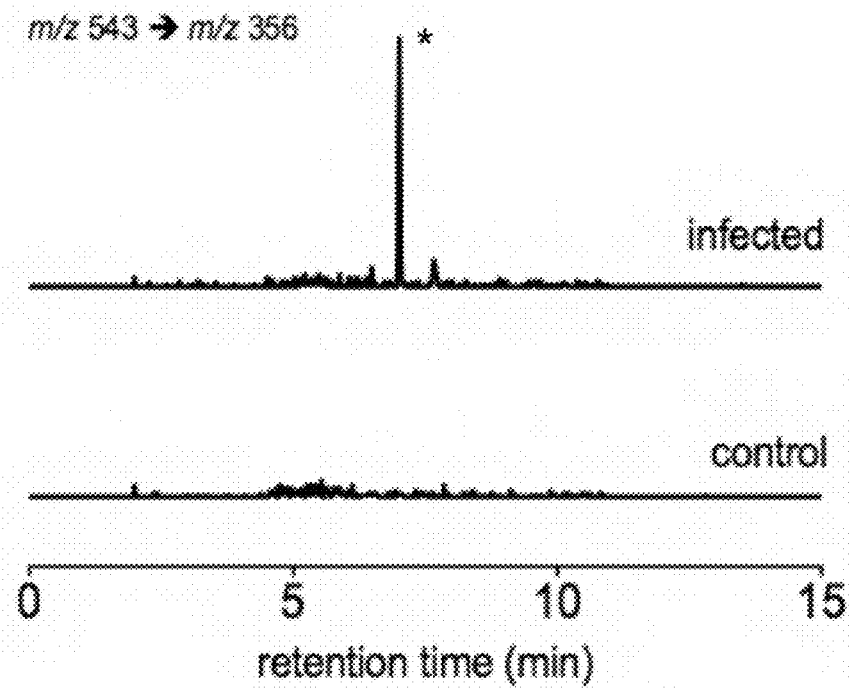
FIG. 4A-C depicts graphs showing cupric-yersiniabactin forms in murine bladder tissue and urine during experimental uropathogenic E. coli cystitis. Bladder tissue and urine were collected from infected mice and prepared for mass spectrometric analysis. Shown are MS/MS chromatograms showing Cu(II)-Ybt peaks in (FIG. 4A) bladder and (FIG. 4B) urine extracts from infected, but not uninfected, animals.
Figure 4B:
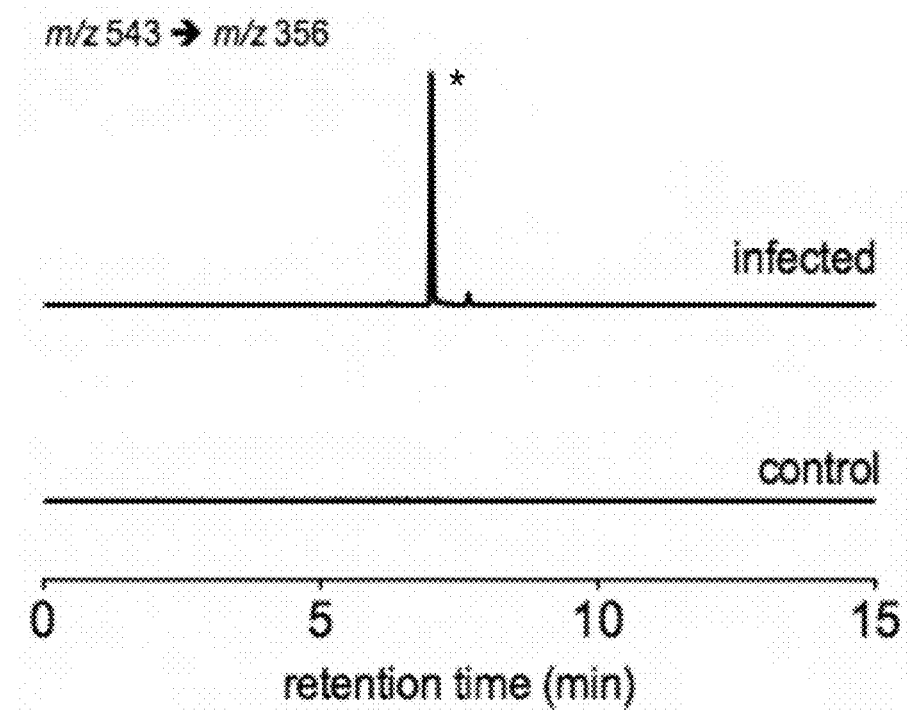
Figure 4C:
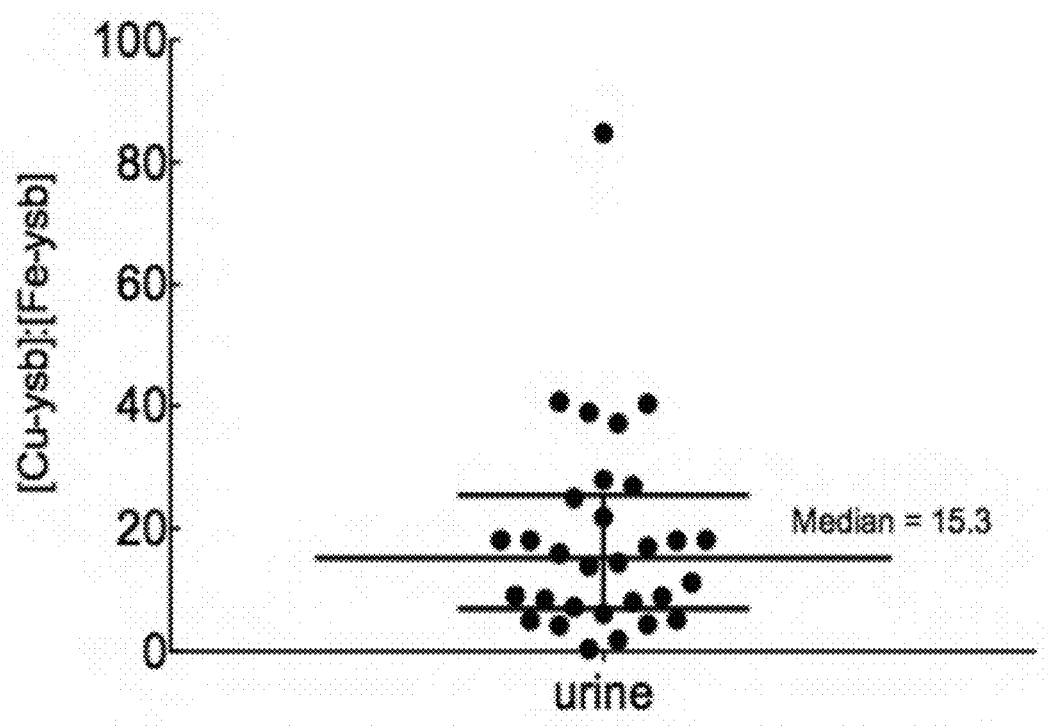

Urine and Tissue Extracts from Murine *E. coli* UTI Demonstrate In Vivo Cupric-Yersiniabactin Formations To determine whether Ybt is expressed and binds copper during infection, LC-MS/MS was used to analyze murine urine and bladder tissue following experimental infection with the model uropathogen UT189. A strong signal with the expected Cu(II)-Ybt MS/MS transition and retention time was observed in all 30 bladder tissue and urine sample from infected, but not mock infected, mice 24 hours after pathogen inoculation (FIGS. 4A and 4B). The median Cu(II)-Ybt/Fe(III)-Ybt molar ratio was 15.3 (range=0.38-84.8) (FIG. 4C). 29 of 30 (97%) urine samples from infected mice exhibited a Cu(II)-Ybt/Fe(III)-Ybt molar ratio >1, consistent with favorable in vivo Cu(II)-Ybt formation. These findings demonstrate that a typical urinary pathogen expresses Ybt during murine infections, and that a greater abundance of copper (II) complexed siderophore is subsequently detected in biological samples derived from infected mice.

Example 5

Cupric-Yersiniabactin Complexes Form During Human UTI

Figure 5A:
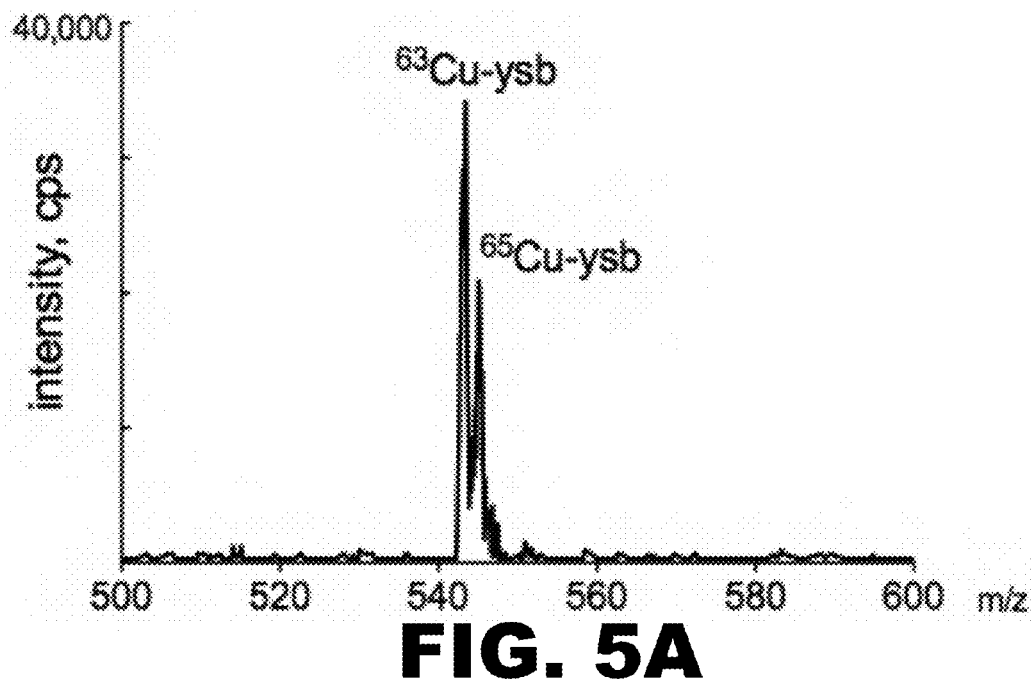
FIG. 5A-C depicts graphs showing cupric-yersiniabactin is produced in cystitis patients infected with yersiniabactin-producing strains.
Figure 5B:
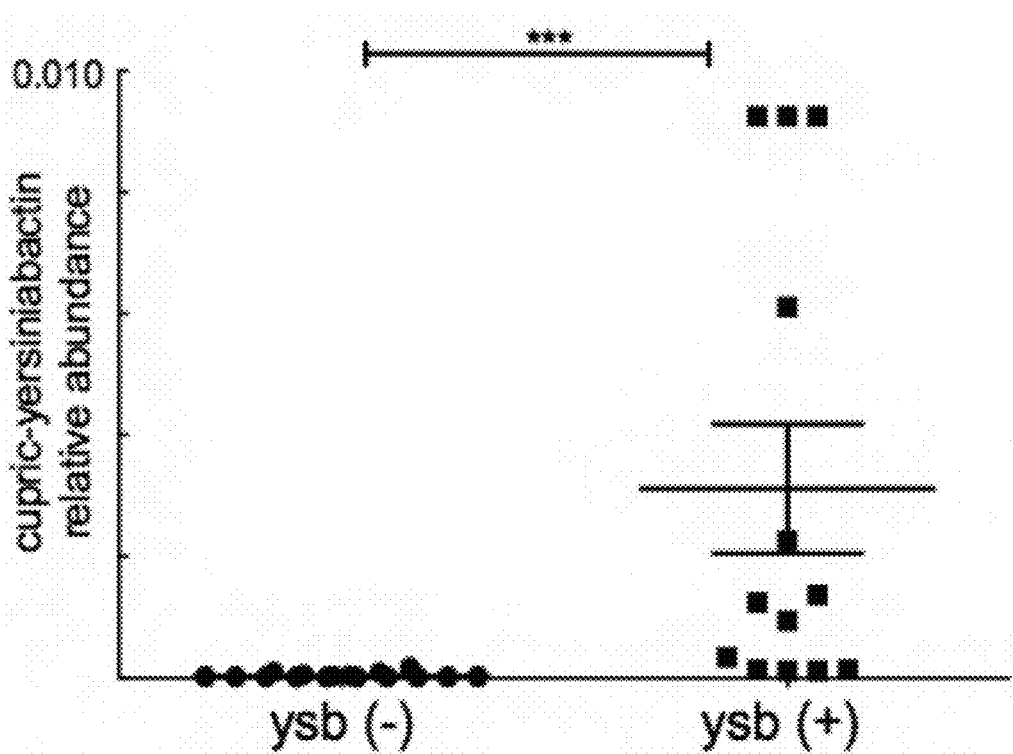

To determine whether Ybt is expressed and binds copper during human urinary tract infections, 32 midstream urine samples from a cohort of women with acute cystitis were analyzed for Cu(II)-Ybt. LC-MS/MS analysis of cultured urinary pathogen isolates from these patients confirmed infection by a Ybt-expressor in 15 out of 32 subjects. Scanning neutral loss analysis of urine from a patient infected with a Ybt-expressing strain revealed a strong Cu(II)-Ybt signal with the expected m/z 543 ion and its characteristic $^{65}$Cu isotopomer at m/z 545, confirming in vivo formation of Cu(II)-Ybt (FIG. 5A). Quantitative analysis using $^{13}$C-labeled internal standards demonstrated significantly ($p<0.0001$) higher urinary Cu(II)-Ybt levels in patients infected with Ybt expressors (13/15 positive) than in patients infected with non-expressors (0 of 17 positive) (FIG. 5B). Together, these data demonstrate that uropathogenic *E. coli* can express Ybt during human urinary tract infections and that this Ybt binds host-derived copper.

Figure 5C:
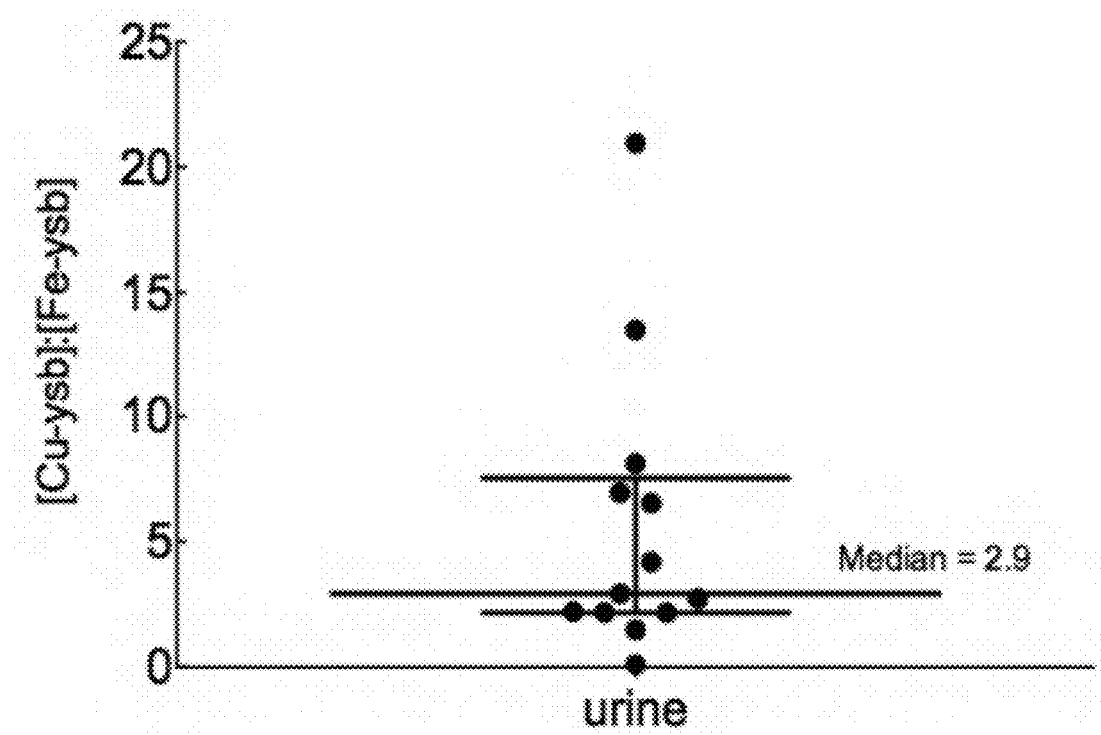

To determine whether the extent of in vivo copper and iron binding was similar, the Cu(II)-Ybt/Fe(III)-Ybt molar ratio in urine was measured. In the 13 samples with detectable Ybt complexes, the median Cu(II)-Ybt/Fe(III)-Ybt ratio was 2.9 (range=0.12-20.9) (FIG. 5C) with 92% (12/13) patients exhibiting a molar ratio >1. These data indicate that Ybt binds host-derived copper at least as extensively as ferric iron during human infections.

Example 6

Figure 6A:
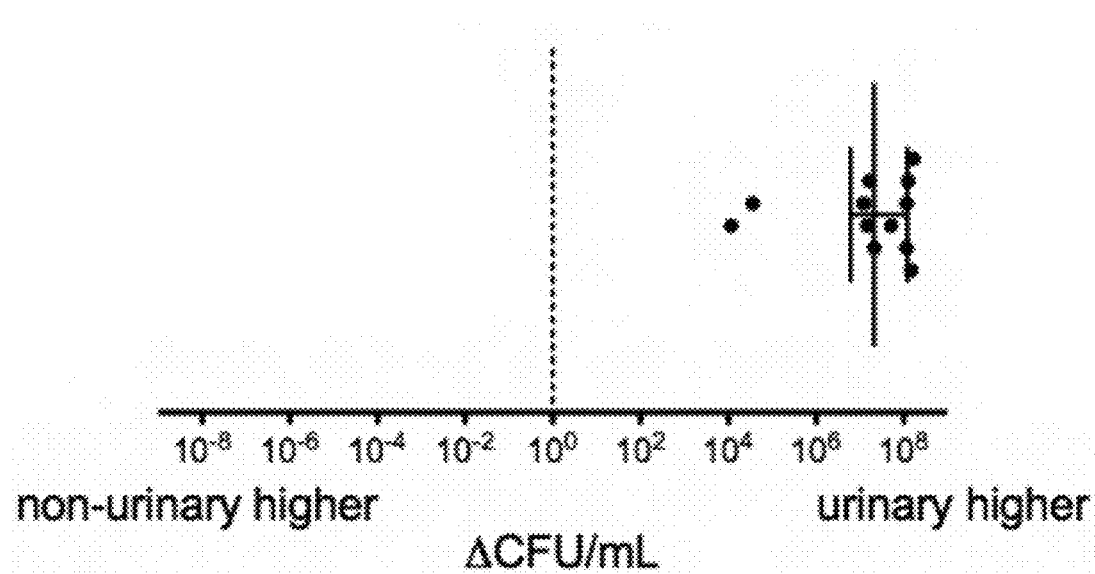
FIG. 6A-D depicts graphs showing that yersiniabactin promotes E. coli growth in copper-toxic conditions. Urinary and non-urinary E. coli isolates from a UTI patient population were cultured in the presence of 10 M copper (II) sulfate for 18 hours. Growth was determined and expressed as total CFU/mL.

Yersiniabactin Expression is Associated with Increased Copper Resistance Among Infection-Associated *E. coli* Isolates Copper ions are toxic to *E. coli* and other bacteria at low micromolar concentrations. By binding copper ions, Ybt may act as a pathogenic countermeasure to copper toxicity. To determine whether copper resistance is a virulence correlate, the effects of copper on bacterial growth in a previously described collection of co-existing urinary and non-urinary *E. coli* isolates from 13 UTI patients was measured. These experiments were conducted within the normal serum copper concentration range of 10 μM. This analysis revealed that the *E. coli* strains infecting the urinary tract were significantly ($p<0.0005$) more copper resistant than coexisting non-urinary strains from the same patients with 10 out of 13 urinary isolates exhibiting >$10^7$ higher CFU/mL (FIG. 6A).

Figure 6B:
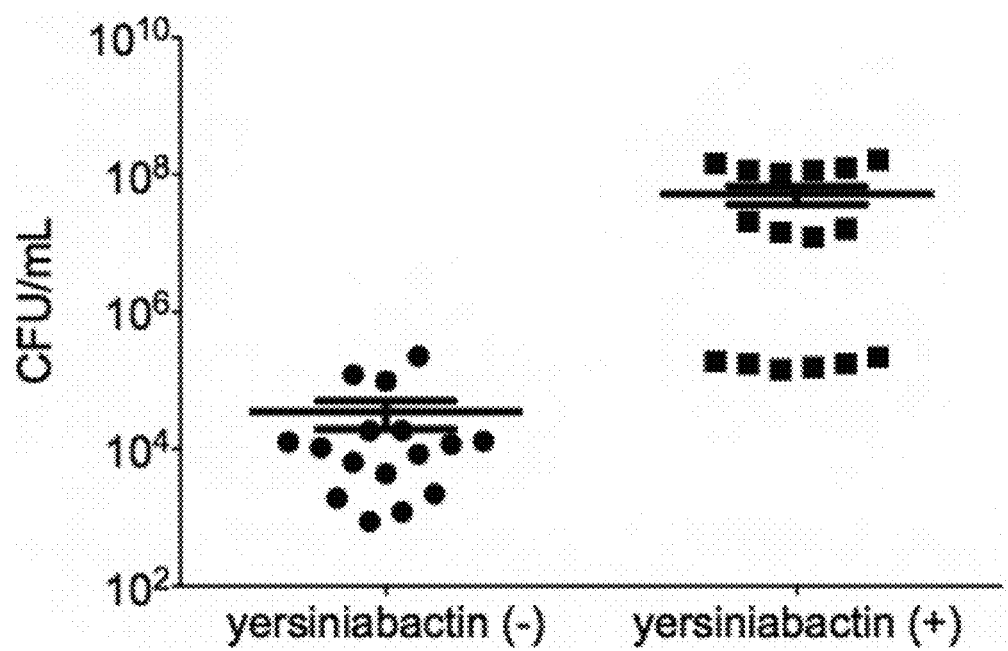

It is known from previous work that 10 of 14 urinary isolates and 6 of 18 non-urinary isolates produce Ybt. When growth in copper-supplemented media was grouped by Ybt expression, the Ybt-expressors exhibited significantly ($p<0.0013$) greater copper resistance (FIG. 6B). Together, these data show that urinary isolates exhibit greater copper resistance than non-urinary isolates in a UTI patient population and that enhanced copper resistance is strongly associated with Ybt production.

Example 7

Endogenous Yersiniabactin Production Protects Bacteria from Copper Toxicity

Figure 6C:
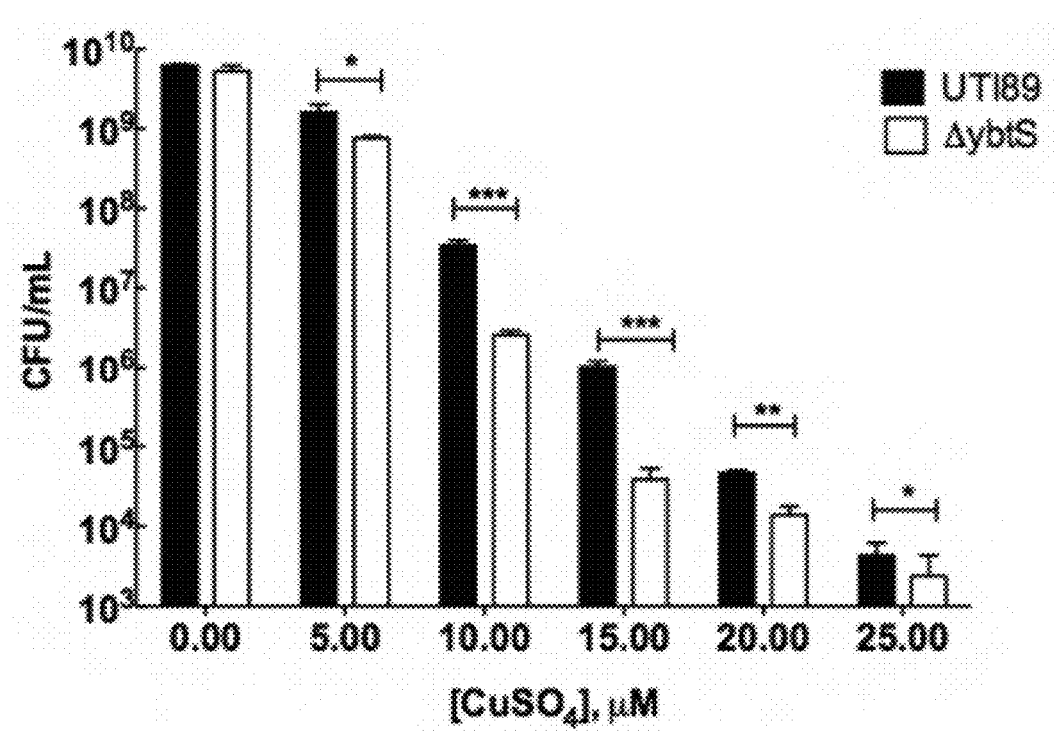

To determine whether Ybt production has a functional impact on copper resistance, the Ybt-deficient mutant UTI89ΔybtS was compared to the wild type uropathogen control UT189. After an 18 hour incubation, copper (II) sulfate inhibited UTI89ΔybtS growth significantly more than that of wild type UT189. Over a range of 5 to 25 μM copper (II) sulfate, wild type cultures yielded an average of 1.34 log more CFUs than UTI89ΔybtS cultures ($p=0.0032$, FIG. 6C). To confirm that Cu(II)-Ybt is expressed in this experimental system, LC-MS analysis of culture supernatants treated with 25 μM copper (II) sulfate was performed. Cu(II)-Ybt complexes were observed in wild type, but not UTI89ΔybtS, conditioned media (data not shown). Together, these findings show that intact Ybt gene plays a mechanistic role in copper resistance.

Example 8

Exogenous Apo-Yersiniabactin Protects Bacteria from Copper Toxicity

Figure 6D:
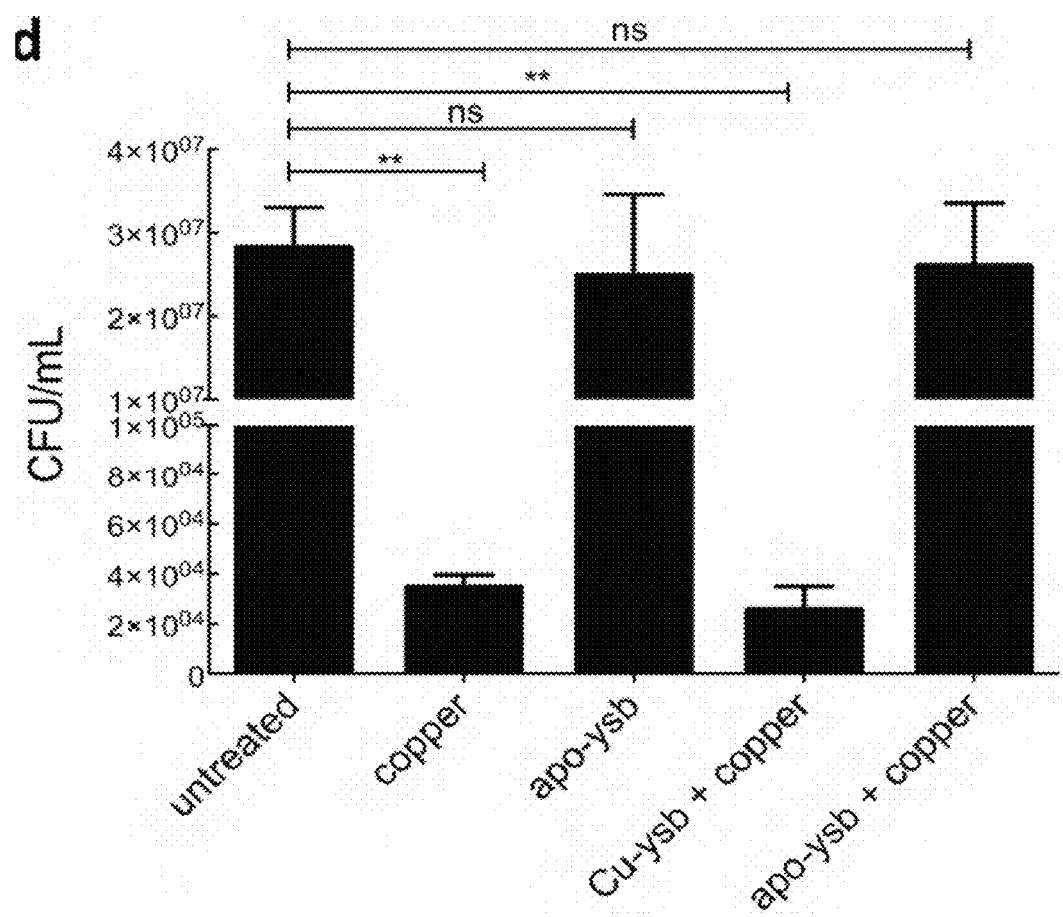

To determine whether Ybt directly protects bacteria from copper toxicity, the effect of purified apo-Ybt on viability of UTI89ΔybtS (Ybt biosynthesis mutant) cultures exposed to 10 μM copper sulfate was examined (FIG. 6D). Copper addition alone resulted in a substantial >3 log CFU/mL decrease in bacterial viability. Apo-Ybt protected copper-treated bacteria almost completely from cytotoxicity, with only a 0.024 log decrease in viable cells compared to wild type ($p=NS$). Addition of pre-formed Cu(II)-Ybt complexes abolished the protective effect, suggesting that an unoccupied copper-binding site on apo-Ybt is required for cytoprotection. In the absence of copper, apo-Ybt alone had a negligible effect on bacterial viability. These results show that copper-binding by exogenous Ybt directly protects bacteria from copper toxicity.

Example 9

Figure 7A:
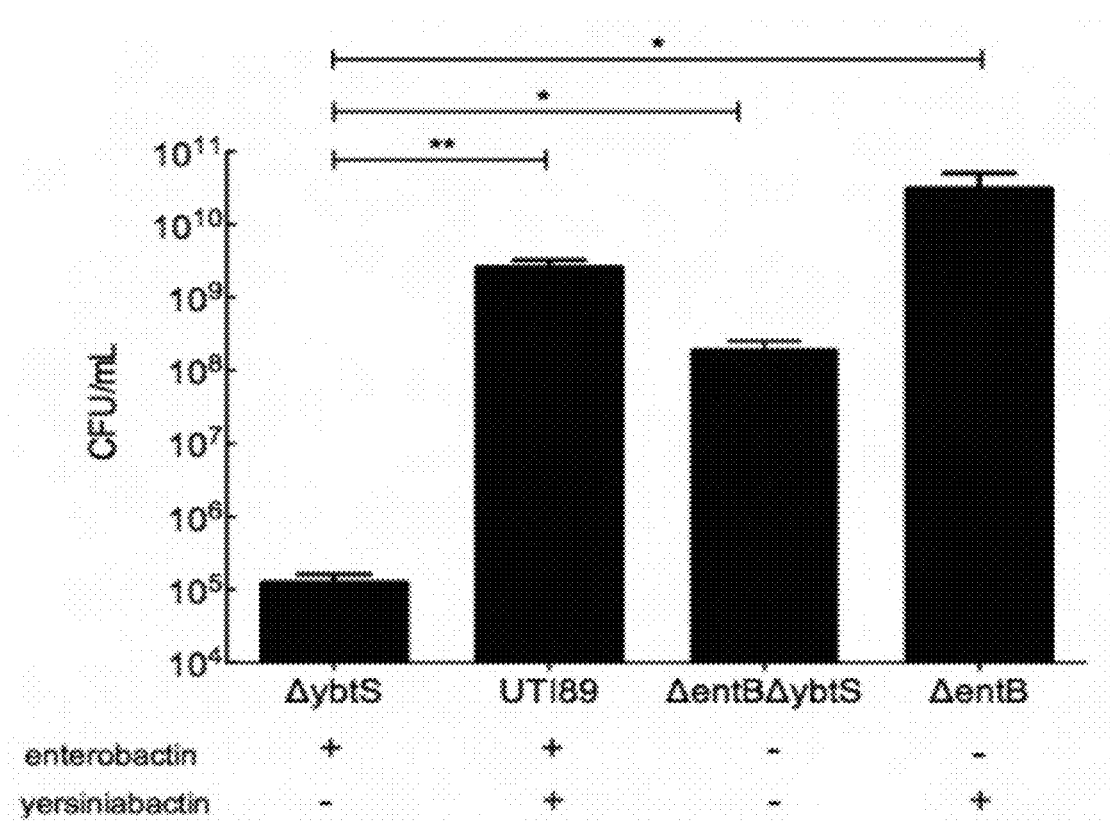
FIG. 7A-D depicts graphs showing that catecholate siderophores and yersiniabactin exert opposing effects on copper cytotoxicity.

Yersiniabactin or Enterobactin-Deficient Mutants Exhibit Opposing Alterations in Copper Sensitivity To determine whether other UPEC siderophores affect copper susceptibility, copper toxicity in an established UT189 mutant with defined siderophore deficiencies was evaluated (FIG. 7A). As noted above, UTI89ΔybtS was more susceptible to copper than the wild type strain (p=0.0021). Conversely, additional deletion of the catecholate biosynthesis gene entB in this strain background (an ΔentBΔybtS double mutant), significantly (p=0.0032) increased survival. The single ΔentB mutant, which expresses Ybt, exhibits a supraphysiological survival benefit in the presence of copper. These results are consistent with previous work describing copper (II) reduction by catechols to more toxic copper (I) ions.

Example 10

Figure 7B:
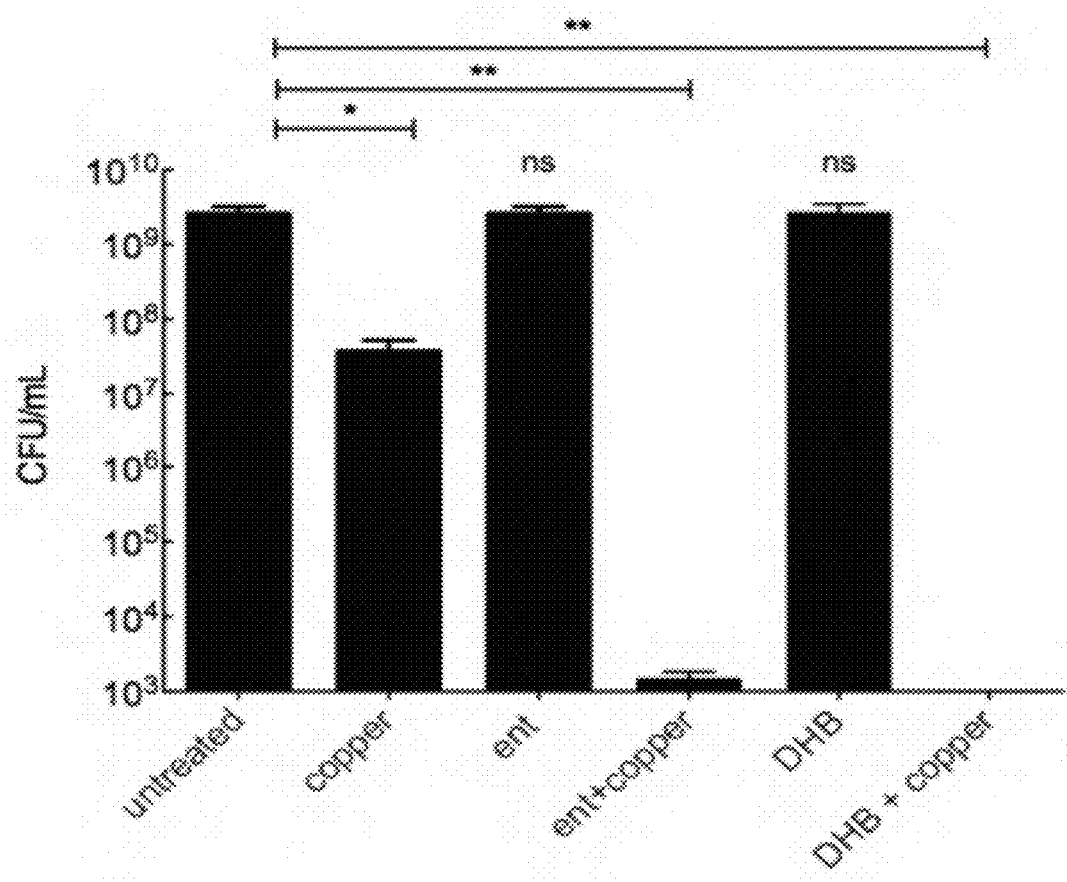

Yersiniabactin-Complexed Copper (II) Resists Catechol-Mediated Copper (I) Formation To test whether the absence of copper reduction by catecholate siderophores explains increased copper resistance in the UTI89ΔentB mutant, we examined copper toxicity to UT189 in the presence and absence of enterobactin or 2,3-dihydroxybenzoic acid (DHB), the catecholate moiety incorporated into enterobactin and salmochelin. Treatment with 10 μM copper (II) sulfate alone caused a 2.5 log reduction of viable colonies. While 20 μM enterobactin or DHB alone had a minimal effect, their addition to copper (II) sulfate significantly (p<0.0072 and p<0.0039, respectively) increased copper cytotoxicity, decreasing viable cells to below the level of detection (LOD=20 CFU/mL) (FIG. 7B). These data show that antibacterial synergy between enterobactin and copper (II) is attributable to enterobactin's catecholate groups.

Figure 7C:
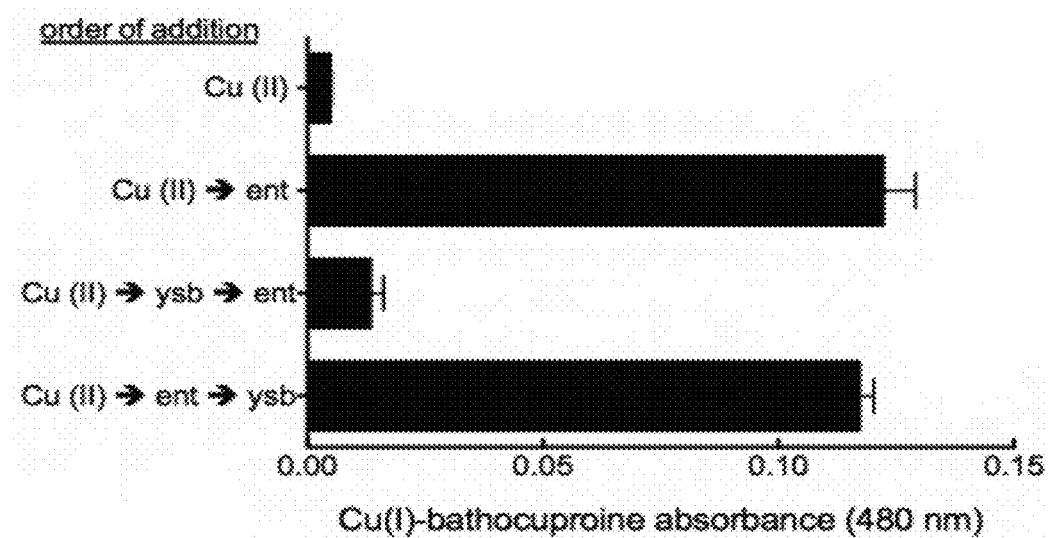
Figure 7D:
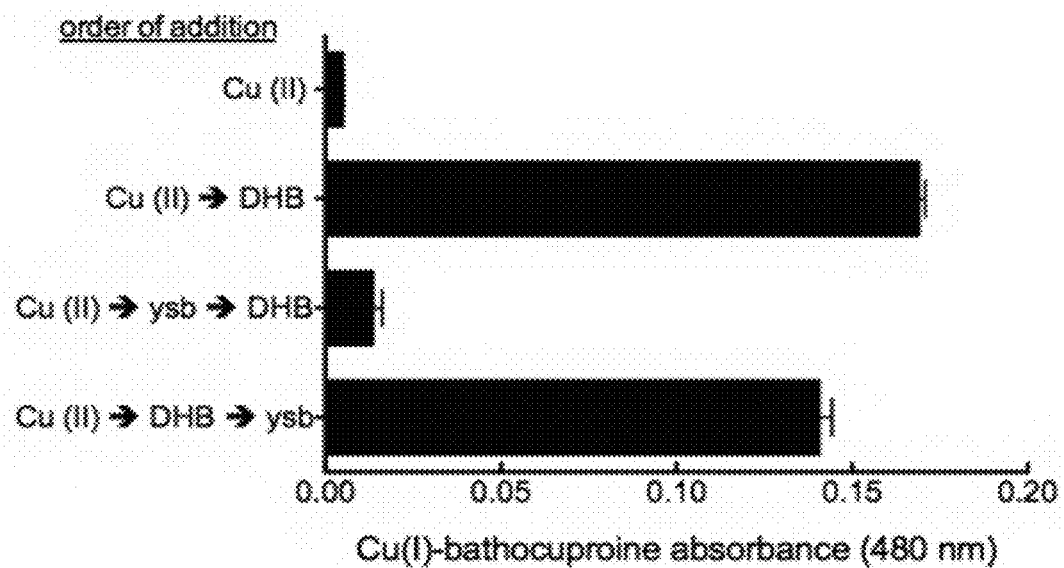

To confirm that enterobactin reduces copper (II) and to determine whether Ybt affects this reaction, copper (I) formation was monitored by purified reagents using a bathocuproine-based spectrophotometric assay (FIG. 7C, D). Addition of either 20 μM enterobactin or DHB to samples containing 17.5 μM copper (II) sulfate resulted in a strong bathocuproine signal corresponding to 84.7% and 93.1% reduction of copper (II) to copper (I), respectively. This signal was almost completely blocked when apo-Ybt was added before enterobactin or DHB. In contrast, changing the order of addition such that enterobactin or DHB were added before apo-Ybt restored the copper (I) signal. Together, these results demonstrate that the catecholate groups of enterobactin and related siderophores reduce copper (II) to more cytotoxic copper (I) and that yersiniabactin protects bacteria not only by sequestering copper (II) but also by inhibiting its catecholate-mediated reduction.

Discussion for Examples 1-10

Results described in the Examples above demonstrate that yersiniabactin binds copper in vivo and protects uropathogenic E. coli from host-derived copper, whose toxicity is enhanced by co-expressed siderophores. Physiologic relevance of copper binding is demonstrated by direct unbiased chemical detection of Cu(II)-Ybt in tissue and urine from an experimental animal infection model and in urine derived from patients with E. coli urinary tract infection. Furthermore, although yersiniabactin and catecholate siderophores have been previously regarded as redundant iron acquisition molecules, this study shows that they can assume disparate roles in modulating copper chemistry and toxicity at the host-pathogen interface. These results suggest that the chemical biology of pathogenic siderophores extends beyond issues of iron binding and acquisition.

Precedent for microbial copper chelation is found among environmental bacteria. While not a siderophore, methanobactin serves an analogous function by binding Cu(I) to satisfy a high nutritional copper requirement driven by synthesis of particulate methane monooxygenase, which accounts for up to 20% of methanotrophic bacterial proteins. The algal hydroxamate siderophore schizokinen may weakly bind Cu(II), with differing effects on copper toxicity to environmental bacteria. Although data in these Examples are consistent with protective copper sequestration as a yersiniabactin function, yersiniabactin could benefit bacteria by obtaining copper as a nutritional source under other circumstances. Yersiniabactin's ability to bind copper during infection may thus derive from an ancestral function or reflect an example of convergent chemical evolution.

Although copper resistance proteins have been described in a wide variety of bacteria, it is unclear if copper resistance represents a virulence-associated adaptation. This question is readily addressed in E. coli, where disease-associated strains exhibit evidence of multiple virulence-associated adaptations. By demonstrating enhanced copper-resistance among disease-associated isolates, this study suggests an important role for copper ions as an antimicrobial defense in human UTI pathogenesis. A role for copper-based immune defenses is further supported by observations of infection-associated increases in copper and use of copper transporters by phagocytic cells to kill internalized bacteria. It is possible that disease-associated isolates without high level copper resistance (4/14 isolates in the present examples) are indicative of patients with subtle differences in pathophysiology or copper-based antimicrobial responses (FIG. 6A). Regardless, the sum of bacteriologic and bioanalytic findings suggests a role for host-derived copper as a virulence-associated selection factor among uropathogenic E. coli.

While catechols are excellent iron-binding functional groups, their ability to directly reduce cupric ions provides a chemical rationale for acquisition of non-catecholate siderophores by bacterial pathogens. Copper (II) is significantly more bactericidal when reduced to its copper (I) valence, which has been attributed to an improved ability of copper (I) to generate reactive oxygen species or to freely penetrate bacterial membranes and inactivate intracellular iron-sulfur clusters. Thus, yersiniabactin's ability to prevent copper (II) reduction and intracellular penetration may additionally protect pathogenic bacteria during infection. Targeting yersiniabactin biosynthesis or the strains that perform this may thus be a useful therapeutic approach. Although it is unclear which yersiniabactin coordination sites facilitate copper binding, it is notable that this molecule contains three nitrogenous heterocycles (thiazolines/thiazolidine), reminiscent of imidazole-rich copper coordination sites in ceruloplasmin and the nitrogen heterocycles in methanobactin. Similar structural features in other siderophores and microbial products may facilitate similar copper-binding functions.

Siderophore profiling by mass spectrometric methods has yielded important insights into the pathogenicity of E. coli and other important pathogens. To date, neither pathogenic siderophore secretion nor in vivo metal ion selectivity of these siderophores have been directly observed and quantified. This work shows how tandem mass spectrometry, together with an understanding of gas phase ion chemistry, can also identify metal binding interactions of these diverse molecules. Its notable sensitivity also permits use of LC-MS/MS to directly interrogate in vivo metal binding rather than relying solely upon attempts to simulate in vitro the complex metal availabilities at sites of infection.

Bacterial pathogens have adapted to a shifting array of evolutionary challenges by secreting a chemically diverse range of secondary compounds and proteins. Yersiniabactin may be one of many multifunctional, virulence-associated metal binders secreted by pathogenic bacteria. In future studies, similar binding interactions could be discovered and validated for other important biomolecules or other secondary compounds using an analogous chemical biology approach.

Materials and Methods for Examples 1-10

Bacterial Strains, Cultivation and Deletion Strain Construction

Urinary and rectal isolates are from a previously described collection. Briefly, distinct, coexisting strains were identified by pulsed-field gel electrophoresis (PFGE) from a longitudinal patient study. Strains were not considered to be "rectal" if they were isolated from a urinary source at any time during the study.

UT189, a well characterized and fully sequenced uropathogenic E. coli clinical isolate, was used as the prototypic pathogen in this study. UT189 mutant strains used in the Examples are listed in Table 1. Bacterial cultures were grown from a single colony in Difco™ Luria-Bertani broth, Miller (LB) (BD, Franklin Lakes, N.J.) for three hours and subsequently diluted 1:100 into M63 medium supplemented with 0.2% glycerol and 10 mg/mL niacin (Sigma). Bacterial cultures were incubated for 18 hours at 37° C. in a rotary shaker.

TABLE 1

UTI89 mutant strains used in this study

| Strain | Gene function | Reference |
| --- | --- | --- |
| UTI89ΔybtS | salicylate synthase, yersiniabactin biosynthesis | Henderson et al. 2009, PLoS Pathog 5, e1000305 |
| UTI89ΔentB | isochorismate lyase, catecholate siderophore (enterobactin/salmochelin) biosynthesis | Henderson et al. 2009, PLoS Pathog 5, e1000305 |
| UTI89ΔiroA | salmochelin biosynthesis, transport, catabolism | Henderson et al. 2009, PLoS Pathog 5, e1000305 |
| UTI89ΔentBΔybtS | salicylate synthase, isochorismate lyase, total mutant for yersiniabactin, enterobactin and salmochelin biosynthesis | Henderson et al. 2009, PLoS Pathog 5, e1000305 |

Deletion Strain Construction:

In-frame deletions in UT189 were made using the red recombinase method, as previously described, using pKD4 or pKD13 as a template. To confirm the appropriate deletions, PCR was performed with flanking primers. Antibiotic resistance insertions were removed by transforming the mutant strains with pCP20 expressing the FLP recombinase.

Figure 8A:
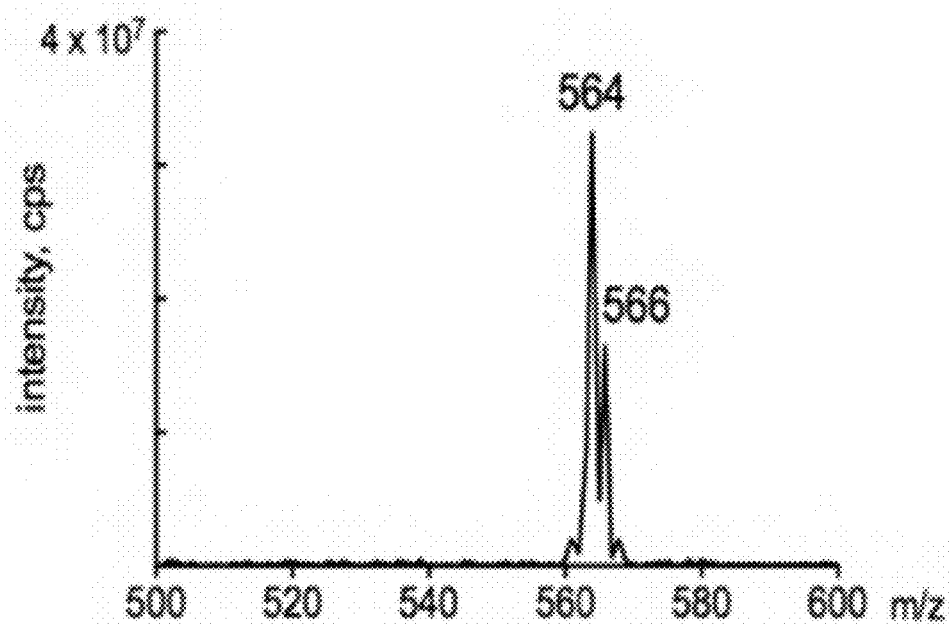
FIG. 8A-B depicts graphs showing structural confirmation of copper (II)-yersiniabactin complexes by isotope labeling. $^{13}C$-labeled internal standard was treated with 3.0 mM copper (II) sulfate and purified over a preparative C18 column.
Figure 8B:
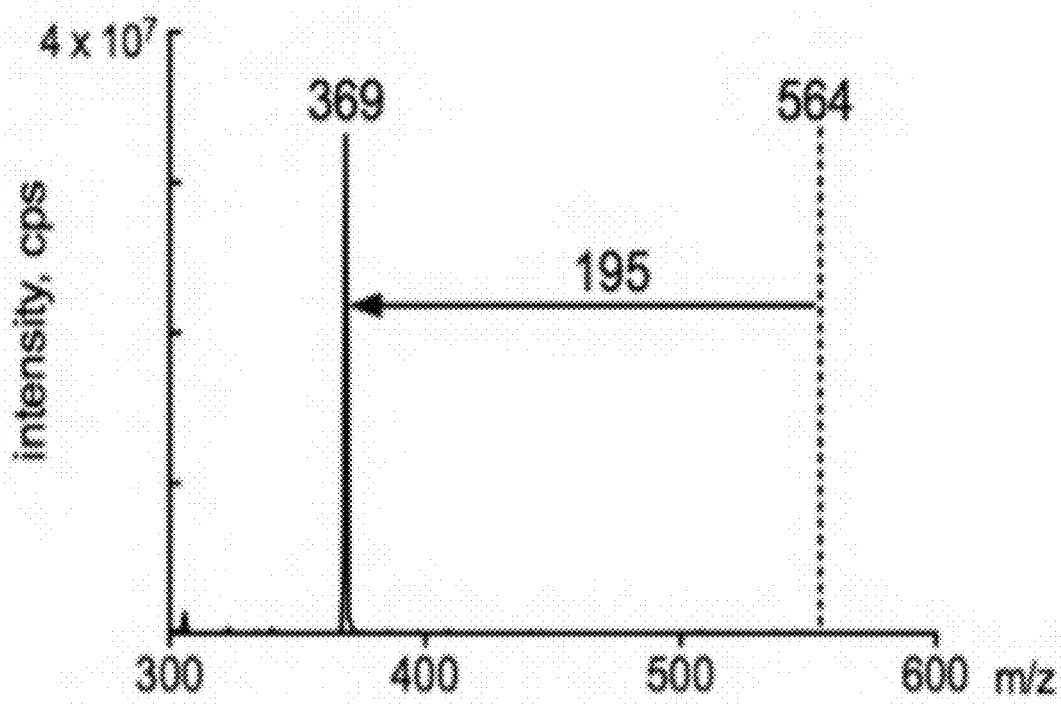
Figure 9A:
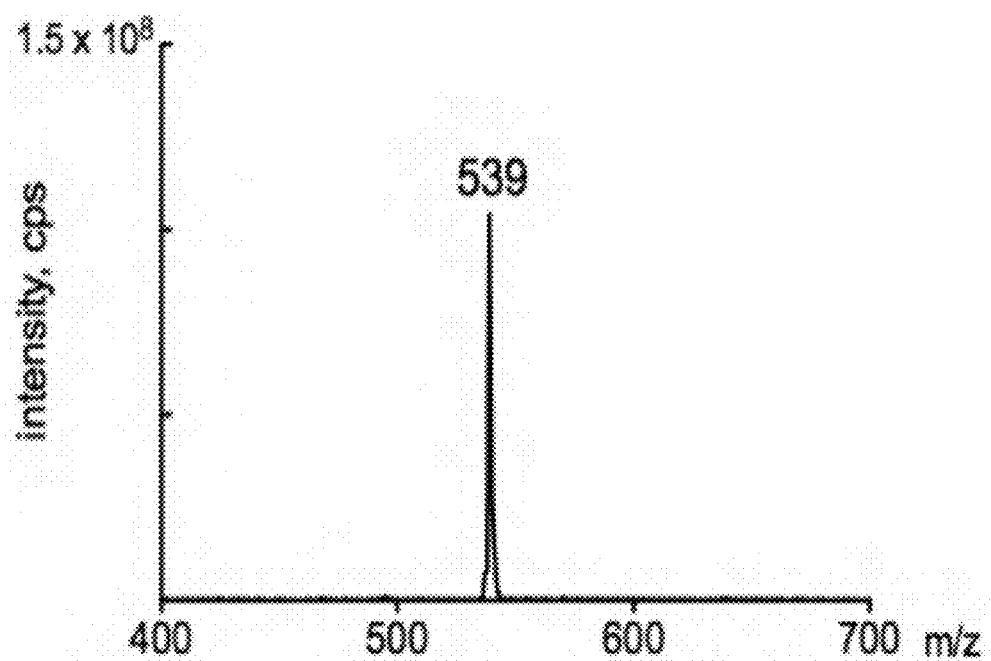
FIG. 9A-B depicts graphs showing preparation of deuterated yersiniabactin. $d_4$-ferric-yersiniabactin was produced by chemically complementing the salicylate synthase-deficient mutant UTI89ΔybtS with 50 μM $d_6$-salicylate during growth in M63 minimal medium containing 0.2% unlabeled glycerol.
Figure 9B:
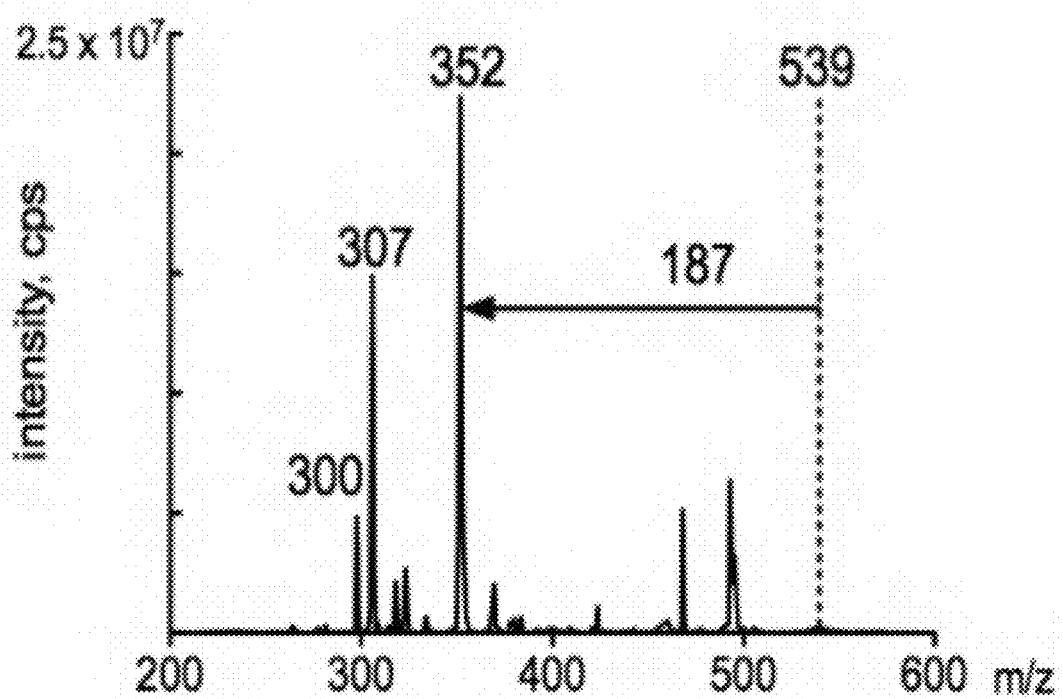

$^{13}$C and Deuterated Internal Standard Preparation:

$^{13}C_{21}$-yersiniabactin was produced by growing the siderophore overproducer UTI89Δfur as previously described. The isotope labeled supernatant was harvested by centrifugation and confirmed by LC-MS detection of $^{13}C_{21}$-ferric yersiniabactin at m/z 556 (FIG. 8). $^{13}C_{21}$-ferric yersiniabactin and $^{13}C_{21}$-cupric yersiniabactin were prepared by treating equal volumes of the labeled supernatant with 5 mM ferric chloride or 5 mM copper sulfate, respectively. Solutions were centrifuged in 15 mL falcon tubes at 6,000 rpm for 10 minutes. The supernatant from these metal treated samples was then subjected to preparative chromatography and eluted with 100% methanol. $d_4$-ferric-yersiniabactin was produced by chemically complementing the salicylate synthase-deficient mutant UTI89ΔybtS during growth in M63 minimal medium supplemented with 50 μM $d_6$-salicylate and 0.2% unlabeled glycerol. The isotope-labeled supernatant was harvested by centrifugation and confirmed by LC-MS detection of $d_4$-ferricyersiniabactin at m/z 539 (FIG. 9). The m/z 539 MS/MS product ion spectrum of this ion retained the 187 amu neutral loss as expected for deuterium incorporation in the yersiniabactin phenyl ring.

Yersiniabactin Purification:

Apo-yersiniabactin was purified from UTI89ΔentB culture supernatants, which lack enterobactin or salmochelin. Metal complexes of yersiniabactin were generated by adding 1.0 M ferric chloride or copper sulfate to UTI89ΔentB cell culture supernatants to a final concentration of 5 mM. Metal-treated supernatants were incubated for 15 minutes at room temperature and centrifuged for 2 minutes at 14,000 rpm. The supernatant was then applied to a conditioned preparative reverse phase column (Waters Sep-Pak C18 cartridges), washed with 2 mL of 20% methanol and eluted with 1 mL of 80% methanol. A centrifugal evaporator was used to concentrate the eluate. Samples were resuspended in 20% methanol and further purified by high-performance liquid chromatography. Samples were applied to a Resource™ 1 mL RPC column (GE Healthcare). The gradient used was as follows: Solvent A (100% deionized water) was held constant at 98% and solvent B (100% methanol) was held constant at 2% for 2 minutes, followed by a linear gradient where solvent B was increased to 100% over 20 minutes and then held constant at 100% for 2 minutes. Eluted samples were subsequently concentrated in a centrifugal evaporator and resuspended in 100 μL deionized water. Following mass spectrometric confirmation, apo-yersiniabactin concentration was determined spectrophotometrically following conversion to ferric-yersiniabactin ($\epsilon_{385}$=2,884 $M^{-1}$ $cm^{-1}$) with 5 mM ferric chloride.

Figure 10:
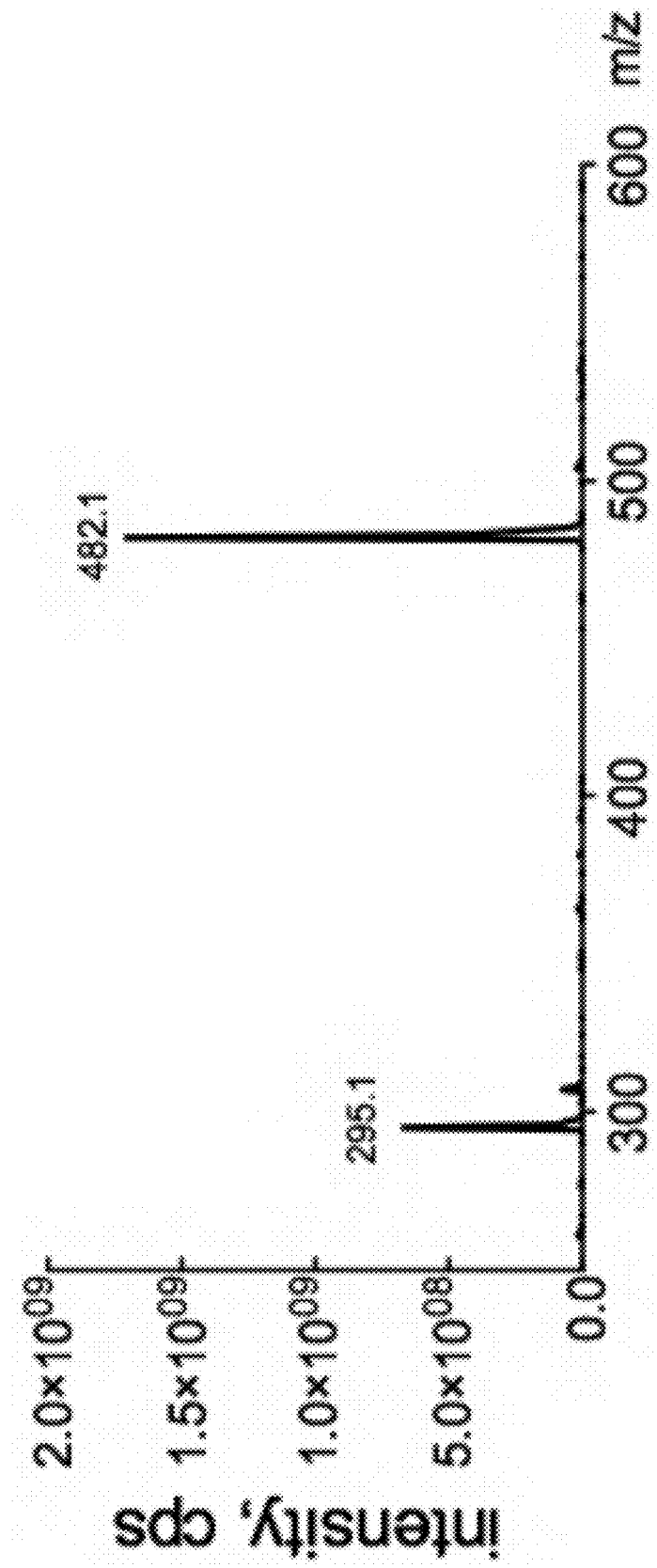
FIG. 10 depicts the mass spectrum of apo-yersiniabactin. Depicted is the positive ESI mass spectrum of a sample from the apo-yersiniabactin preparation used in this study. The predicted $[M+H]^+$ molecular ion at 482 m/z units is evident, along with the $[M+H-187]^+$ source decay fragment at m/z 295.

Liquid Chromatography-Mass Spectrometry:

LC-MS analyses were conducted using a Shimadzu UFLC-equipped AB-Sciex 4000 QTrap operated in positive ion mode using the Turbo V ESI ion source and a Thermo LCQ Deca. The QTrap samples were injected onto a Fused-core phenylhexyl column (100×2 mm, 2.7 μm particle, Ascentis Express, Supelco) with a flow rate of 0.4 mL/min. The gradient used was as follows: Solvent A (0.1% formic acid) was held constant at 98% and solvent B (100% acetonitrile in 0.1% formic acid) was held constant at 2% for 2 minutes, solvent B was increased to 65% by 10 minutes and then to 98% by 12 minutes. The ion spray voltage was set to 5 kV. The heater temperature was 500° C. The declustering potential, nebulizer gas (01), auxiliary gas (G2) and collision energy were set at 110, 40, 35 and 35V, respectively. In vivo Cu(II)-Ybt quantification was carried out in the MRM mode using $^{13}$C-labeled siderophore standards with previously identified CID fragmentations. Cu(II)-Ybt/Fe(III)-Ybt ratio determinations were made by calibrating with standard curves conducted in 1×PBS buffer for in vitro or human urine for in vivo determinations (FIG. 10).

Liquid Chromatography-Constant Neutral Loss (LC-CNL) Scan Analysis:

The UFLC-4000 QTrap was used with the chromatography and ion source settings described above to identify compounds with a common neutral fragment loss of 187 m/z units. The collision energy was set to 35 V and the first mass analyzer (Q1) was set to scan from m/z 200 to 700 amu while the second mass analyzer (Q3) simultaneously scanned at 187 m/z units less than Q1. Sensitivity was maximized by selecting the low-resolution (2 mass unit window, 0.7 FWHH) setting. In this manner, only ions exhibiting a neutral loss of 187 mass units were detected. As $d_4$-ferric-yersiniabactin retained the 187 amu neutral loss, it was used as an internal standard in this analysis.

Human Specimen Collection:

Study protocols were approved by the Institutional Review Board of the University of Washington. All patients provided written informed consent for the collection of samples and subsequent analysis. Clean-catch midstream urine specimens were obtained from female patients at the University of Washington, Seattle, Wash. with acute uncomplicated cystitis using previously described symptoms of dysuria, urinary frequency, or urinary urgency with a concentration of uropathogens in the urine of $z\ 1 \times 10^2$ colony-forming units (CFU/mL). One-tenth volume of Sigma FAST protease inhibitor solution (Sigma, St. Louis, Mo.) was added to freshly voided urines prior to clinical centrifugation to remove cellular material and the supernatant was frozen at −80 C. Uropathogens in midstream urine were identified using standard methods. *E. coli* UTI urine specimens and pathogen isolates with urine white blood cell count ≥350 collected between Jan. 6, 2010 and Nov. 15, 2010 were selected for analysis.

Mouse Infections:

Six- to seven-week old female C3H/HeN mice obtained from Harlan Sprague Dawley, Inc. (Indianapolis, Ind.) were infected with $10^7$ CFU/mL UT189 or PBS control as described. Murine urine samples were collected on the day of tissue harvest. Bladders were aseptically harvested at the indicated time point and homogenized in 1 mL PBS. CFU determination of viable bacteria in homogenates was conducted as described.

Biological Specimen Preparation:

For the purposes of LC-CNL scans, urine samples from healthy volunteers were collected and pooled in metal-free Nalgene beakers and centrifuged in 50 mL Falcon flasks at 7,000 rpm for 15 minutes at 4° C. Apo-yersiniabactin and deuterated ferric-yersiniabactin internal standard were added to a final concentration of 20 μM to human urine supernatants to identify metal ion binding partners. To measure Cu(II)-Ybt in human urine, as well as murine urine and bladder homogenates, 2.5 μL each of $^{13}C$ cupric- and ferric-internal standard was added to 850 μL of bladder homogenate or 500 μL urine, respectively. Samples were centrifuged at 14,000 rpm for 2 minutes. Yersiniabactin in the supernatant was extracted using preparative C18 chromatography (UCT, Inc., Bristol, Pa.) and eluted in 500 μL 100% methanol. Five microliters of the eluate was analyzed by LC-MS/MS to determine Cu(II)-Ybt levels.

Copper Mediated Cytotoxicity Assay:

Following overnight growth in 50 mL M63 minimal media, bacterial cultures were washed twice in phosphate buffered saline (PBS, Sigma) and centrifuged at 6,500 rpm. Washed cultures were resuspended in fresh M63 minimal media, and normalized to $10^8$ CFU/mL for subsequent treatment. Normalized cultures were treated with varying concentrations of copper (II) sulfate and test agent in 2 mL reaction volumes in 6-well tissue culture plates. Samples were incubated for 20 hours at 37° C. with shaking. Bacterial viability was reported as the number of colony forming units per milliliter of the reaction volume post-treatment (CFU/mL).

Free Copper (I) Determinations:

Free copper (I) was determined spectrophotometrically using the copper (I) indicator bathocuproine. Briefly, 25 μM bathocuproine, 25 μM apo-yersiniabactin, and 17.5 μM copper (II) sulfate, were used in combination in order-of-addition experiments, as well as alone as controls in PBS. Either 20 μM enterobactin (Sigma) or its catecholate moiety, 2,3-dihydroxybenzoic acid (DHB) were added as bioreductants. Following a 30 minute room temperature incubation, 25 μM bathocuproine was added and copper (I) levels were determined by measuring the visible absorbance at 480 nm of the cuprous-bathocuproine complex. Final concentrations of copper (I) were determined by comparison to a standard curve.

Figure 11A:
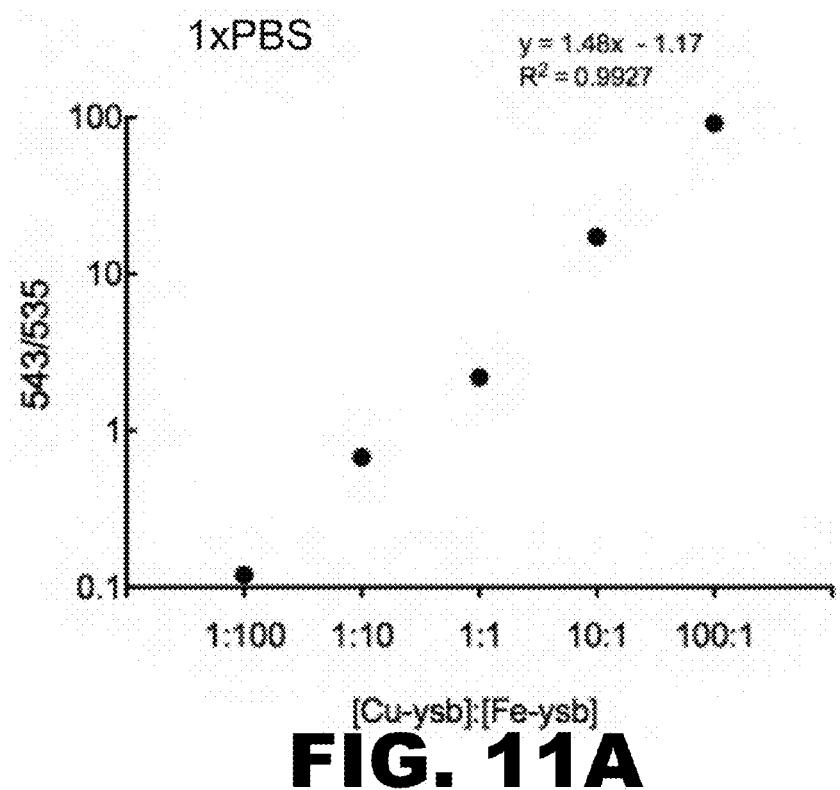
FIG. 11A-B depicts graphs showing the calibration curves for the determination of Cu(II)-Ybt to Fe(III)-Ybt molar ratios. Standard curves used for in vitro analysis were performed in phosphate buffered saline (PBS, FIG. 11A). Curves used for in vivo analyses were performed in human urine (FIG. 11B). The Y axes refer to the LCMS/MS peak area ratios derived from the Cu(II)-Ybt precursor ion at 543 m/z units and the Fe(III)-Ybt precursor ion at 535 m/z units. Both curves exhibited broad linear responses and slopes near unity.
Figure 11B:
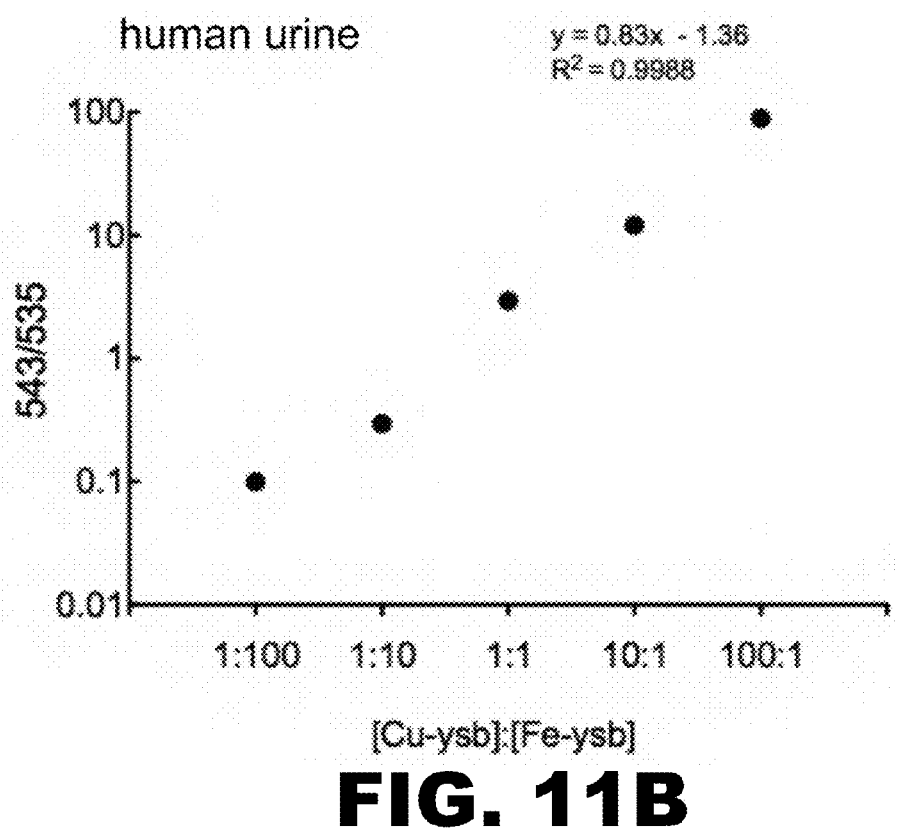

Determination of Cu(II)-Ybt to Fe(III)-Ybt Molar Ratios:

Cu(II)-Ybt to Fe(III)-Ybt molar ratios were determined using the calibration curves shown in FIG. 11.

Statistical Analyses:

Statistics and graphs were generated using Graph Pad Prism 4 (Graph Pad Software, La Jolla, Calif.). For group-wise comparisons of siderophore production, the Mann-Whitney U Test was performed. The t-test was used to compare urinary versus rectal strain growth as well as growth differences between paired strains. Analyses of paired strain differences in siderophore production were performed using the Wilcoxon signed rank test for significance.

Introduction for Examples 11-16

Several functional studies have demonstrated that infection is accompanied by systemic changes in copper concentration within the host. Radiotracer studies with $^{64}Cu$ have demonstrated that copper accumulates at sites of inflammation and within the exudates of wounds and burns where there exists an abundance of macrophages. Phagocytes such as macrophages represent one of the first lines of defense against invading microbial pathogens, and rely on high local concentrations of copper (II) for their bactericidal action. The debilitating effects of micromolar copper stress have been attributed to the de-regulation of iron homeostasis by the disruption of Fe—S clusters in microbial proteins, as well as metal-catalyzed Fenton-type reactions. It is possible that by binding copper within the infection microenvironment, Cu(II)-Ybt complexes fulfill additional unappreciated biochemical roles that have important pathogenic consequences.

In the following examples, a new role for the Cu(II)-Ybt complex is established as a redox-active superoxide dismutase mimic that catalyzes the dismutation of superoxide anions. A physiologic context for this interaction is further established by demonstrating that the yersiniabactin-expressing uropathogen, UT189, modulates the bactericidal activity of RAW264.7 macrophages. Structure-function experiments indicate that a direct interaction between salicylate and a redox-active metal is necessary to maintain the SOD activity of Cu(II)-Ybt complexes in the presence of protein. By time-dependent density-functional theory (TD-DFT) calculations, it is predicted that copper (II) is coordinated in a square planar configuration by contributions from four electron pairs from the yersiniabactin backbone. While cytoplasmic and periplasmic superoxide dismutases have been described in Enterobacteriaceae, this is the first report of a freely diffusible, virulence-associated extracellular SOD mimic. Together, these studies provide new insight into the molecular basis by which copper complexed yersiniabactin protects bacteria from host innate defenses.

Example 11

Figure 12A:
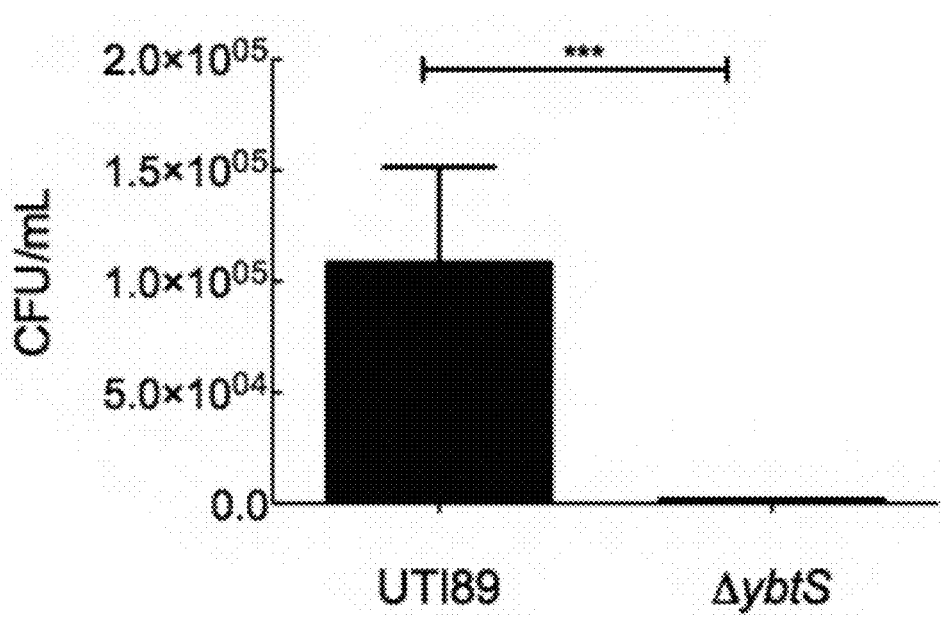
FIG. 12A-B depicts graphs showing yersiniabactin is a determinant of UT189 survival within copper-treated RAW264.7 macrophages. RAW264.7 macrophages were infected with UT189 or the ybtS deficient mutant following treatment (FIG. 12A) with or (FIG. 12B) without 20 μm copper sulfate. After removal of extracellular bacteria, bacterial survival was measured following incubations for 1 hour at 37° C. and expressed as a percentage of initial irternalized E. coli (mean±S.D.; n=3; p<0.0032, Student's t test). UT189 is significantly (p=0.001) more viable than the ybtS deficient mutant only in macrophages that have been treated with copper. This indicates that the expression of yersiniabactin selectively attenuates the copper-dependent bactericidal activity of macrophages. These experiments were conducted in triplicate.
Figure 12B:
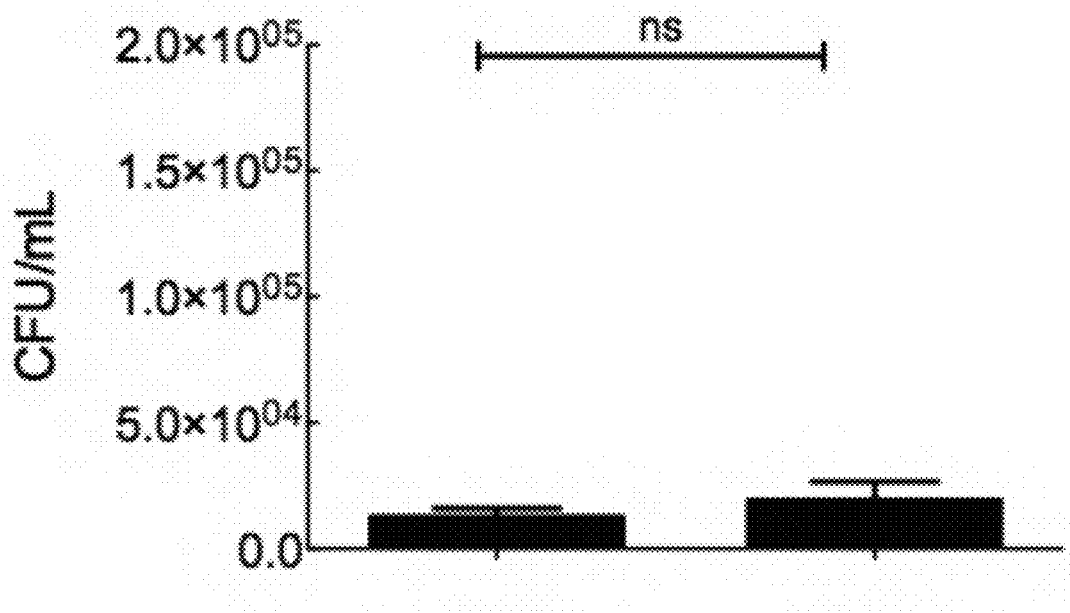

Increased Survival of Wild Type UTI89 in Response to Copper Challenge within RAW264.7 Macrophages To determine whether yersiniabactin modulates the copper-dependent bactericidal activity of macrophages, survival of the yersiniabactin deficient mutant UTI89 ΔybtS was compared to wild type control within RAW264.7 macrophages. RAW264.7 cells were incubated overnight in the presence or absence of 20 μM copper. Following overnight incubation, the macrophages were washed and infected with 1:10 cultures of UTI89 or ΔybtS, and bacterial survival was assessed by the number of colony forming units (CFU/mL) (FIGS. 12A and 12B). UTI89 exhibits significantly (approximately 2 log CFU/mL, p=0.001) greater number of viable colonies within copper treated RAW264.7 cells, compared to the ybtS deficient mutant. In contrast, survival of both UTI89 and the ΔybtS mutant was significantly (p=0.0032) reduced in RAW264.7 cells without copper treatment. The increase in survival of wild type UTI89 relative to the ybtS mutant occurs in a copper dependent manner, indicating that the wild type strain adapts to copper stress while the yersiniabactin deficient strain cannot. These findings support the hypothesis that yersiniabactin modulates the copper-dependent bactericidal activity of macrophages.

Example 12

Figure 13A:
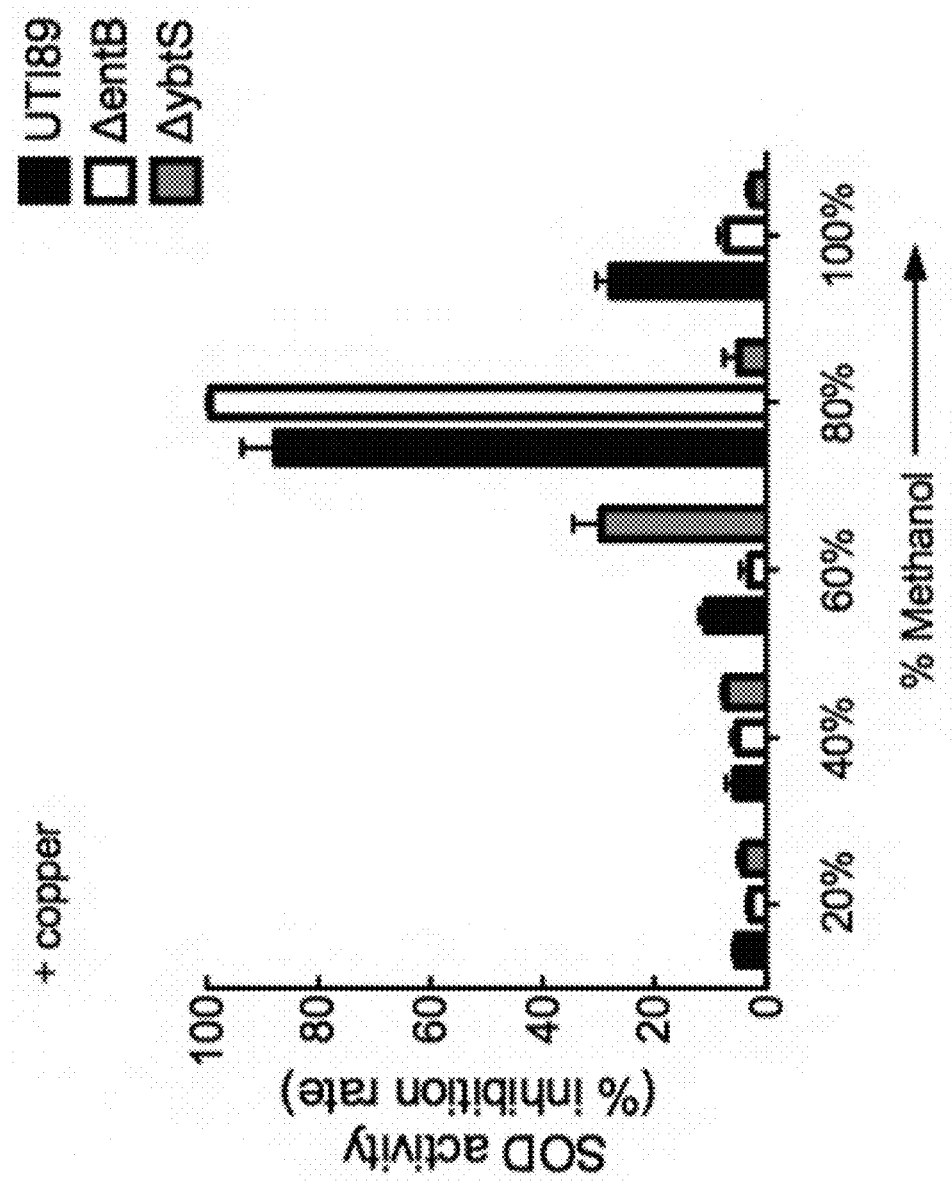
FIG. 13A-B depicts graphs showing superoxide dismutase activity associated with UT189 fractions. Copper treated and untreated culture supernatants of UT189, ΔybtS and ΔentB were subjected to preparative chromatography, and the resulting methanolic fractions were tested for superoxide dismutase (SOD) activity.
Figure 13B:
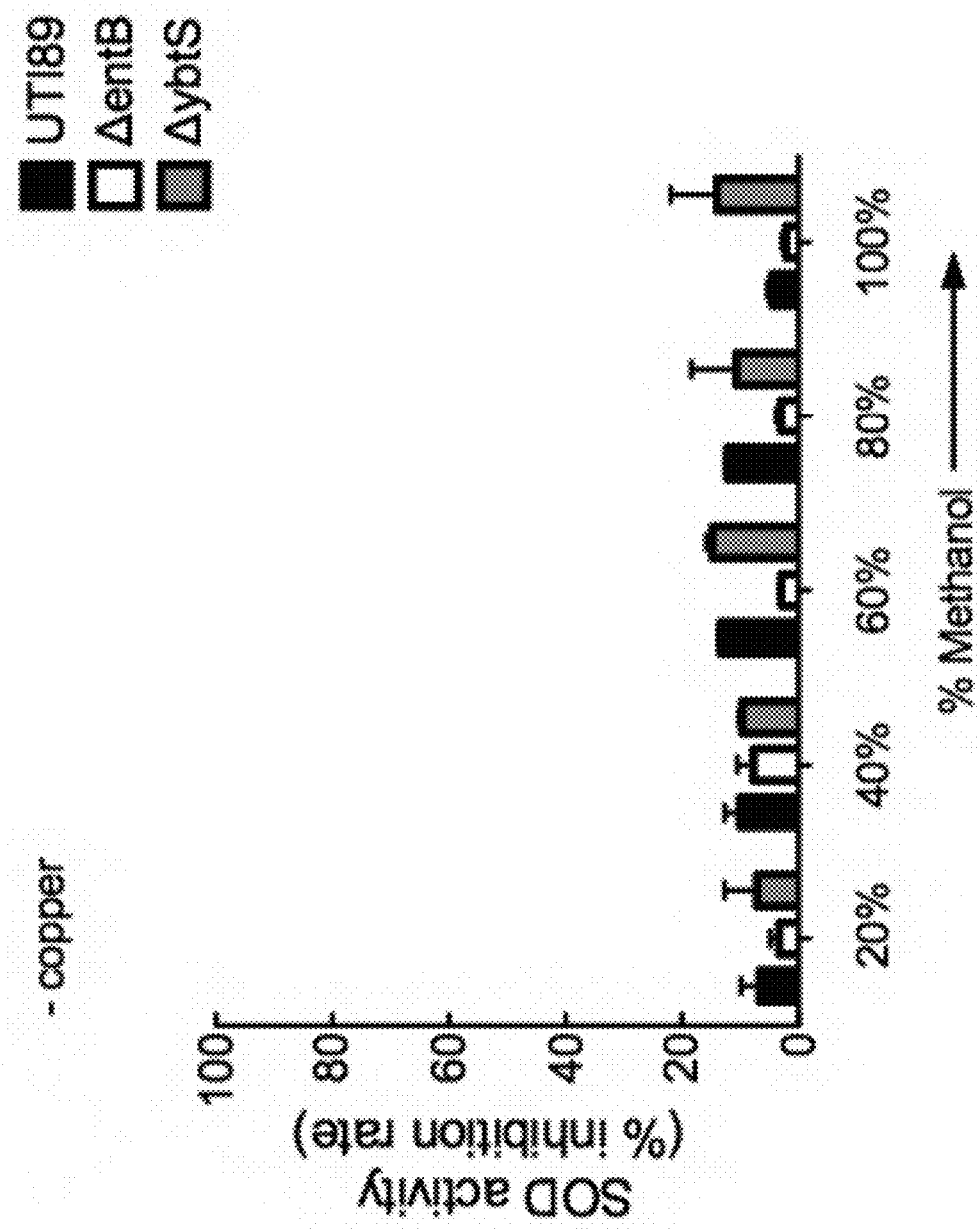

UTI89 Supernatant Reveals Superoxide Dismutase Activity in Fractions Associated with Yersiniabactin It has been demonstrated that superoxide radicals are the predominant oxygen-based radical species that are formed intracellularly by macrophages within the first 30-90 minutes immediately following phagocytosis. To determine whether cultures of UTI89 have the ability to selectively interact with superoxide species in a manner that leads to greater survival in macrophages, these cultures were tested for superoxide dismutase (SOD) activity. Cell cultures of UTI89, ΔybtS and ΔentB (a siderophore mutant that overexpresses yersiniabactin) grown in M63 media were treated with or without 20 μM copper and crudely fractionated using preparative reverse-phase columns. Methanolic extracts were then dried, re-suspended in HPLC grade water and tested for SOD activity (FIGS. 13A and 13B). Copper-treated fractions of UTI89 and the entB deficient mutant demonstrated 87.6% and 99.4% SOD activity in the 80% crude methanolic extract normally associated with yersiniabactin purification. Only 24% superoxide activity was observed in the ΔybtS mutant in the 60% crude methanolic extract. Superoxide dismutase activity was not observed in any supernatants that were not treated with copper. To further confirm whether the SOD activity observed in the crude 80% extract from UTI89 and the entB mutant can be attributed directly to the presence of cupric-yersiniabactin, the crude extracts were purified and concentrated by HPLC. The greatest degree of SOD activity was concentrated in the 80% methanolic extract from UT189 and ΔentB superna- tants (86.5% and 98.3%, respectively). These samples were confirmed as 99% pure cupric-yersiniabactin by LC-MS/MS.

Example 13

Cupric-Yersiniabactin is a Superoxide Dismutase Mimic

Figure 14A:
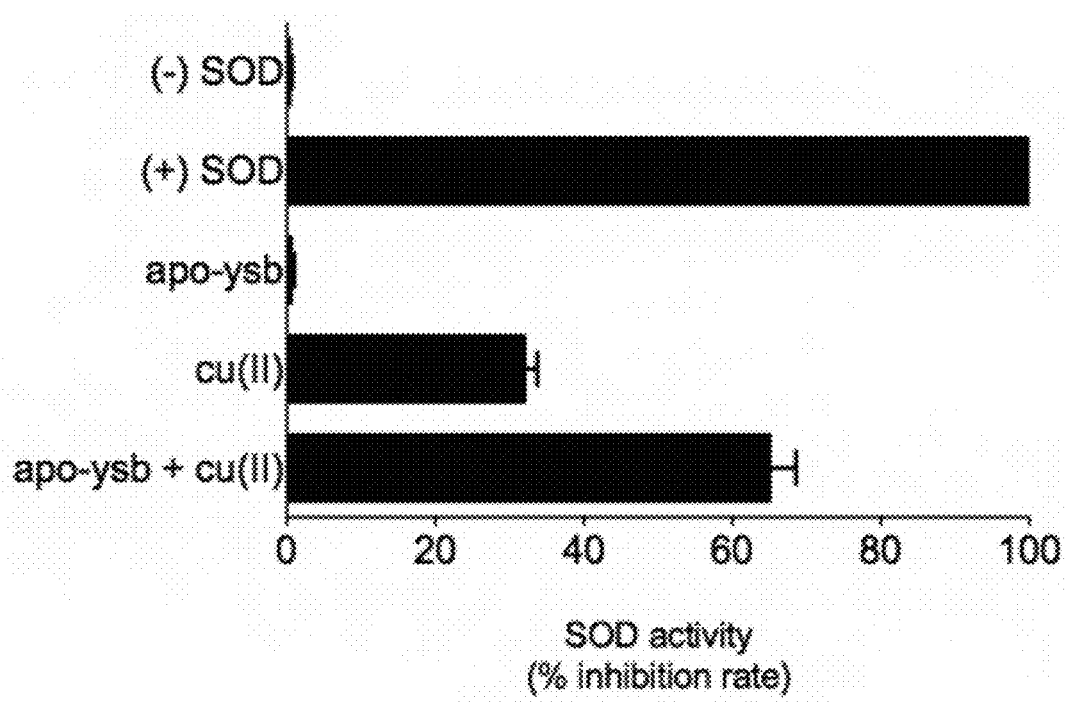
FIG. 14A-D depicts graphs showing cupric yersiniabactin is a superoxide dismutase mimic. Apo- and metal-complexes of yersinabactin were assessed for SOD activity using a WST-formazan based colorimetric assay. Results are reported as a normalized percentage compared to positive controls treated with bovine superoxide dismutase.
Figure 14B:
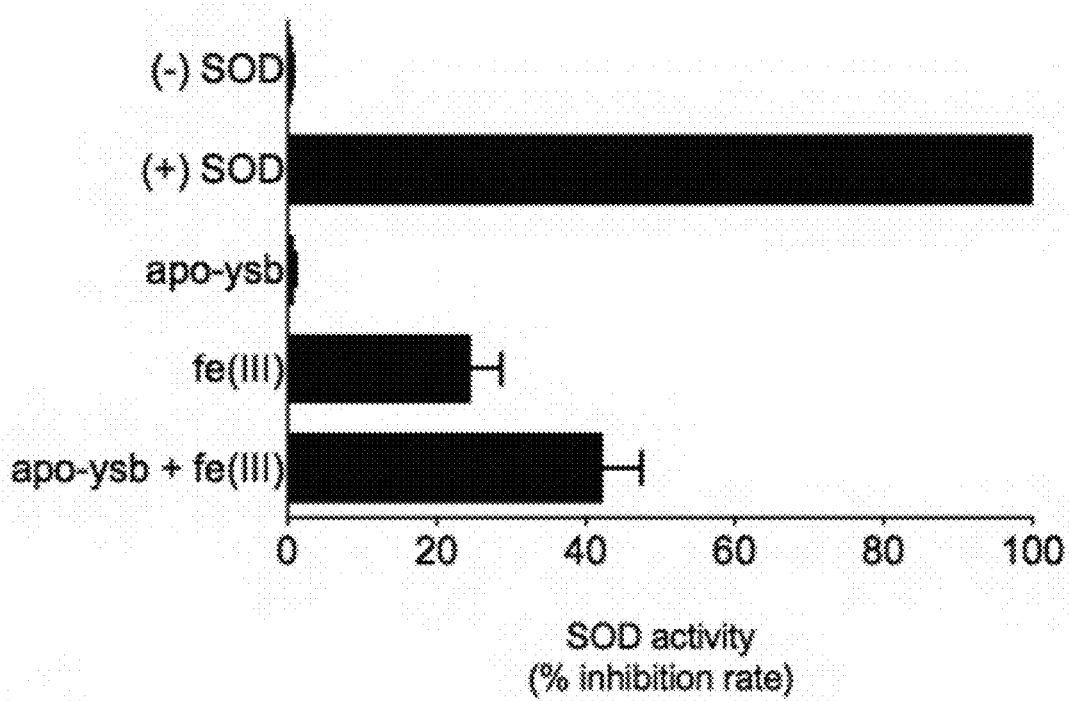
Figure 14C:
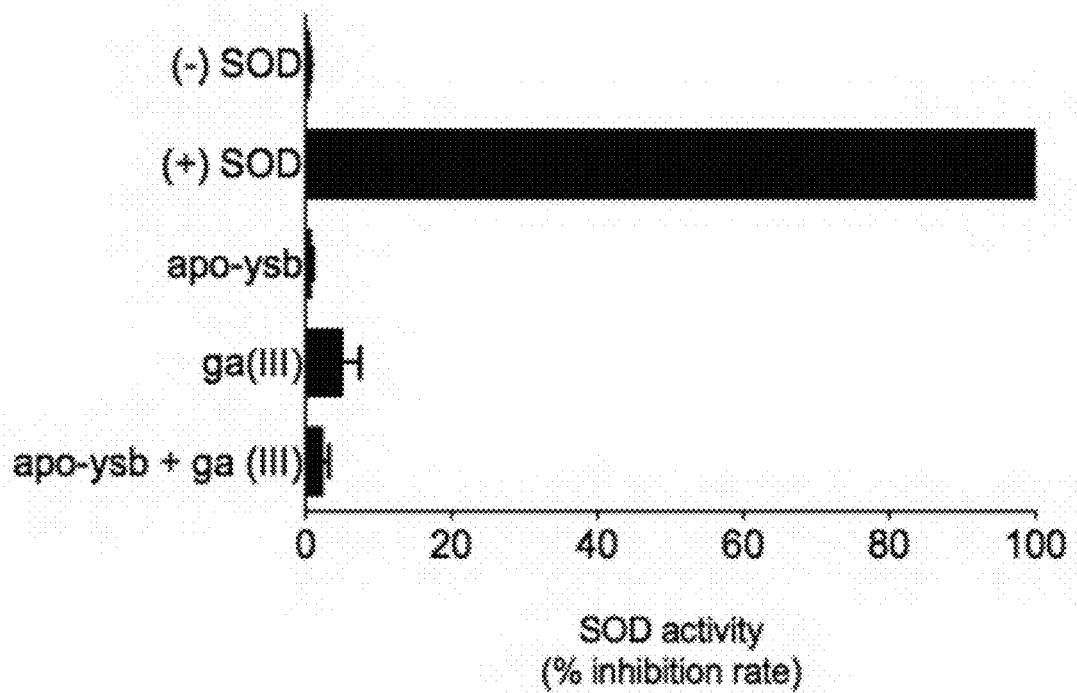

Copper chelation by yersiniabactin has been previously established (see Examples above). Additionally, precedent for superoxide dismutase activity in copper chelators has been established in certain environmental isolates. Superoxide dismutase activity attributed to copper (II)-yersiniabactin was determined directly by means of a xanthine/xanthine oxidase reaction system. In this WST-formazan-based assay, bovine Cu/Zn SOD dismutase completely inhibited superoxide anion formation. The SOD activity of cupric-yersiniabactin, calculated as a percentage inhibition rate, was 63.1% (FIG. 14A). In this system, copper sulfate alone demonstrated an inhibition rate of 33.8%, while apo-yersiniabactin alone did not demonstrate superoxide dismutase activity. To determine whether this phenotype is specific to the redox state of the metal bound to yersiniabactin, iron- and gallium-complexed yersiniabactin samples were generated in similar fashion (FIGS. 14B and 14C). While iron-complexed yersiniabactin complexes demonstrated SOD-like activity, the yersiniabactin complexed with redox inert gallium had an average optical density of 0.782 similar to the negative control, indicating that this activity was specific to the redox state of the metal. Notably, copper sulfate, ferric chloride, gallium nitrate, and apo-yersiniabactin did not demonstrate any superoxide dismutase like activity by themselves. Therefore, the superoxide dismutase activity can be attributed directly to non-inert metal-complexed siderophore itself.

Figure 14D:
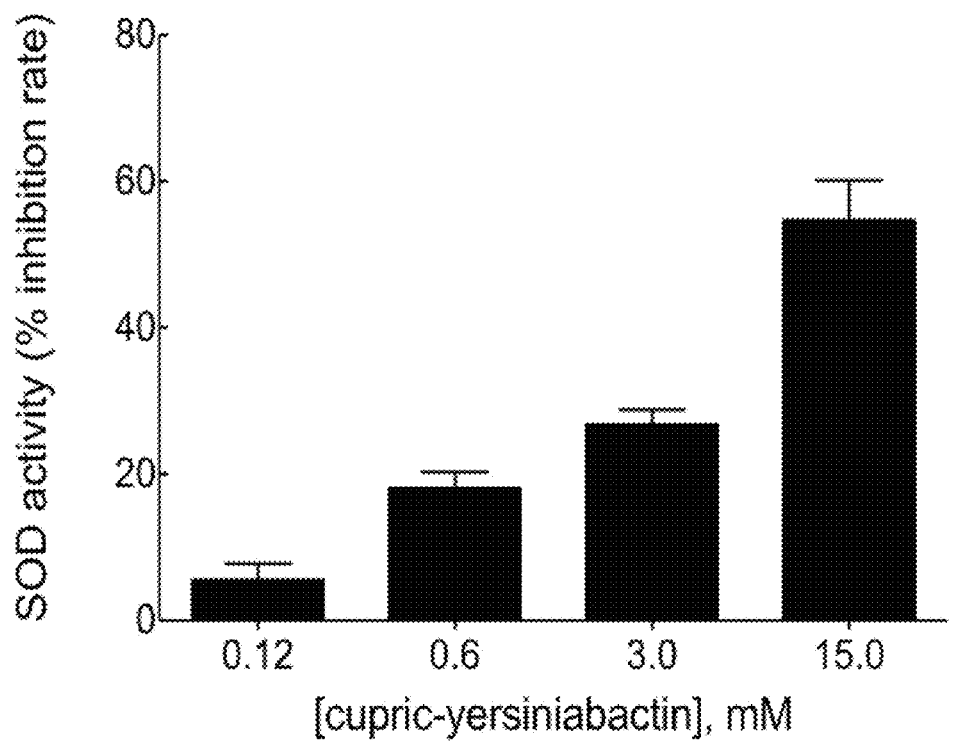

The kinetics of this enzymatic activity were also determined with purified cupric-yersiniabactin complexes (FIG. 14D). For 0.12 mM, 0.6 mM, 3.0 mM and 15.0 mM solutions of cupric-yersiniabactin, the percentage inhibition rates were determined to be 4.6%, 19.8%, 24.3%, and 55.7%, respectively. In order to determine the complex concentration required yielding a 50% ($IC_{50}$) inhibition of the reaction, percentage of inhibition as a function of the logarithm of the metal-complexed siderophore concentration was plotted. These data indicate that cupric-yersiniabactin is a superoxide dismutase mimic, and that the rate of SOD activity is dose dependent.

Example 14

Yersiniabactin Retains Superoxide Dismutase Activity in the Presence of Albumin

Figure 15A:
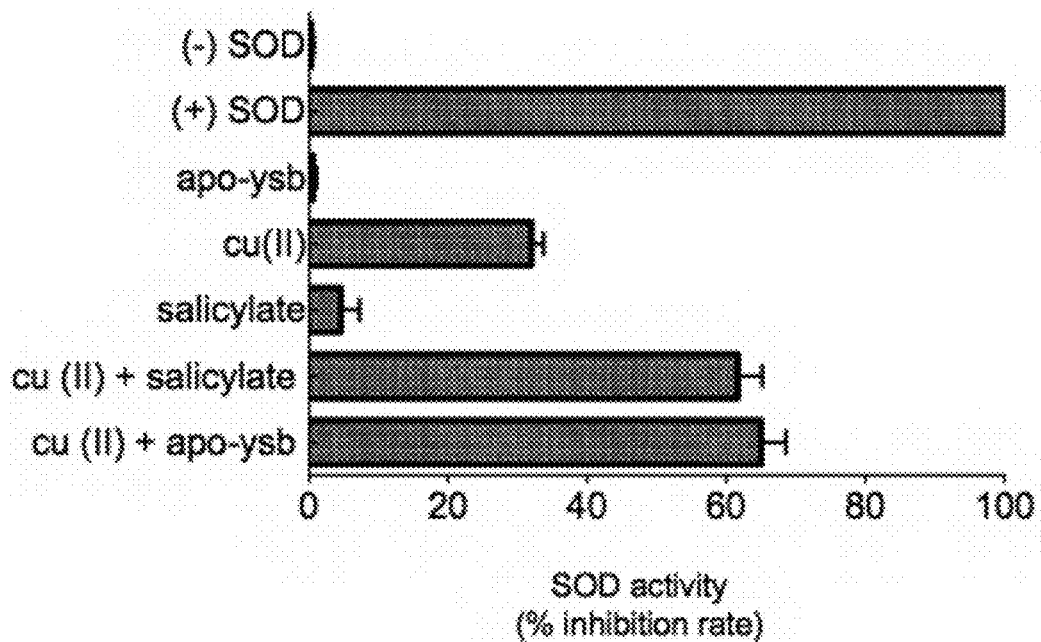
FIG. 15A-B depicts graphs showing SOD activity of cupric-yersiniabactin is selectively retained in the presence of protein.
Figure 15B:
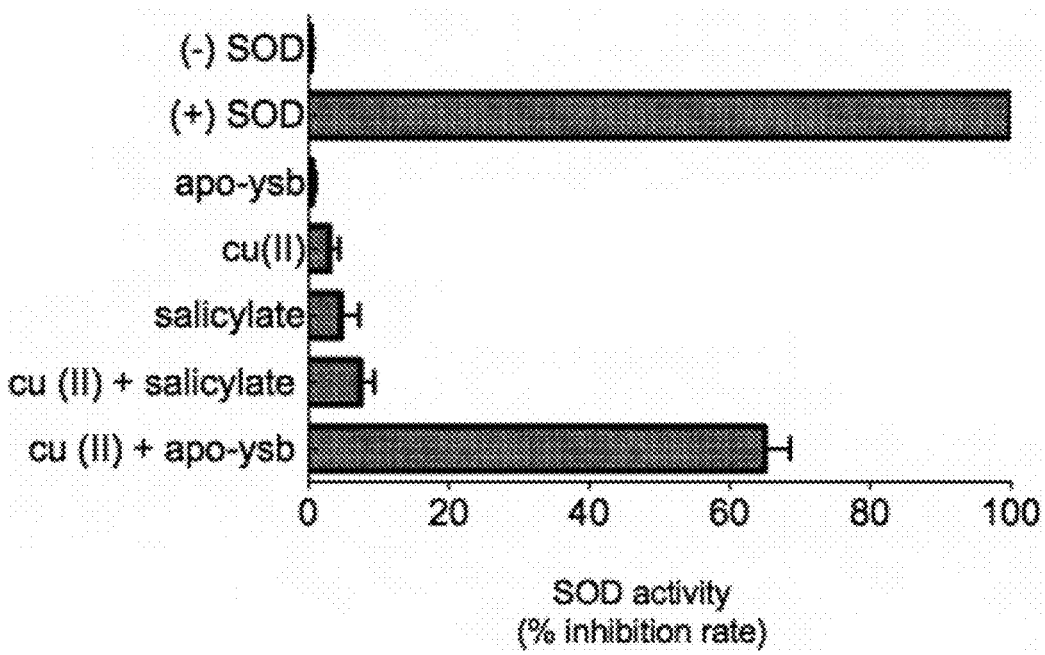

Copper (II) and copper (II)-salicylate complexes demonstrate superoxide dismutase activity, which can be quenched in the presence of low millimolar concentrations of serum albumin. To determine if yersiniabactin retains selective chemical advantage in a physiologic context, the superoxide dismutase activity of cupric-yersiniabactin was determined in the presence of 1.0 mg/mL bovine serum albumin. As previously described, serum albumin suppressed the catalytic activity of copper (II) and that of copper (II)-salicylate complexes, but had no effect on the catalytic activity of the cupric-yersiniabactin complex (FIGS. 15A and 15B). The ability of cupric-yersiniabactin to retain catalytic activity in the presence of albumin indicates that that complex is chemically stable in a biological environment, and thus provides a chemical rationale for its catalytic activity.

Example 15

Figure 16A:
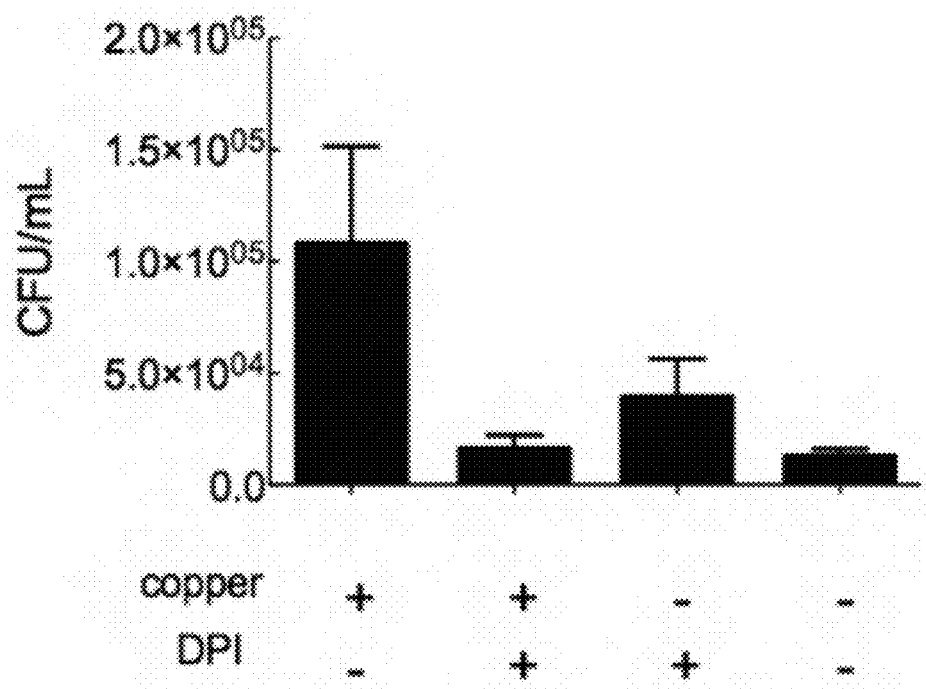
FIG. 16A-C depicts graphs showing cupric yersiniabactin is a superoxide dismutase mimic that protects bacteria during the macrophage respiratory burst. RAW264.7 macrophages were treated with 25 ng/ml diphenyleneiodonium chloride in the presence or absence of 20 μm copper prior to exposure to E. coli.
Figure 16B:
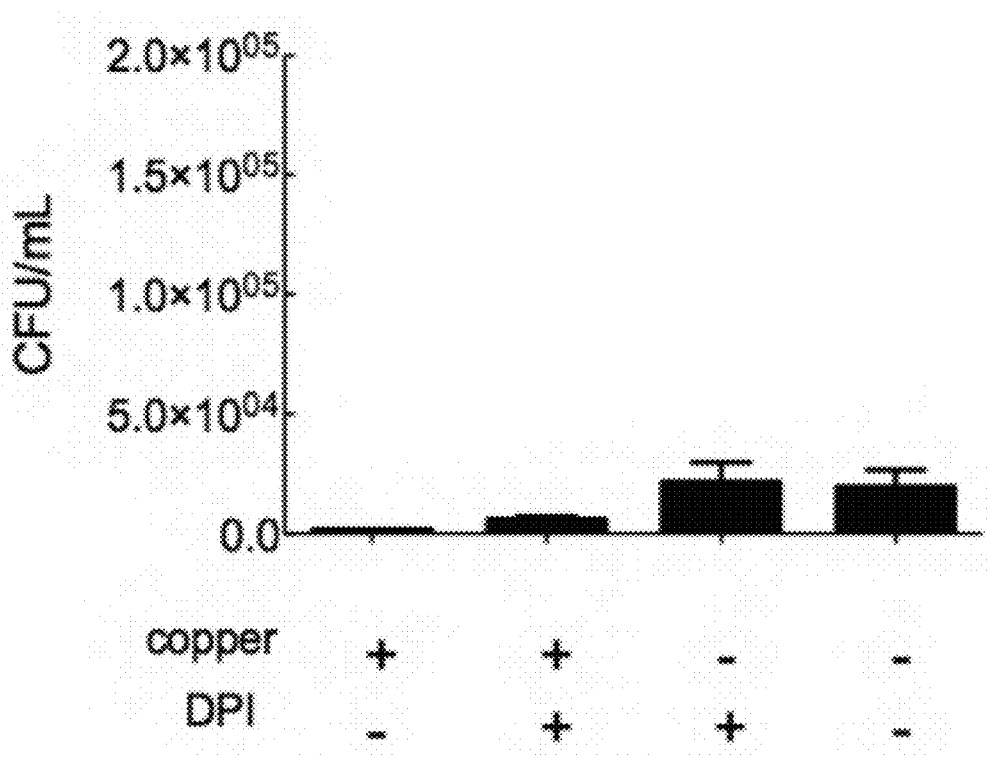
Figure 16C:
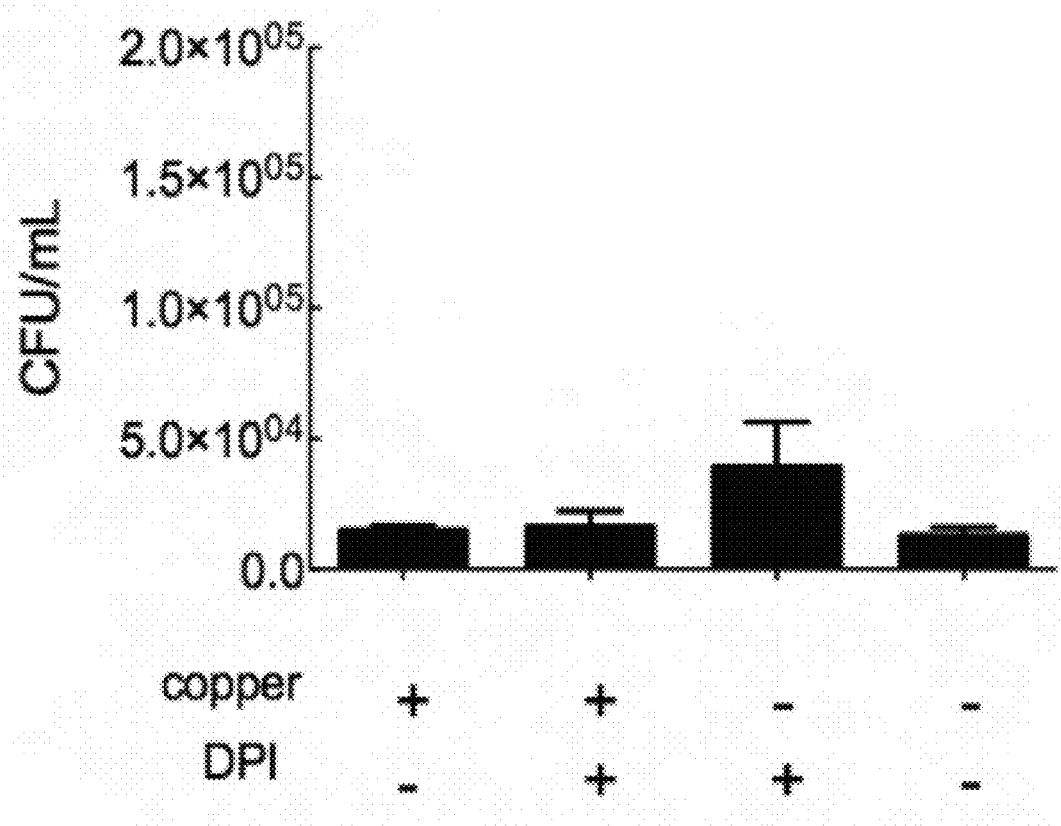
Figure 17:
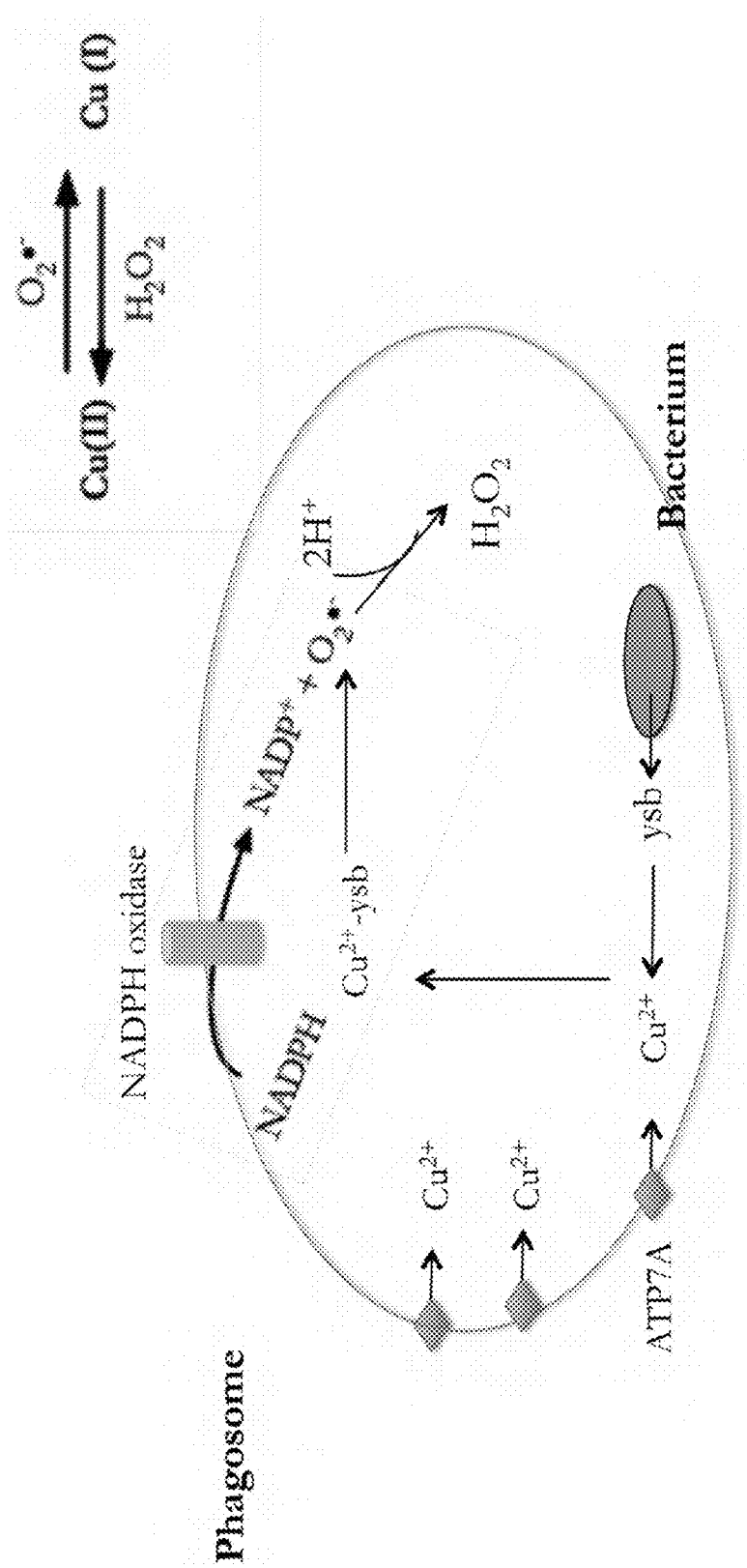
FIG. 17 depicts a model for the interaction of copper (II) with yersiniabactin as a determinant of bacterial persistence within the phagosome. In activated macrophages, there is an upregulation of ATP7A expression and increased intraphagosomal copper levels. Additionally, this compartment relies on the generation of superoxide anion by NADPH oxidase ($.O_2^-$) as its primary bactericidal species. Bacteria secrete yersiniabactin into the macrophage phagosome, which complexes copper (II). Complexes of copper (II) and yersiniabactin demonstrate SOD activity and attenuate the formation and propagation of superoxide species. The interaction of copper (II) with yersiniabactin additionally prevents downstream microbicidal effects due to disruption of Fe—S clusters and generation of hydroxyl radicals via Fenton chemistry.

The Survival Phenotype Relies Upon Innate Production of Oxygen-Dependent Radicals by Macrophages To determine whether the yersiniabactin-mediated protection inside copper-treated macrophages relies on an interaction between cupric-yersiniabactin complexes with superoxide species in macrophages, ROS production by the NADPH oxidase complex was blocked by using 25 mM DPI (FIGS. 16A, 16B, and 16C). As expected, cells treated with DPI decreased oxidative-burst activity to background levels without any gross defect in phagocytosis (data not shown). Macrophages treated with neither DPI nor copper demonstrate a baseline bactericidal activity for both UT189 and ΔybtS. A selective increase in the survival of UT189 occurs only in macrophages treated with copper. Furthermore, comparison of these strains to a K12 strain, MG1655, indicates that the cytoprotective phenotype in copper-treated macrophages is specific to the strain expressing yersiniabactin. Treatment of macrophages with both copper and DPI, or with DPI alone results in reduced survival of wild-type bacteria to the same levels as MG1655 and the ΔybtS deficient mutant, abolishing the selective survival of wild-type cells observed in copper-treated macrophages. These findings indicate that DPI inhibition of the production of superoxide radicals by macrophages leads to a loss of the growth phenotype that is selectively observed in copper-treated macrophages. This suggests that copper(II)-yersiniabactin selectively interacts with, and dismutates superoxide anion in macrophages in vitro (FIG. 17).

Example 16

Figure 18A:
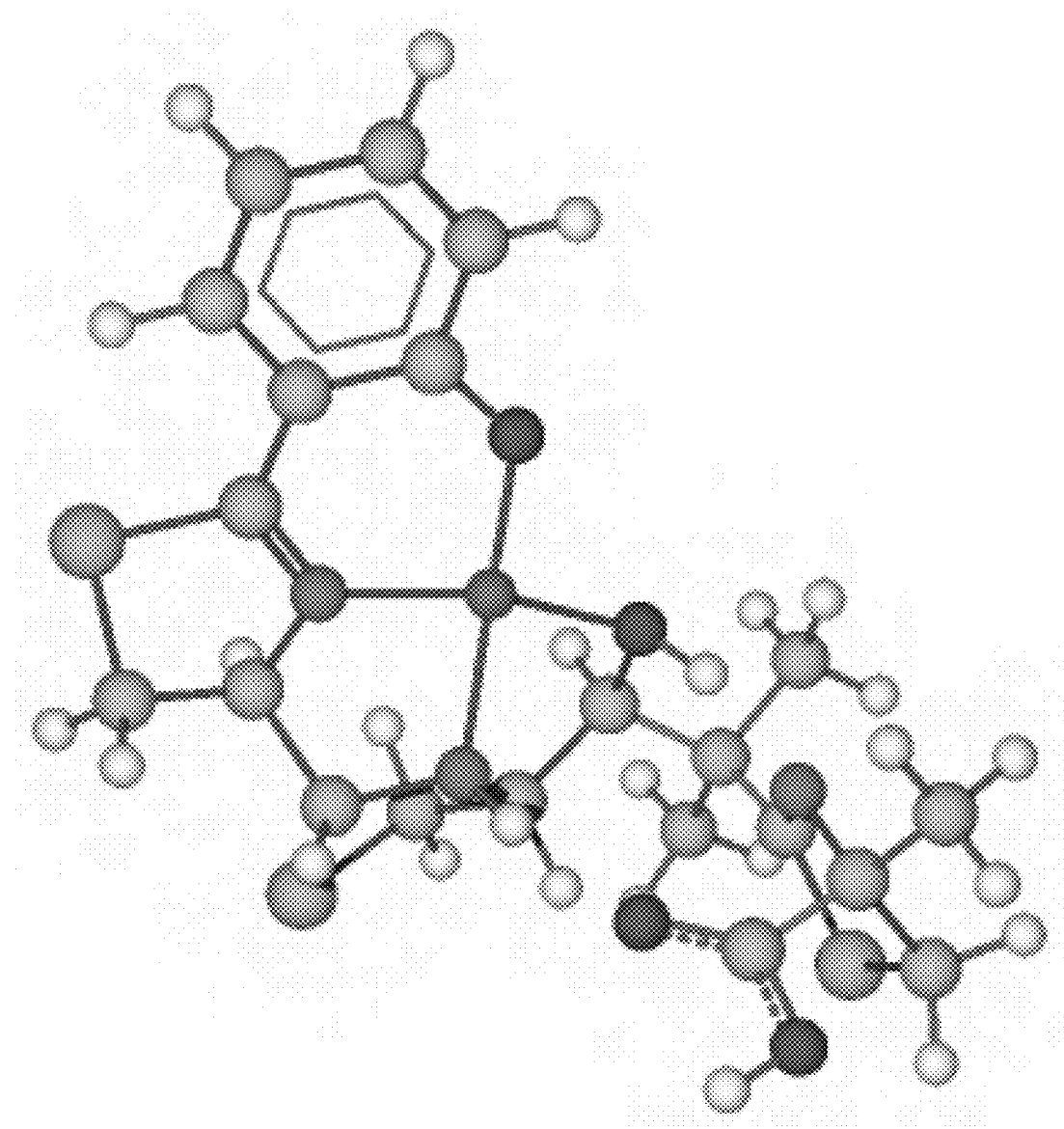
FIG. 18A-B depicts chemical structures showing the salicylate moiety of yersiniabactin interacts with superoxide species.

The Salicylate Moiety of Yersiniabactin Directly Contacts Copper (II) within Complex To determine which structural moieties of yersiniabactin contact copper (II) within the small molecule complex, density functional theory-based (DFT) simulations was employed, validated by CID fragmentation analysis of the ESI-generated positive ion. Previous crystallographic work indicates that yersiniabactin coordinates iron in an octahedral coordination by donation of six electron pairs: three from negatively charged oxygens of the phenolate, the ionized secondary alcohol, and the carboxylate and three from the neutral nitrogen atoms of the rings. As a control, our DFT approach yielded connectivity and structure of a neutral high-spin ferric complex essentially identical to the crystallographic structure. Similar structures were maintained for both the anionic and cationic form of the ferric complex achieved by subtraction or addition of a proton, respectively. In contrast, the DFT simulation of the copper (II)-yersiniabactin complex in both neutral and cationic form supports square-planar coordination of the cupric atom by the phenolate and secondary alcohol oxygens and two sets of electron pairs from the neutral nitrogen atoms, as the most stable cupric yersiniabactin structure (FIG. 18A).

Unlike the compact ferric complex, the cupric complex has a free arm consisting of the terminal ring and carboxylate, in effect, loss of 187 amu is already pre-loaded.

Figure 18B:
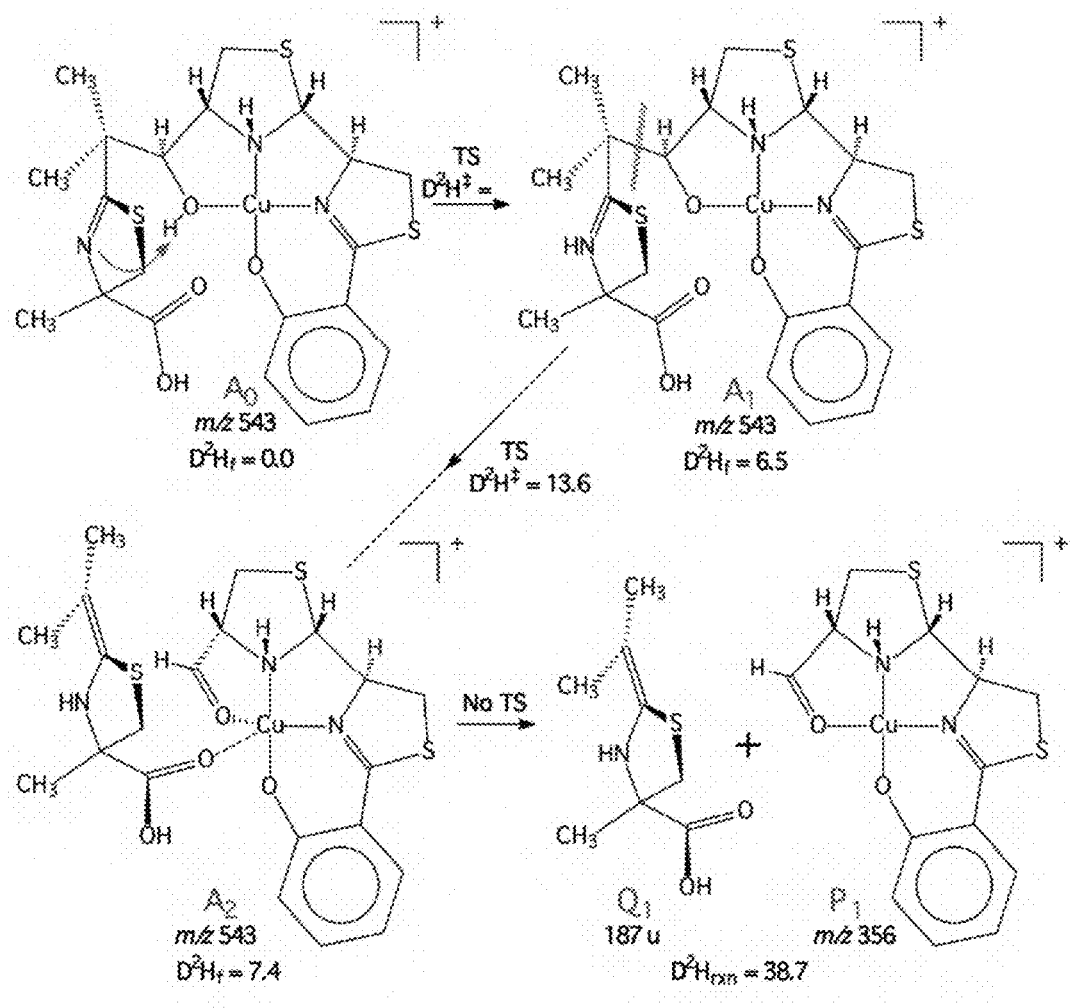

Experimental validation of this model was provided by CID fragmentation analysis of ESI-generated cations. The MS/MS ion spectra of m/z 543 from peak 1 is dominated by the predicted neutral loss of 187 amu (FIG. 18B). An additional fragment at m/z 328 is also observed. MS/MS of the $^{65}$Cu isotopomer revealed a similar fragmentation pattern shifted upward by 2, consistent with the copper-containing CID fragments. The favorable loss of 187 mass units was consistent with DFT calculations of this complex, which predict carbon-carbon bond cleavage through a modest barrier of 13.7 kcal/mol relative to most stable form $A_0$ followed by separation of the copper-bonded fragment and the 187 amu moiety which requires 38.7 kcal/mol relative to $A_0$. The resultant aldehydic moeity in the intermediate product ion is consistent with the observed CO (28 amu) loss. Together these data provide a structural rationale supporting yersiniabactin as a facile copper ligand in which the cupric ion is coordinated directly to the phenolate oxygen.

Discussion for Examples 11 to 16

The results presented above demonstrate that yersiniabactin expression protects uropathogenic E. coli from macrophage respiratory burst. A new function for the virulence-associated siderophore yersiniabactin as a copper (II)-dependent superoxide dismutase mimic was determined. Additionally the structure-activity relationship between yersiniabactin and copper (II) was analyzed to establish a chemical rationale for the biosynthetic expense associated with the expression of multiple siderophore types by Enterobacteriaceae. By conducting density functional theory-based (DFT) simulations, the structural moieties of yersiniabactin that contact copper (II) within the small molecule complex were determined.

Secreted copper chelators have been previously described among multiple environmental bacterial isolates. In this context, yersiniabactin is a virulence-associated functional homologue of methanobactin, a chromopeptide whose complexes with copper demonstrate superoxide dismutase, oxidase and hydrogen peroxide reductase properties. The SOD activity associated with copper (II)-yersiniabactin complexes is of particular importance given that the uptake of copper (II) is recognized to be of critical importance in the interaction between macrophages and intracellular pathogens. The ability of yersiniabactin to neutralize host defenses by binding copper (II) and the additional property of this complex to dismutate superoxide radicals, therefore, has physiological relevance as both activities may contribute to the relative success of E. coli to colonize a particular host niche persistently.

Reaction mechanisms of copper-complexed aromatic compounds exhibiting SOD activity suggest that superoxide anions react primarily with the copper (II) held within the copper (II)-yersiniabactin complex, rather than the yersiniabactin backbone (1, 2).

$$Cu(II)+O_2.^- \rightarrow Cu(I)+O_2 \quad (1)$$

$$O_2.^- + Cu(I) + 2H^+ \rightarrow Cu(II) + H_2O_2 \quad (2)$$

Figure 19:
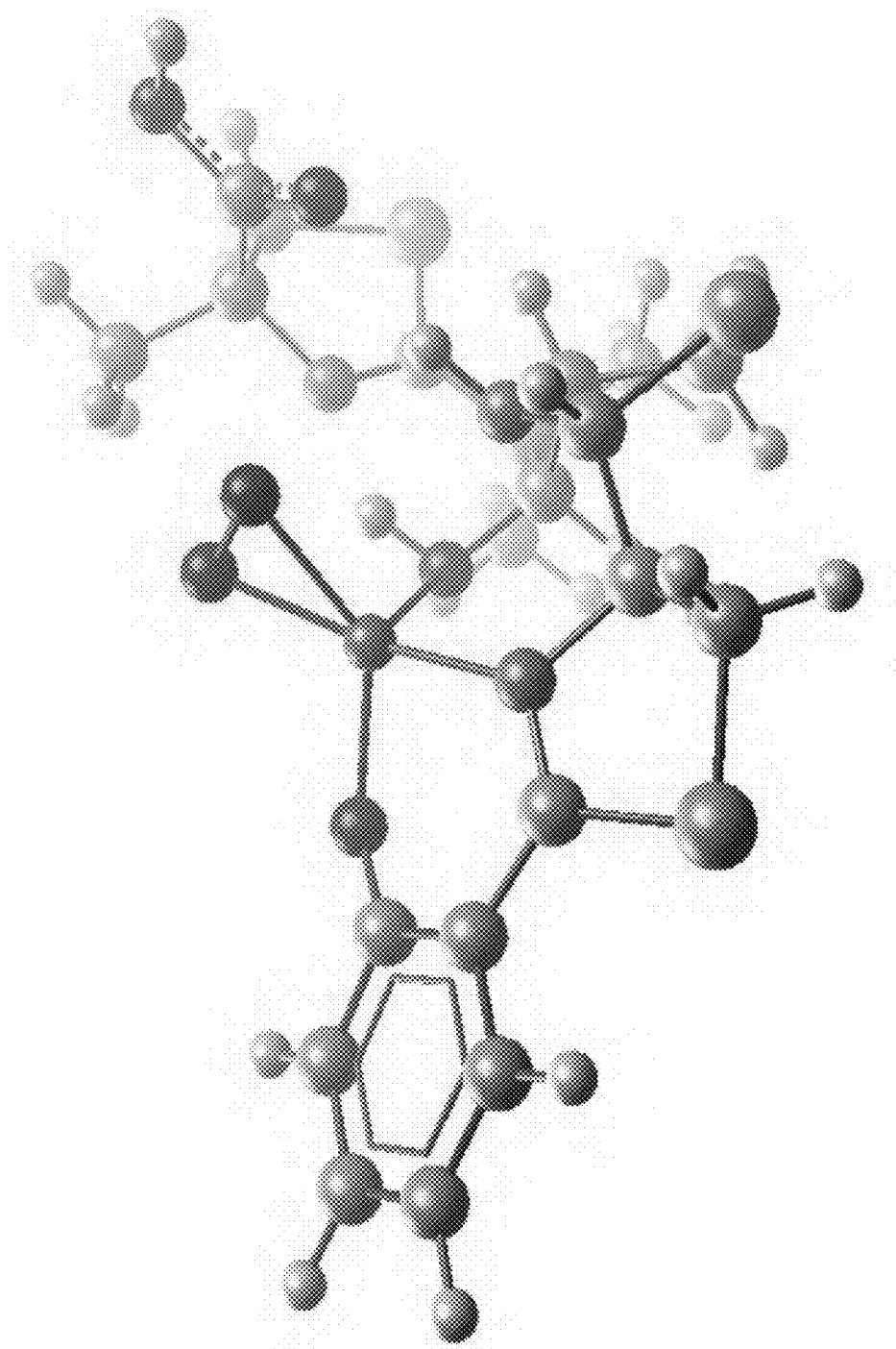
FIG. 19 depicts a structure showing that redox cycling of cupric yersiniabactin as a basis for SOD activity. DFT prediction of the superoxide adduct to the most stable form of the cupric complex, $A_0$. The cupric ion has released an OH and a NH electron pair donor in favor of maintaining a distorted square-planar geometry in which those two ligands have been replaced by the oxygens from the $O_2$ moiety. The resultant product may revert to a stable state with accompanying release of molecular oxygen.

The reaction with superoxide anion reduces copper (II) to copper (I), which in turn gets oxidized by interaction with another superoxide anion, releasing molecular oxygen and thereby regenerating the parent copper (II)-complex. Initial DFT simulations suggest that direct interaction of superoxide anion with copper (II) in complex with yersiniabactin is energetically favorable (FIG. 19). Therefore, the catalytic activity is mainly a result of the reversible redox reactions within the Cu(II)/Cu(I) couple in the complex. Alternatively, excess superoxide anions may oxidize the phenolic moiety of yersiniabactin, resulting in the transient formation of phenoxyl radicals. These phenoxyl radicals may react with reduced copper ions of the complex and also result in regeneration of the complex.

Nonribosomal polyketide synthase assembly lines yield remarkably complex chemical scaffolds fashioned from simple building blocks such as acyl-CoAs and amino acids, achieving high functional group density and molecular diversity. The synthesis of multiple complex natural products such as siderophores with redundant function is intriguing from an evolutionary perspective. It has been argued that unlike primary metabolic pathways, secondary metabolic products are promiscuous and favor molecular diversity. The tendency of microbial secondary pathways to produce a suite of natural products with molecular diversity may additionally result from selective pressure within host niches. Yersiniabactin's ability to bind copper and the structure-activity relationship that informs this activity may thus reflect an example of microbial convergent chemical evolution in response to selective host pressures. Similarly, other microbial siderophores and natural microbial products may facilitate additional enzymatic or catalytic functions that have been previously unappreciated. With greater understanding of the microbial secondary product structures and their biosynthetic pathways, we may be able to integrate their biochemical and physiological roles in a broader evolutionary perspective.

Materials and Methods for Examples 11-16

Bacterial Strains and Cultivation

UT189, a well characterized and fully sequenced uropathogenic *E. coli* strain, was used as the prototypic pathogen in these examples. UT189 mutant strains are listed in Table 2. Bacterial cultures were grown from a single colony in Difco™ Luria-Bertani broth, Miller (LB) (BD, Franklin Lakes, N.J.) for three hours, and subsequently diluted 1:100 into M63 medium supplemented with 0.2% glycerol and 10 mg/mL niacin (Sigma). Bacterial cultures were incubated for 18 hours at 37° C. in a rotary shaker.

TABLE 2

UTI89 mutant strains used in this study.

| Strain | Gene function | Reference |
|---|---|---|
| UTI89ΔybtS | salicylate synthase, yersiniabactin biosynthesis | Snyder et al. 2004. Infect Immun 72: 6373-6381 |
| UTI89ΔentB | isochorismate lyase, catecholate siderophore (enterobactin/salmochelin) biosynthesis | Snyder et al. 2004. Infect Immun 72: 6373-6381 |

Deletion-Strain Construction:

In-frame deletions in UT189 were made using the red recombinase method, as previously described, using pKD4 or pKD13 as a template. To confirm the appropriate deletions, PCR with flanking primers was performed. Antibiotic resistance insertions were removed by transforming the mutant strains with pCP20 expressing the FLP recombinase.

Chemicals and Reagents:

Methanol (HPLC grade) and water (HPLC grade) were purchased from Fisher Scientific (Fisher Scientific, Pittsburgh, Pa., USA). Salicylic acid, cupric sulfate, ferric chloride, gallium nitrate, and bovine serum albumin were purchased from Sigma (Sigma-Aldrich Corporation, Saint Louis, Mo., USA).

Tissue Culture:

RAW264.7 cells were obtained from the American Type Culture Collection (Manassas, Va.) and maintained in Gibco's RPMI 1640 medium (Invitrogen) containing 10% fetal bovine serum in 5% CO2 at 37° C.

Bacterial Survival within RAW 264.7 Macrophages:

RAW264.7 macrophages were detached from TPP cell culture flasks by scraping into ice-cold medium containing 10% FBS, washed twice, and resuspended in triplicate in 24-well plates at $10^5$ cells/well. The seeded wells were treated in the following order: 24 hours in i) ice cold media containing 10% FBS, followed by a 24 hour incubation in ii) serum-free media, followed by a 24 hour incubation iii) in serum-free media either with or without 20 μM $CuSO_4$. Wild type *E. coli* (strain UT189), ΔybtS, or MG1655 were grown for 18 hours to stationary phase in M63 minimal media and added to the RAW264.7 macrophages at a macrophage/bacteria ratio of 1:10 or 1:1. Bacterial phagocytosis was allowed to proceed for 30 min at 37° C. At 30 minutes, one set of samples (total inoculum) was lysed in 0.1% Triton X-100 solution and plated onto LB-agar plates for CFU enumeration to provide total bacterial inoculum. A second set (adherent group) was washed 4 times with 1× ice-cold PBS to wash extracellular bacteria, lysed with serum-free media containing 0.1% Triton X-100 and plated as described above. A third set of samples (kill group) was treated with serum-free media containing 100 g/ml gentamicin (Invitrogen), and incubated for one hour to allow bacterial killing to occur in the RAW264.7 cells. Following this incubation period, the samples were washed 4 times with 1×PBS to remove extracellular gentamycin, and then lysed with 0.1% Triton, and plated onto LB-agar. Bacterial survival was determined as the ratio of CFU in the killing group over CFU of the uptake group.

Inhibition of Oxygen Dependent Innate Activity of RAW264.7 Cells:

Diphenyleneiodonium (DPI) produces a non-competitive inhibition of NADPH oxidase by its covalent binding to FAD. RAW264.7 macrophages were infected with bacteria as described above, and samples were treated with 20 μM DPI (Sigma) inhibitor. Samples containing media alone, media with 20 μM copper, or media with both 20 μM and 10 DPI were used as additional controls.

Superoxide Dismutase Activity:

Superoxide dismutase (SOD) activity was measured indirectly in multiwell plates, using xanthine/xanthine oxidase as the superoxide-generating system and the reduction of Dojindo's highly water-soluble tetrazolium salt, WST-1 (2-(4-Iodophenyl)-3-(4-nitrophenyl)-5-(2,4-disulfophenyl)-2H-tetrazolium, monosodium salt) to produce a water-soluble formazan dye as the detector (Sigma-19160). Reduction of WST-1 was monitored at 440 nm in a final volume of 100 μL. One unit of activity was defined as the amount of compound which blocked 50% WST-1 reduction under these conditions. Bovine Cu/Zn SOD was used as a standard (Sigma S-7571). Controls for the SOD assay included ensuring that the compound did not affect the superoxide-generating reaction, testing solvent alone, and ensuring that the compound does not react independently with WST-1. To determine whether SOD activity is retained in the presence of protein, these experiments were repeated in the presence of 1.0 mg/mL bovine serum albumin (Sigma).

Yersiniabactin Isolation and Characterization:

1.0 M ferric chloride or copper sulfate was added to UTI89ΔentB cell culture supernatants to a final concentration of 50 mM and purified as described previously. The supernatant from this precipitation reaction was harvested by centrifugation and subsequently subjected to preparative chromatrography, and eluted with 100% methanol. The presence of cupric and ferric yersiniabactin was confirmed by LC-MS detection of these complexes at m/z 543 and 535, respectively.

High Resolution Liquid Chromatography-Mass Spectrometry:

High resolution mass spectrometry analyses of cupric- and ferric-yersiniabactin complexes were conducted using a Bruker Maxis Q-Tof operated in positive ion mode as previously described. The samples were directly infused at a flow rate of 0.3 µL/min. The ion spray voltage was set to 4500 V for positive ion and −500 V for negative ion mode, respectively. The nebulizer gas (air) and turbo gas (air) were set to 0.4 bar and 4.0 L/min, respectively. The heater temperature was 180° C.

Theoretical Calculations:

Theoretical calculations were performed to characterize the potential-energy surface (PES) associated with fragmentation. Conformer spaces for precursors (cupric and ferric complexes with yersiniabactin) and intermediates were explored by Monte-Carlo/MMFF molecular mechanisms/dynamics methods. From these results, structures of precursors, intermediates, and scans for associated transition states were explored by using the PM3 semi-empirical algorithm, both in Spartan for Linux v. 2 (Wavefunction, Inc.). Minima and transition states were optimized by DFT (Density Function Theory, part of Gaussian 03 suite, Gaussian Inc.) with functional PBE0 (PBE1 PBE in Gaussian parlance) with basis set Def2-SVP confirmed by vibrational frequency analysis. In addition, connections of transition states to minima were examined by inspection, projections along normal reaction coordinates, and path calculations as necessary. Single-point energies were calculated at level PBE1PBE/Def2-SVP and scaled thermal-energy corrections were applied using scaling factors for B3LYP/6-31 G(d,p). The hybrid functional and basis sets were chosen on basis performance with transition metal complexes. DFT was selected for high-level calculations because it requires less computational overhead than ab initio methods and performs adequately. All results are reported in kJ/mol as enthalpies of formation relative to a selected, suitable precursor.

The complexes are all radicals because of the transition-metal cation involved. The cupric complexes are spin 1/2 with the $Cu^{2+}$ in low-spin state whereas the ferric complexes have spin 5/2 with the $Fe^{3+}$ in high-spin state.

Statistical Analyses:

Statistics and graphs were generated using Graph Pad Prism 4. The t test was used to compare growth differences between paired strains. Analyses of paired strain differences in siderophore production were performed using the Wilcoxon signed rank test for significance.

Example 17

Small Molecule Inhibitor of Yersiniabactin Biosynthesis

Para-aminosalicylic acid (PAS, 4-aminosalicylate) is an early antituberculosis drug identified and used in the 1940's. It is currently used rarely for highly drug resistant tuberculosis infections. While PAS's primary mechanism of action has been historically considered to be inhibition of para-aminobenzoic acid (PABA) biosynthesis, comparable to sulfa drugs, recent work (FEMS Microbial Lett. 2010 October; 311(2):193-9.) suggests that it is capable of inhibiting mycobactin biosynthesis in mycobacteria. Mycobactin is a siderophore believed to be important for *Mycobacterium tuberculosis* infections.

The Examples above suggest that the siderophore yersiniabactin is an important virulence factor in urinary pathogenic *E. coli*. The ability of PAS to inhibit yersiniabactin biosynthesis in a urinary pathogenic *E. coli* strain was examined. PAS was observed to selectively inhibit yersiniabactin biosynthesis at levels where it did not inhibit in vitro growth.

The relatively low toxicity of PAS makes possible a quick translation to evaluation in animal models and humans. In UTI, *E. coli* cystitis strains that progress to bacteremia and sepsis carry a genetic marker of yersiniabactin production at high frequency.

Example 18

Detection of HPTT, a Product of the Ybt Biosynthetic Machinery

Figure 20B:
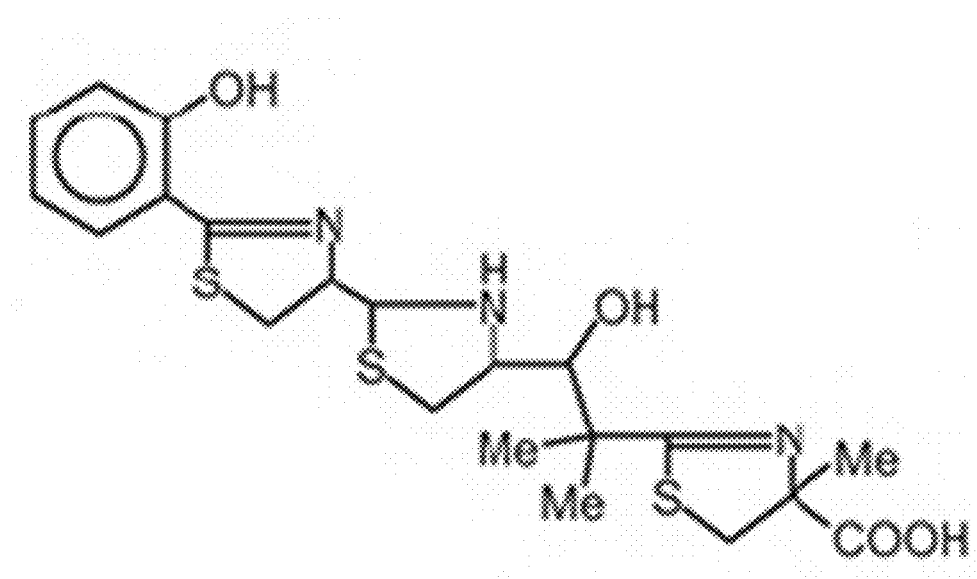
Figure 21A:
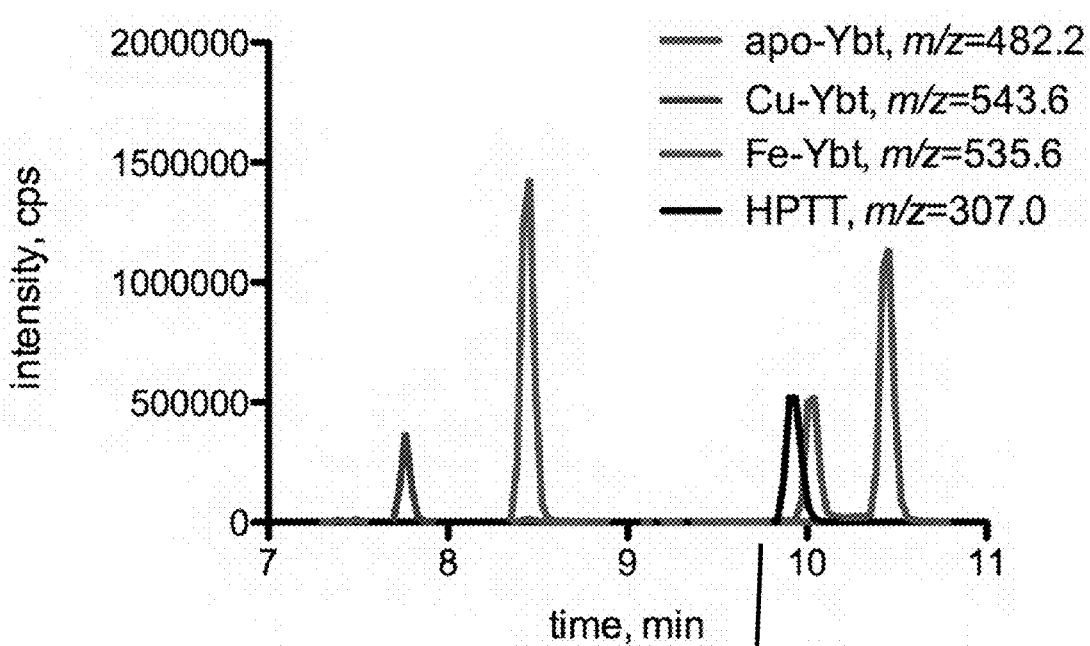
FIG. 21A depicts a chromatograph showing the retention time of various products identified in the supernatant of UT189 cultures grown in minimal media and subjected to LC-MS with electrospray ionization. Blue, red, and green traces of this chromatogram represent Cu-, apo-, and Fe-Ybt, respectively.
Figure 21B:
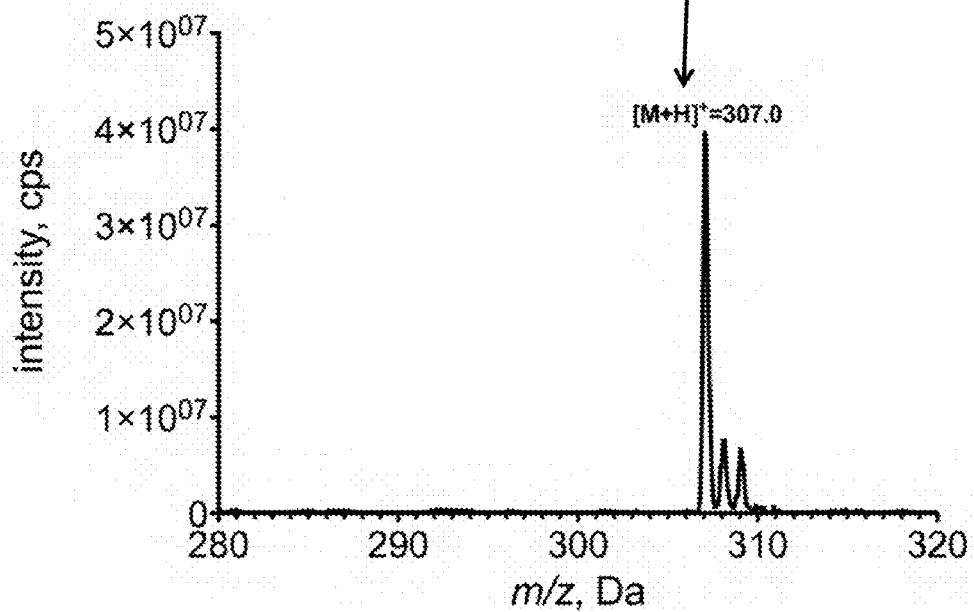
(FIG. 21B) The black trace at a m/z ratio of 307 was predicted to be HPTT.

The genes for yersiniabactin production are clustered in a high pathogenicity island (HPI) and DNA sequence and mutational analysis have revealed several required genes, including those for conversion of the central biosynthetic metabolite chorismate into salicylate. During synthesis of yersiniabactin, a three-ring HPTT (hydroxyphenyl-thiazolinyl-thaizolinyl) is formed (FIG. 20) and docked to the most downstream of the carrier protein domains of high molecular weight protein 2 (HMWP2). To see if UTI89, a model uropathogenic *E. coli* strain that contains the Ybt HPI, produces HPTT under Fe-restricted conditions, supernatants from cultures grown in minimal media were collected and liquid chromatography-mass spectrometry with electrospray ionization was performed. FIG. 21 shows blue, red, and green traces of a chromatogram detecting Fe-, Cu-, and apo-Ybt under these conditions. Additionally, a peak was observed where the predominant ion had a m/z ratio of 307, which is predicted for the soluble HPTT structure. We were unable to detect a m/z ratio corresponding to a HPTT-metal complex, only apo-HPTT was detected. Qualitatively, it looked like the levels of this potential HPTT, 307 ion were roughly equal to the levels of Ybt being released into the supernatant, which is surprising if HPTT is only produced as a transient intermediate in the pathway, and according to theory should be covalently attached to HMWP2.

Figure 22A:
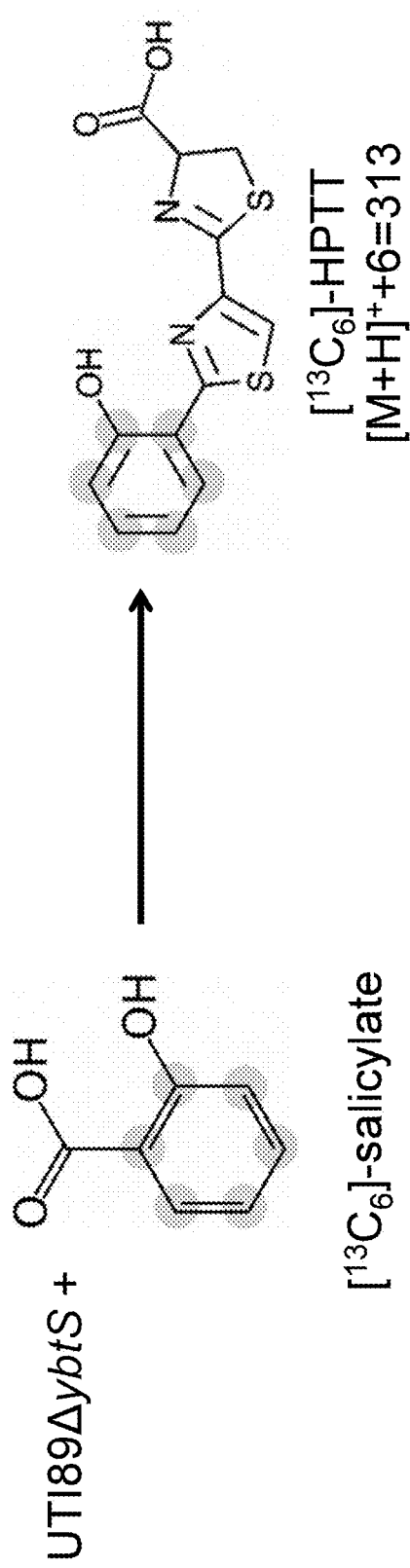
FIG. 22A-B depicts a chromatograph confirming that the 307 ion has 6 carbons derived from the benzene ring of salicylate.
Figure 22B:
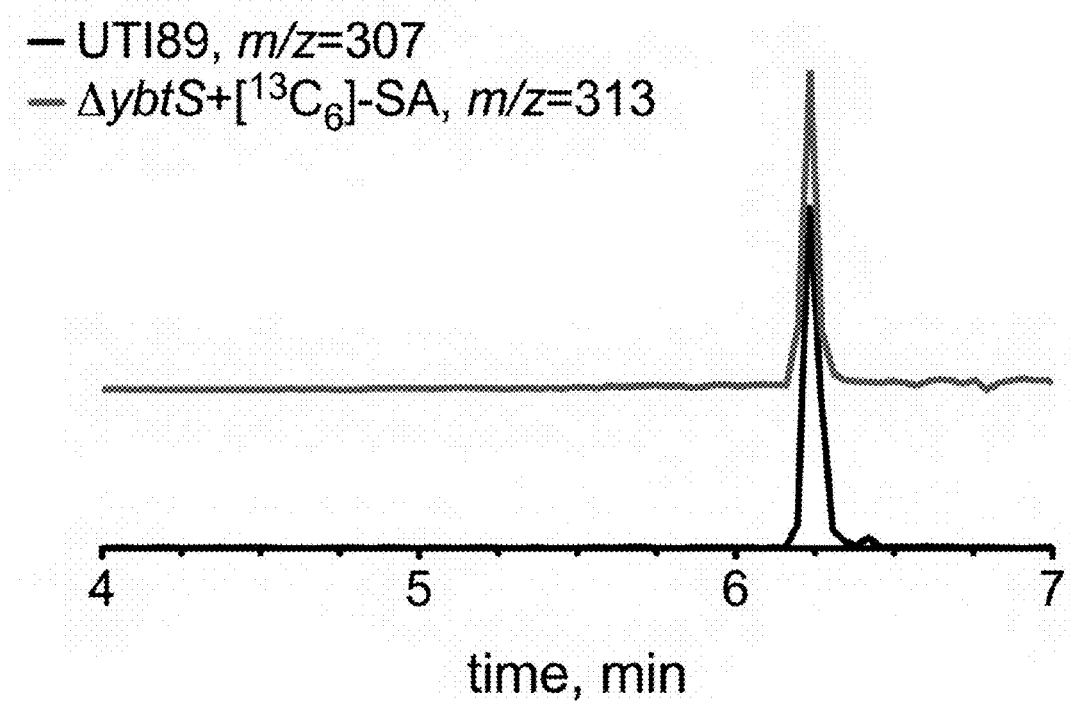

The detection in UT189 supernatant of an ion with a m/z ratio of 307, does not confirm that the detected ion is HPTT. To validate the structure and confirm detection of HPTT, isotope labeling experiments were performed. An isogenic mutant in UT189 that has the salicylate synthase gene, ybtS, deleted was grown in exogenous carbon-13 labelled salicylate. The sample was evaluated for the production of a molecule that elutes at the same time as the 307 peak, but this time with a m/z ratio 6 units higher. After analyzing the supernatants again, that is exactly what was observed (FIG. 22). In the ybtS knockout culture supplemented with $^{13}C$-salicylate, an ion with a mass charge ratio of 313 eluted at the same time as the 307 ion in a wildtype UT189 culture. This confirmed that the 307 ion has 6 carbons derived from the benzene ring of salicylate.

Figure 23A:
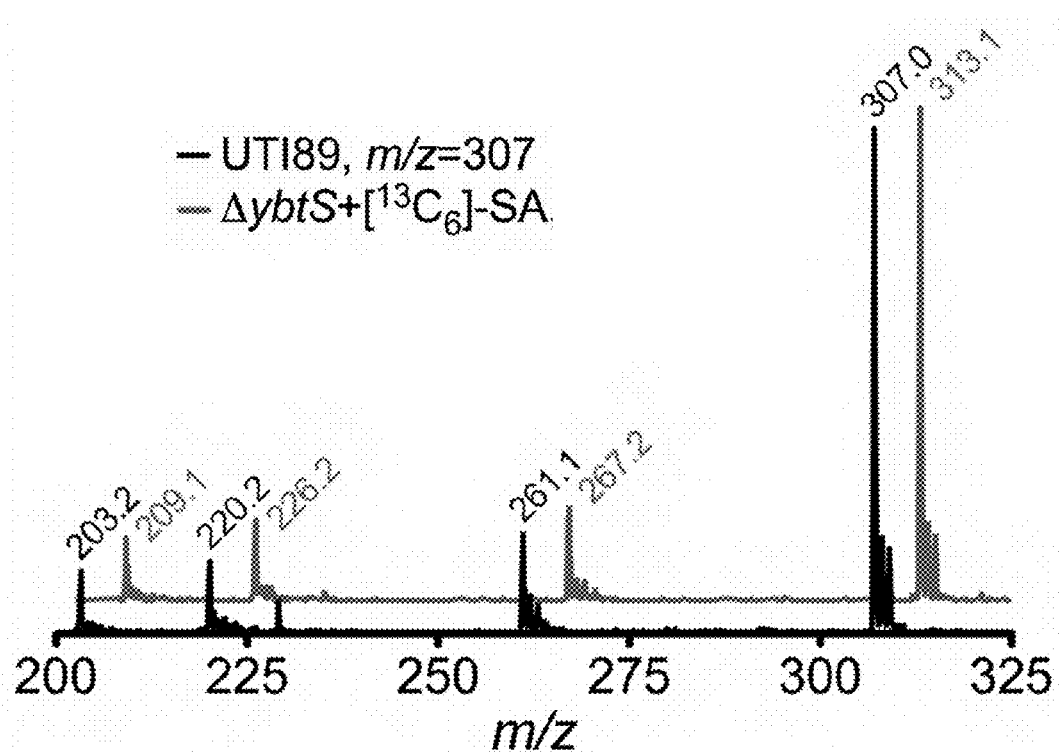
FIG. 23A depicts a chromatograph after tandem MS (MS/MS). The 307 and 313 peaks lose the same characteristics fragments at 46, 87, and 104. A loss of 46 is common and corresponds to a carboxylic acid, which is part of the HPTT structure. The 87 and 104 losses are unique, but we could map them to parts of the second heterocylic ring. The 87 fragment includes the nitrogen, while the 104 fragment contains the sulfur.
Figure 23B:
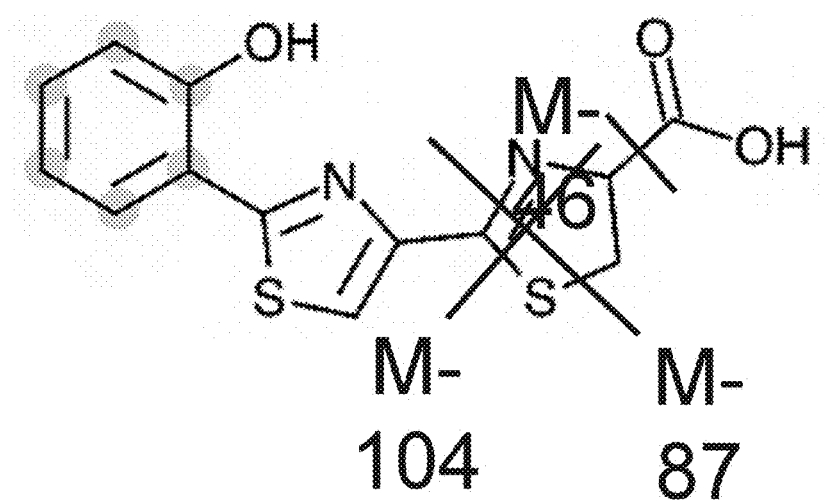
FIG. 23B diagrams how HPTT is broken down after tandem MS.

The next step in structure validation was to perform tandem MS to see how the 307 ion falls apart. In MS/MS, the molecules are ionized once to put a charge on them, and then ionized again to fragment them into pieces. The 307 and 313 peaks lose the same characteristics fragments at 46, 87, and 104 (FIG. 23). A loss of 46 is common and corresponds to a carboxylic acid, which is part of the HPTT structure. The 87 and 104 losses are unique, but were mapped to parts of the second heterocylic ring. The 87 fragment includes the nitrogen, while the 104 fragment contains the sulfur. To finalize the structure characterization, we looked at sulfur isotope abundance and confirmed that HPTT was detected.

Figure 25:
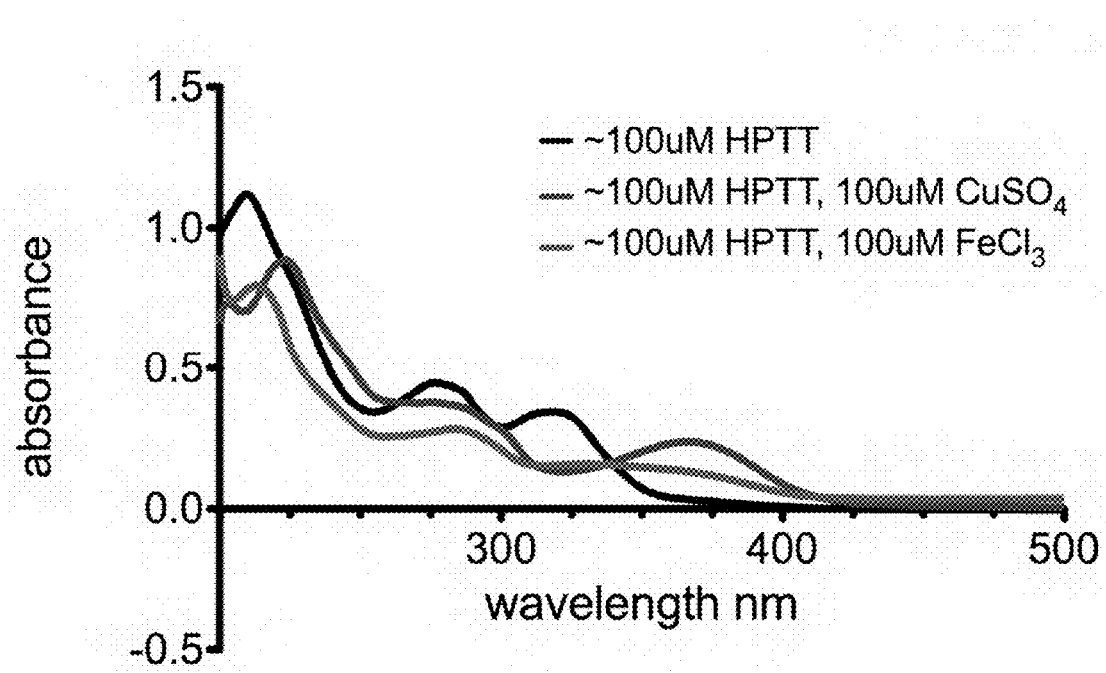
FIG. 25 depicts a graph showing the UV-Vis spectra of HPTT is red-shifted in the presence of Fe (III) and Cu (II).

At this point, it had been confirmed that HPTT is detectable in vivo in a model UPEC strain that makes yersiniabactin. FIG. 24 confirms that HPTT is detected in wildtype UT189 but not UT189 strains comprising deletions in the yersiniabactin synthesis pathway (ybtS and ybtE). Given that HPTT is being secreted outside the cell and that it is made in relatively high abundance, we wanted to see if HPTT could be performing a specific function for the bacteria, and not simply a transient intermediate along the way to Ybt (FIG. 24). Given that its structure is similar to yersiniabactin, a siderophore, we hypothesized that it could interact with metals. Using solid phase extraction and HPLC, HPTT was purified to homogeneity with no contaminants, as detectable by HPLC. The purified compound was used to look for interactions with iron and copper by UV-Vis spectroscopy. We found that UV-Vis spectra of HPTT is red-shifted in the presence of Fe (III) and Cu (II) (FIG. 25).

To test the hypothesis that HPTT production is common to all Ybt+ bacteria a number of model UPEC strains were grown in Fe-restricted media. Mass spectrometry methods developed by us were then used to look for HPTT. We were able to detect HPTT in all of the strains that make yersiniabactin, but not in CFT073 which does not (Table 3). Then, a number of non-E. coli clinical isolates from patients with bladder infections were evaluated and it was discovered that they too produced HPTT, if they make Ybt.

Figure 26:
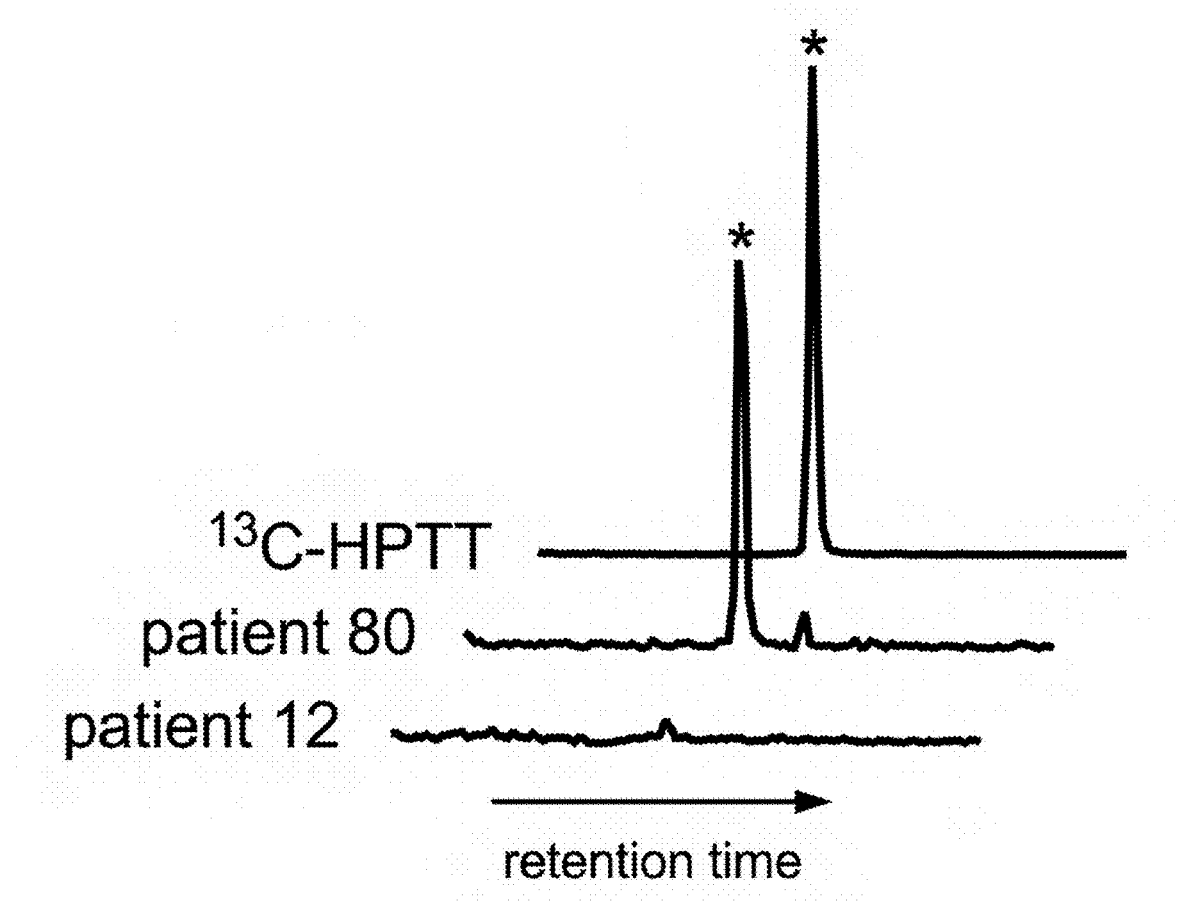
FIG. 26 depicts a chromatograph showing that HPTT can be detected in the urine of patients with a UTI caused by a Ybt-positive strain.

At this point, we knew that HPTT it is made when Ybt biosynthesis is reconstituted in vitro and when Ybt-positive strains are grown in culture, but this does not prove that it is actually made and secreted at the site of an infection. To test the hypothesis that HPTT is made during an infection, we analyzed urine samples from patients with bladder infections caused by Ybt positive and negative E. coli strains and looked for HPTT by LC-MS in the urine. Of 17 patients whose UTI was caused by a Ybt-positive strain, HPTT could be identified in 4 of the urines (FIG. 26). This was unconcentrated urine, and we suspect that if the assay was repeated with concentrated urine or a larger LC-MS injection volume, the number of positive urines would be even higher.

TABLE 3

HPTT is produced by Ybt+ strains across species

| Strain Name | Species information | Ybt | HPTT |
|---|---|---|---|
| UTI89 | model uropathogenic E. coli | yes | yes |
| CFT073 | model uropathogenic E. coli | no | no |
| NU14 | model uropathogenic E. coli | yes | yes |
| HOST 080 | E. coli urinary isolate | yes | yes |
| TOP 52 | K. pneumonia urinary isolate | no | no |
| TOP 1856-1 | K. pneumonia urinary isolate | yes | yes |
| SJH-734 | C. koseri urinary isolate | yes | yes |

Introduction for Examples 19-28

Antibiotic resistance is widely recognized as one of the 21$^{st}$ century's pre-eminent public health challenges. These challenges are exemplified by urinary tract infections (UTIs), which are predominantly caused by uropathogenic Escherichia coli (UPEC). As clinicians struggle with the paucity of mechanistically new antibiotics targeting Gram-negative pathogens and dramatic increases in antibiotic resistance, UTIs are increasingly difficult to manage. As a result, UTIs present a high economic burden marked by increasing healthcare costs.[1] The potential for Gram-negative UTIs to progress to systemic infections motivates aggressive antibiotic use, which drives the selective evolution of antibiotic resistant strains among gut microbiota.[2] Along with concerns of treatment-resistant infections, there is a growing appreciation that current broad-spectrum antibiotic strategies cause detrimental changes to the human microbiome. Even in antibiotic-susceptible strains, post-therapy recurrence is common and may even paradoxically increase subsequent UTI risk.[3] The shortcomings of current broad-spectrum antibiotic approaches have motivated renewed interest in pathogen-specific antivirulence agents that selectively target pathogenic functions.[4]

Prior studies, aided by UPEC's genetic tractability, have identified numerous monogenic determinants of urovirulence in clinical E. coli isolates. Many of these genetic loci—termed virulence factors (VFs)—are non-conserved or on mobile genetic elements and connected to biochemical functions that correspond to the many divergent infectious components of uropathogenesis.[5] Recent UTI therapeutic development focuses on antivirulence drugs and vaccines that seek to disarm a pathogen by targeting VFs associated with UPEC adhesion, capsule antigens, surface polysaccharides, and iron acquisition.[6,7] If these approaches are successful, lower selective pressure for antibiotic resistance and minimal impact on commensal bacteria will be a major advance in infection pharmacotherapy.

Since uropathogenic adaptations are multifactorial, potent antivirulence therapies will require synergistic or additive combinations to be clinically efficacious.[7,8] By forcing pathogens to respond with multiple resistance adaptations to defeat these strategies, appropriate therapeutic combinations can also minimize emergence and proliferation of drug resistant pathogens. These principles underlie current combination anti-infective therapies against Helicobacter pylori, Mycobacterium tuberculosis, and HIV. Combination antivirulence therapeutic approaches for UTI are complicated by UPEC VF heterogeneity and the absence of defined core VFs that can be used to guide therapy. Such antivirulence agents will ideally be developed with a priori consideration of which targets co-exist within relevant pathogens.

To determine whether UPEC carry VFs in defined combinations we applied mathematical and statistical network analysis techniques to VFs in E. coli isolates recovered from hospitalized UTI patients with a high incidence of antibiotic resistance, pyelonephritis, and bacteremia. Mathematical network community detection is a powerful method for the analysis of complex data.[9,10] We observe that heterogeneous VFs across hundreds of clinical uropathogenic E. coli isolates group into four distinctive genetically defined urovirulence strategists. Among these exist low-risk antibiotic responsive strategists, as well as high-risk E. coli virulence strategists with links to antibiotic resistance and patient sex. The resulting virulence network of low- and high-risk E. coli strains supports antivirulence drug combinations as a plausible therapeutic approach and provides a preliminary strategic framework for their use.

Example 19

Clinical Isolate Characteristics

Three hundred and thirty seven bacteriuric inpatient clinical isolates (CIs) were derived from a recently described inpatient cohort collected over the course of one year (Table 4).[11] The CIs characterized in this study were predominantly female (n=263, 78%), with the median inpatient age range of 62 (range 19-101 years). One hundred and seven patients had pyelonephritis (32%); sixty had sepsis-induced hypotension (17%); and twenty-four had bacteremia (7%). The $E.$ $coli$ phylogenetic group distribution was typical of urinary isolates, where a majority of strains were contained in group B2 (68%).[12] One hundred and seventeen isolates were resistant to ciprofloxacin (CIP, 35%); ninety-six were resistant to trimethoprim/sulfamethoxazole (TMP/S, 29%).

TABLE 4

Clinical characteristics of clinical isolates tested in this study.

| metric | total (%) |
| --- | --- |
| female | 263 (78) |
| male | 74 (22) |
| pyelonephritis | 107 (32) |
| sepsis induced hypotension (SIH) | 60 (17) |
| blood stream infection (BSI) | 24 (7) |
| ciprofloxacin (CIP) resistant | 117 (35) |
| trimethoprim/sulfamethoxazole (TMP/S) resistant | 96 (29) |
| phylogenetic group B2 | 232 (68) |
| phylogenetic group D | 54 (16) |
| phylogenetic group B1 | 41 (12) |
| phylogenetic group A | 10 (3) |

Example 20

Virulence Factor Distribution

Figure 27A:
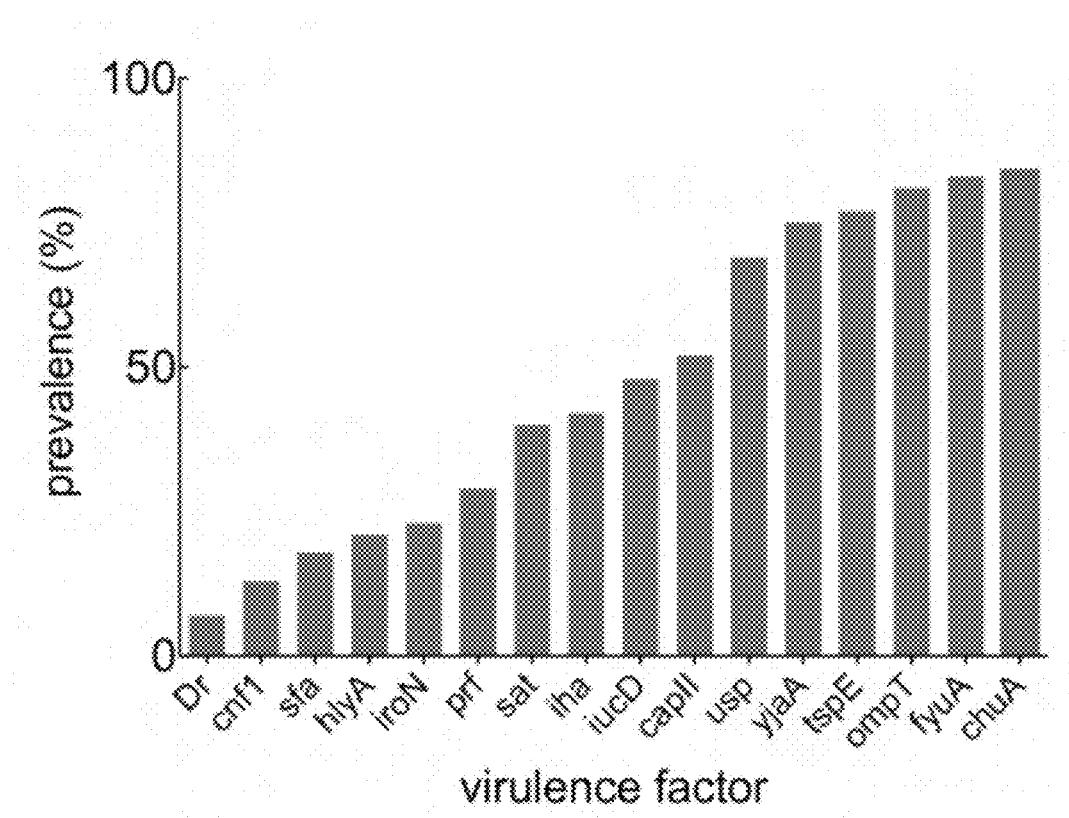
FIG. 27A-B depicts graphs showing that virulence score and antibiotic resistance are non-normally distributed.
Figure 27B:
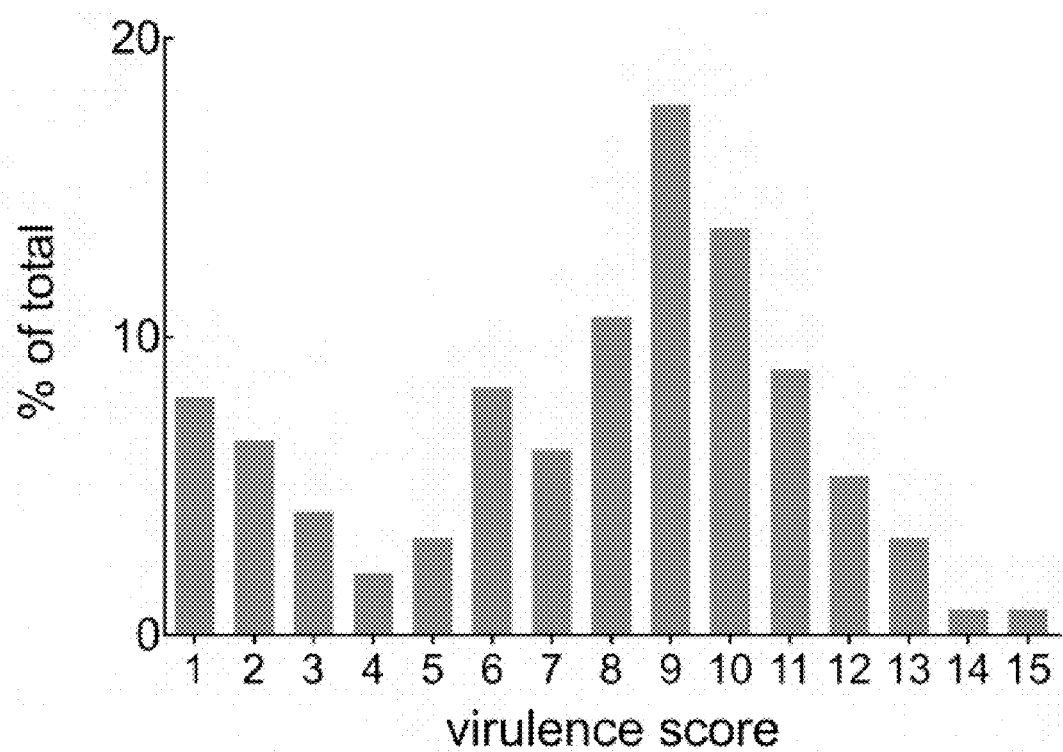
Figure 33:
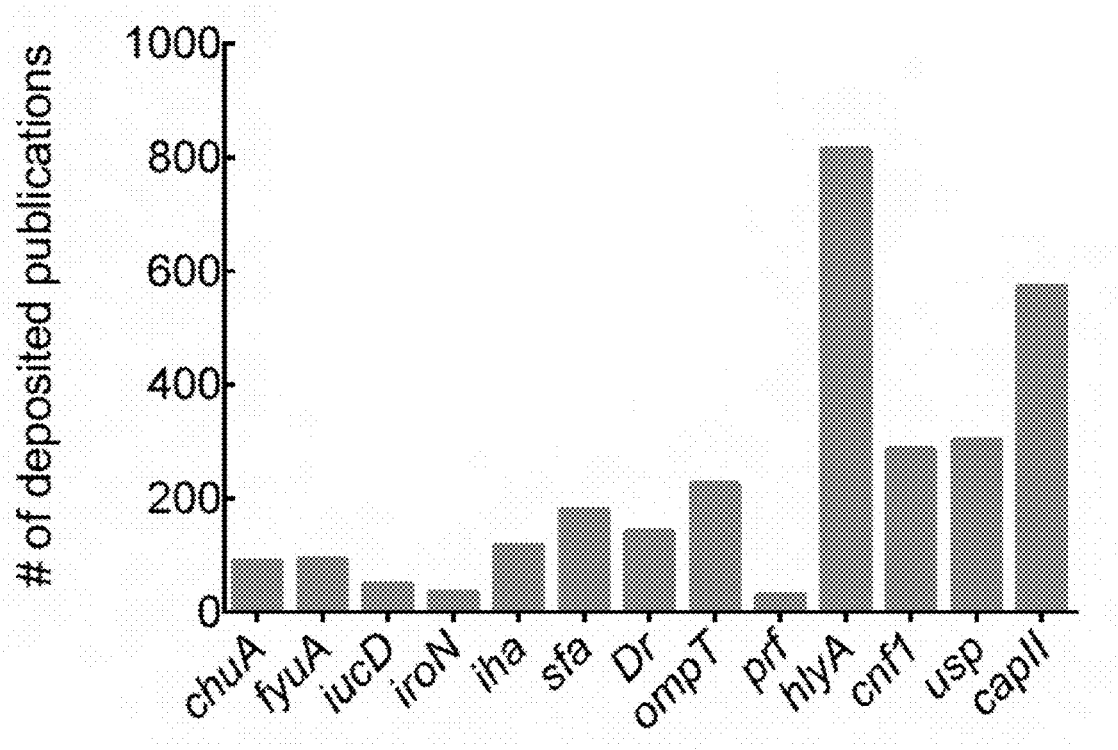
FIG. 33 depicts a graph showing total publications addressing virulence factors used in this study exceed 2,700. The figure shows the distribution of papers recorded in PubMed using each virulence factor as a query [(virulence factor*) AND (UPEC* OR E. coli*)]. The search was conducted on 3 Feb. 2014.

CIs were assessed for the presence or absence of sixteen VF genes (Table 5) that have been addressed in over 2,700 publications (FIG. 33). Virulence factor prevalence ranged from highly common (chuA; 84%) to infrequent (Dr; 7%, FIG. 27A). Using a z-test for normality, we found that the gene content is not normally distributed (p=0.031). Indeed, a histogram of the gene content frequency reveals a bimodal distribution with local maxima at one and nine virulence factors (FIG. 27B). This bimodal distribution is consistent with either two quantitative optima for VF content, or with the tendency of specific VFs to occur as modular groups.

TABLE 5

Virulence factors and their functions.

| Gene | Function |
| --- | --- |
| chuA | E. coli heme uptake |
| fyuA | Siderophore (yersiniabactin uptake) |
| ompT | Surface protease |
| tspE | Anonymous DNA fragment |
| yiaA | Hypothetical protein |
| usp | Bacteriocin |
| capII | Group II capsule antigen |
| iucD | Siderophore (aerobactin) |
| iha | irgA homologue adhesin |
| sat | Secreted autotransporter toxin |
| prf | Adhesin (P-related fimbriae) |
| iroN | Siderophore (salmochelin) |
| hlyA | Hemolysin |
| sfa | Adhesin (S-fimbriae) |
| cnf1 | Cytotoxic necrotizing factor |
| Dr | Adhesin (Dr-family) |

Example 21

Network Community Detection of Uropathogenic Strategies

Figure 28A:
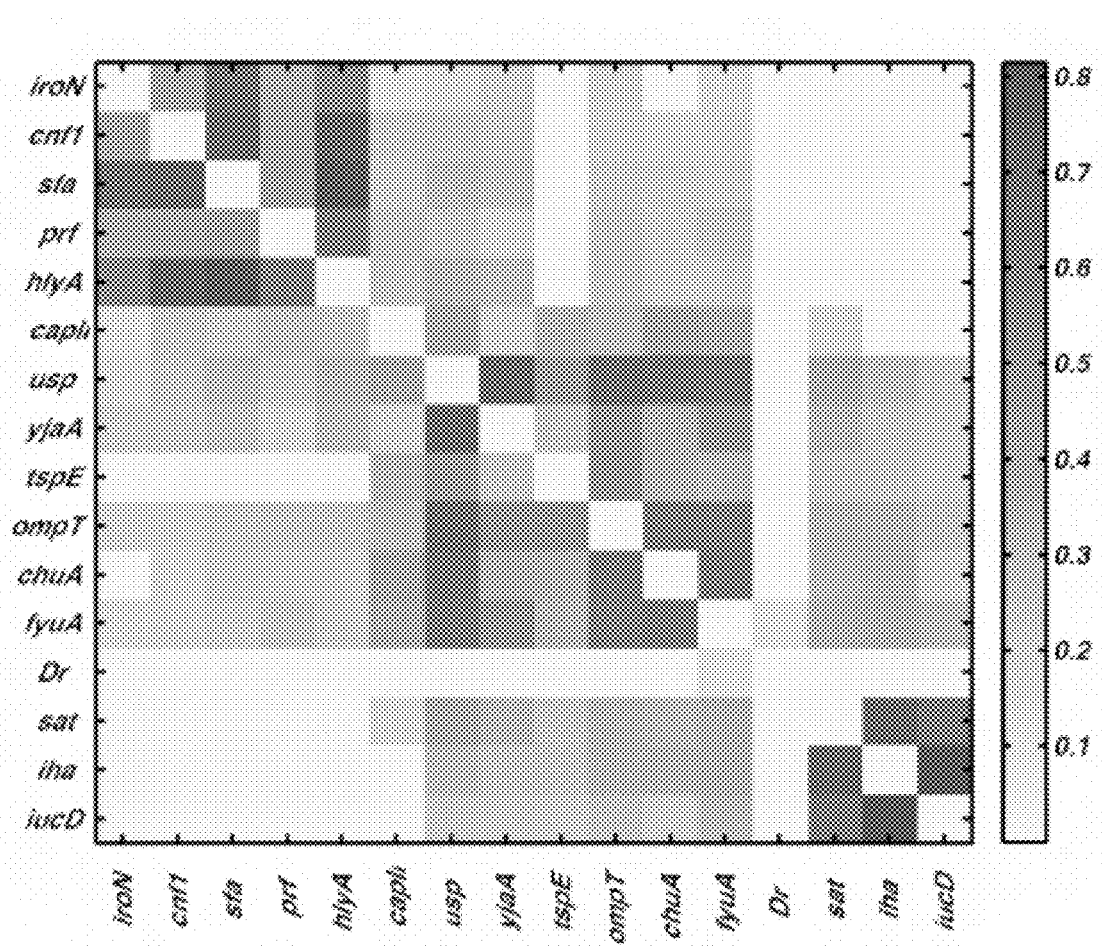
FIG. 28A-C depicts a heatmap and cluster diagrams showing network community detection clusters sixteen virulence factors into three discrete communities.
Figure 28B:
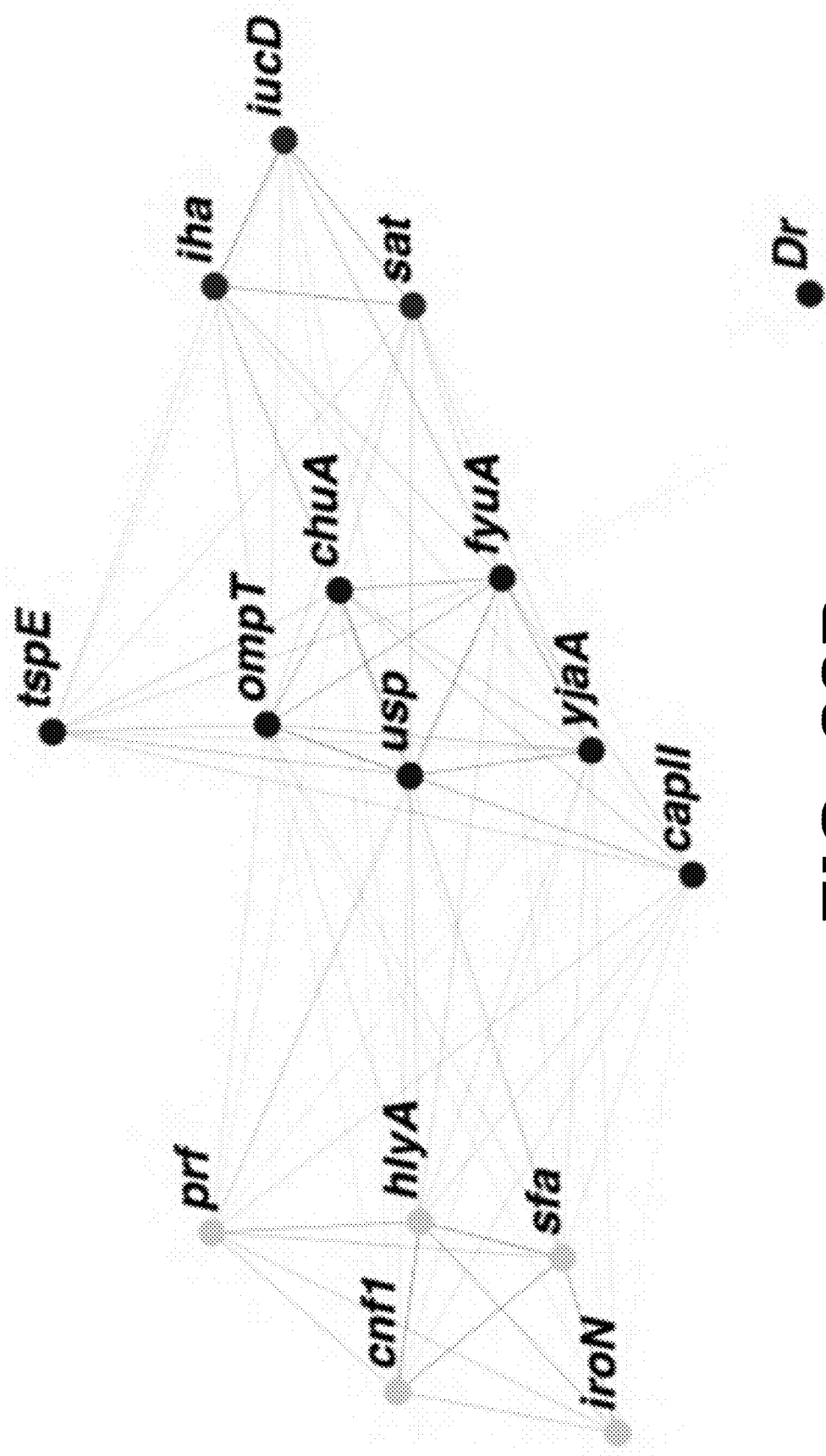
Figure 28C:
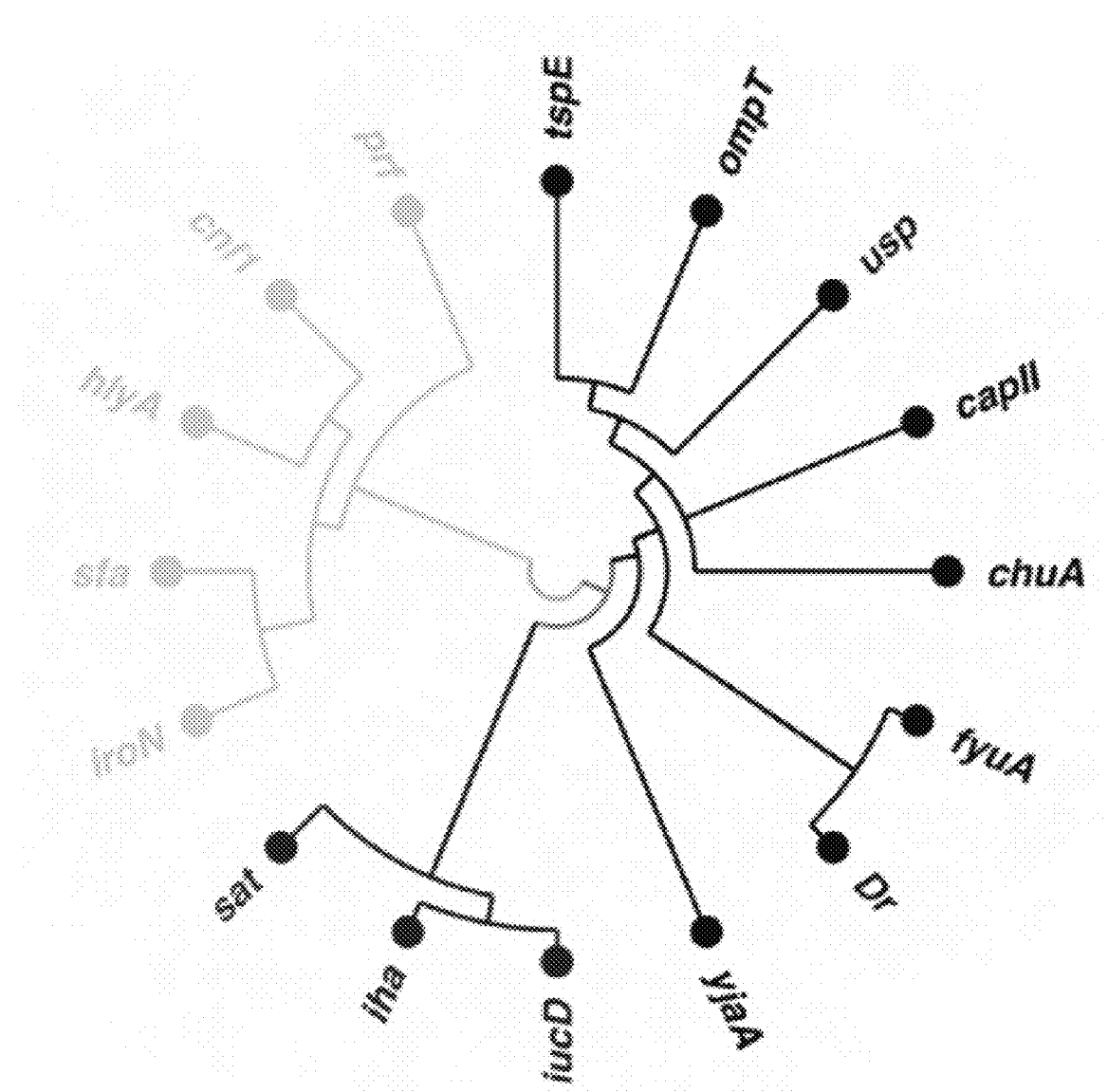

To determine whether UPEC carry definable VF combinations, we applied modularity-based community detection to a network of the 16 VFs alone. We set weighted edges between VFs by statistically significant positive correlations (by Fisher's exact test at the 1.5% one-sided level to ensure a single component connecting all 16 VFs). Three interrelated VF groups are discernible within the resulting heatmap (FIG. 28A), corresponding force-directed layout (FIG. 28B), and VF hierarchical clustering (FIG. 28C). Siderophore genes are uniquely represented in each VF cluster (VF cluster 1, fyuA; VF cluster 2, iroN; VF cluster 3, iucD). Weaker positive correlations between the fyuA-containing VF group and those containing iucD or iroN are evident in the VF adjacency matrix. Network community detection thus shows that the clinical isolates deploy VFs in stereotypical combinations, perhaps as adaptations to host ecology.

Example 22

Network Community Detection of Clinical Isolates

Figure 29A:
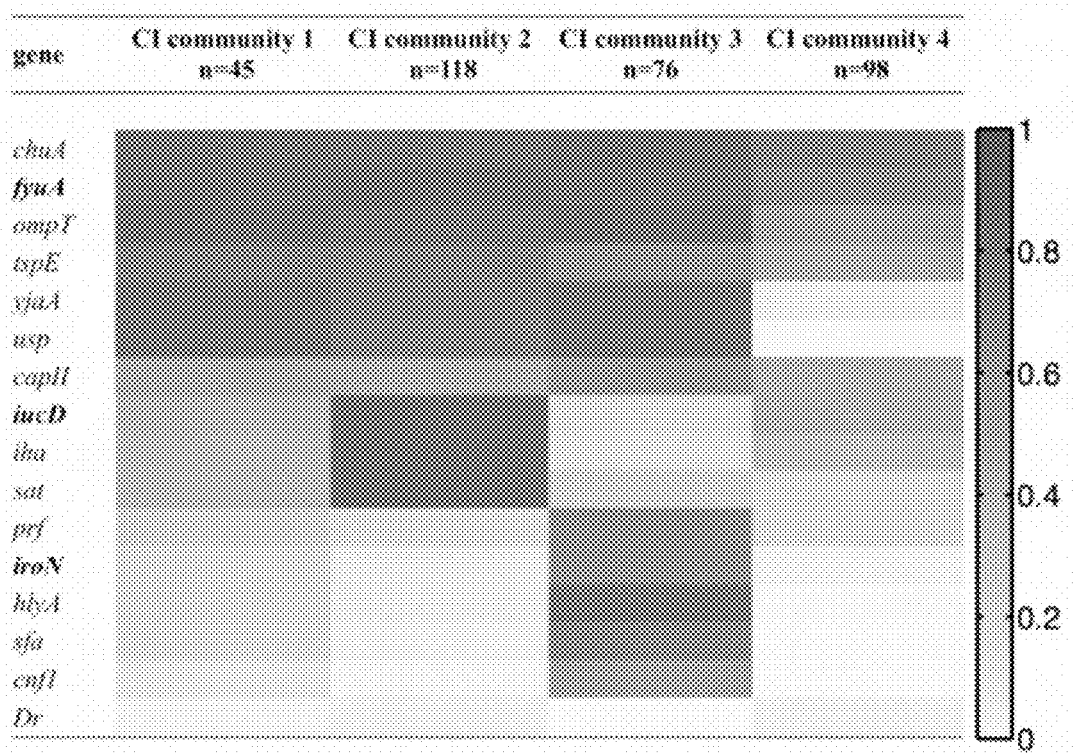
FIG. 29A-B depicts a heatmap and force-directed layout showing network community detection clusters three hundred and thirty seven (337) inpatient clinical isolates into four discrete communities.
Figure 29B:
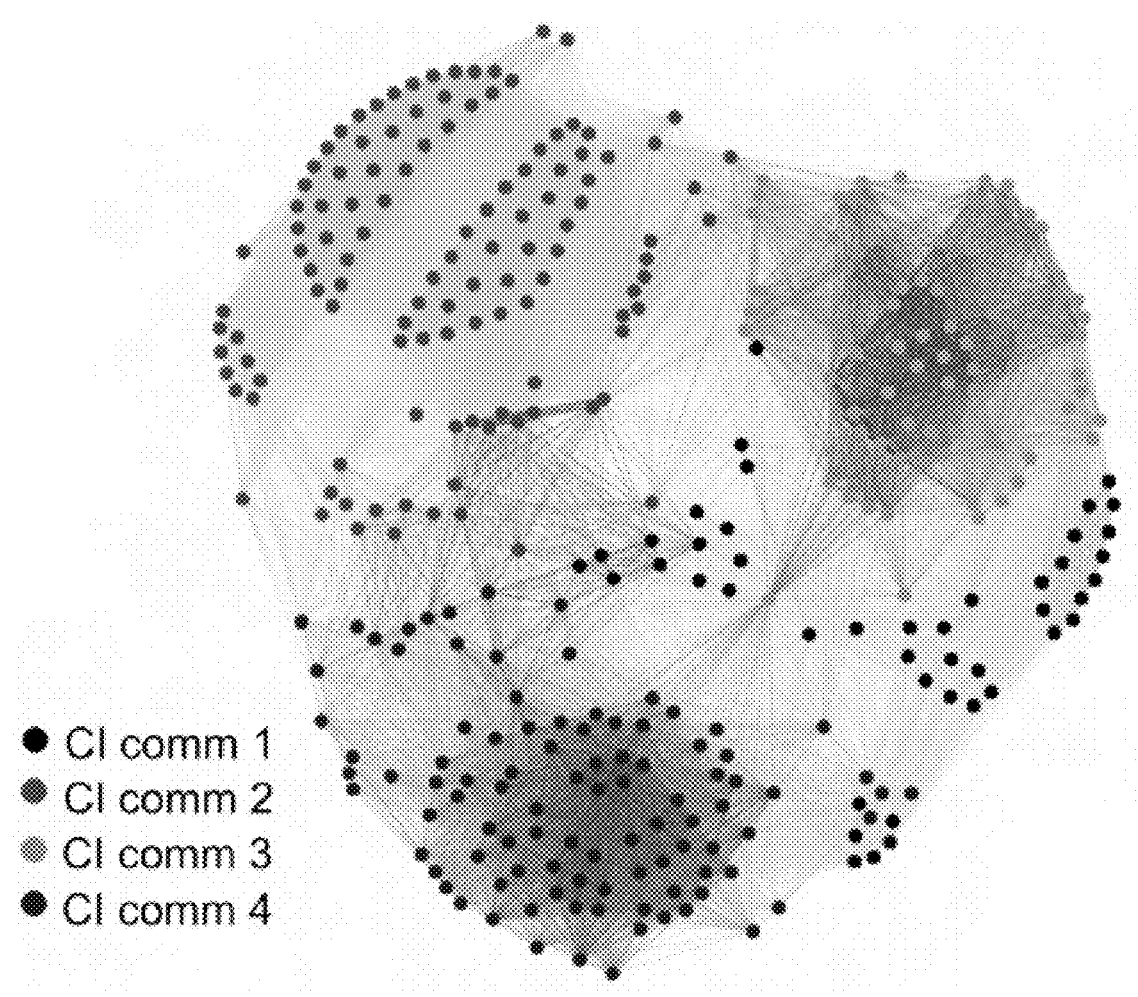

To determine whether UPEC carry characteristic VF combinations, we first applied modularity-based community detection to a network representation of the 337 clinical isolates. We defined a CI network of positively associated pairs after correcting for each VF's mean frequency and variance across the study population (see Methods for details). Modularity-based community detection resolves four clinical isolate communities (CI communities 1-4, n=45, 118, 76, and 98, respectively), representing four distinct virulence strategists (FIG. 29A). Each community contains distinctive VF patterns that together encompass multiple functional classes. A force-directed layout of this network indicates connectivity and strength of association between UPEC isolates (FIG. 29B). These qualitatively distinct distributions suggest that virulence genes are inherited as modular groups that define discrete uropathogenic strategies.

Example 23

Biclustering Analysis

Figure 30A:
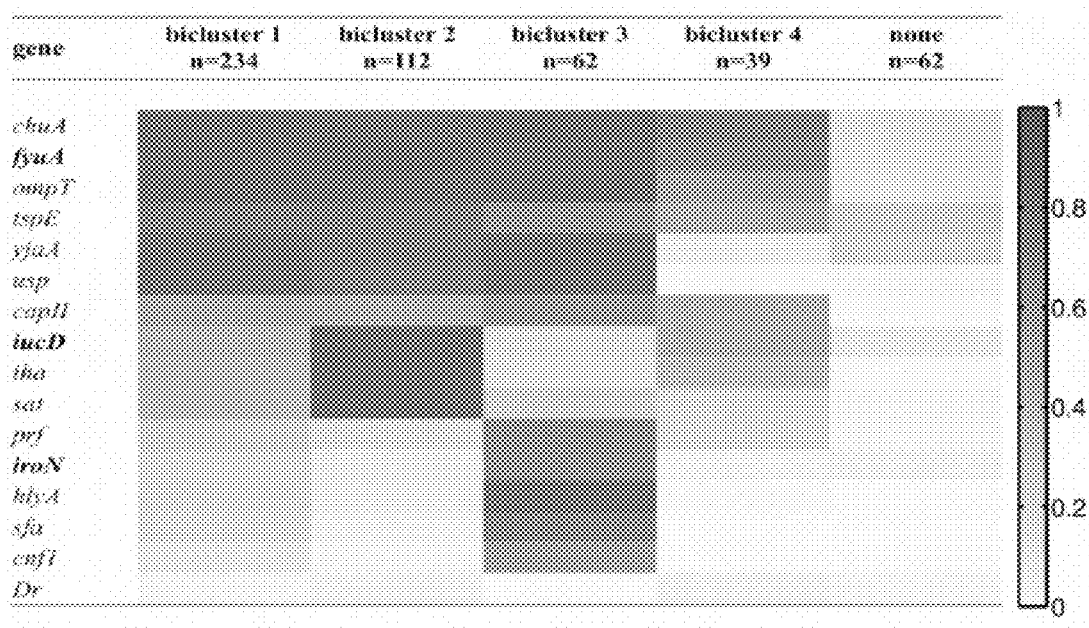
FIG. 30A-C depicts a heatmap and force-directed layouts showing bicluster and siderophore gene composition cluster clinical isolates similarly to network analysis.
Figure 30B:
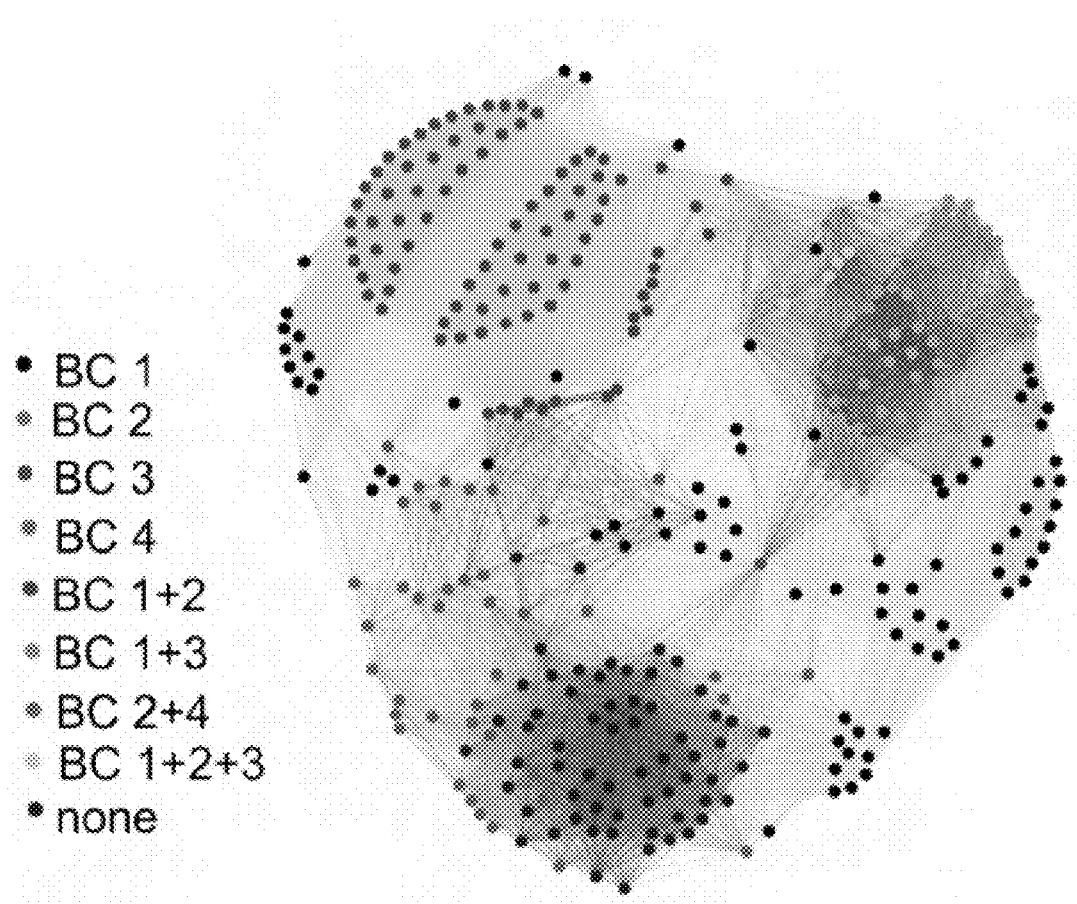

As a complementary alternative to network community detection, we employed an iterative binary biclustering method based on the Large Average Submatrix (LAS) procedure described by Shabalin et al.[13] Whereas the network community detection technique assigns each VF or clinical isolate to a single community, biclustering simultaneously identifies highly co-occurring VF and CI groups. A CI or VF may belong to multiple biclusters (BCs), or none at all. Four BCs emerge from our clinical population (BC 1-4, n=234, 112, 62, and 39, respectively, FIG. 30A), in a manner consistent with the four virulence strategists identified by network community detection. Overall, VFs associated with each bicluster are highly expressed across the constituent CIs (>72%). Biclustering did not classify 62 CIs with low VF gene content, the collection of which grossly resembles CI community 4. BC 4 is mostly redundant with BC 1 but is most distinguished by the absence of two genes (sfa and cnf1), and low prevalence of four genes (yjaA, usp, iroN, hlyA). The most abundant bicluster classifications resemble the CI communities, with BC1+2 (strains appearing in BC1 and BC2 but no other BCs) as the largest single group (n=89) closely resembling CI community 2. By annotating the force-directed layout of the CI strains with bicluster assignments, we reveal many similarities between the two clustering results (FIG. 29B and FIG. 30B). Both network community detection and clustering analyses independently identified four dominant virulence strategists composed of functionally diverse VFs.

Example 24

Virulence Strategists and Phylogeny

*E. coli* phylogenetic groups have been used extensively to classify clinical *E. coli* isolates and consistently associate group B2 with extraintestinal infections. We investigated whether CI phylogenetic groups are more informative than the specific virulence strategies by seeking associations with CI communities, biclusters, and siderophore genotypes (Table 4). Assignment to non-B2 phylotypes is associated with C4, BC4, or non-biclustered strains. Phylogenetic type otherwise exhibited no other clear associations with other VF-defined clusters. These results reveal that the best-resolved virulence strategies represent an organizational level that is distinct from phylogenetic grouping.

Example 25

Virulence Strategists and Siderophores

Figure 30C:
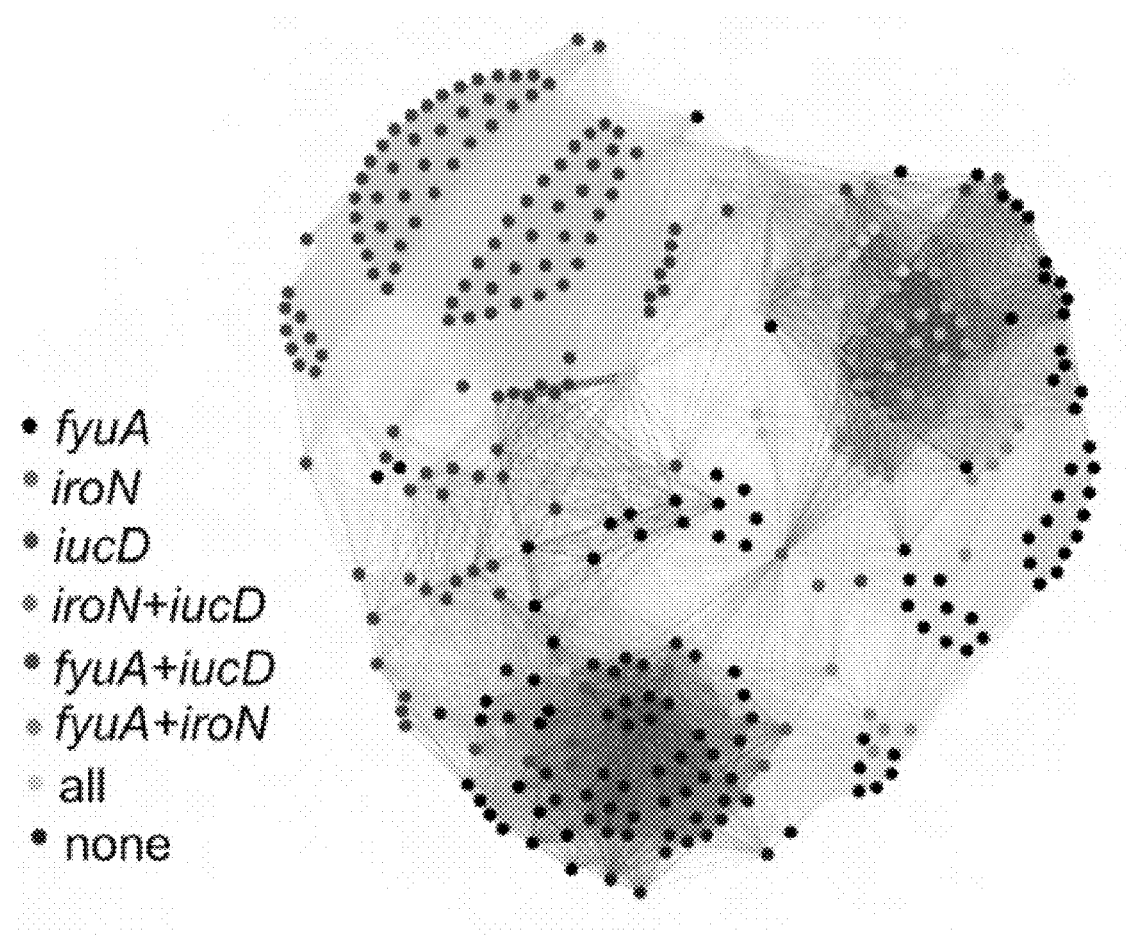
Figure 31A:
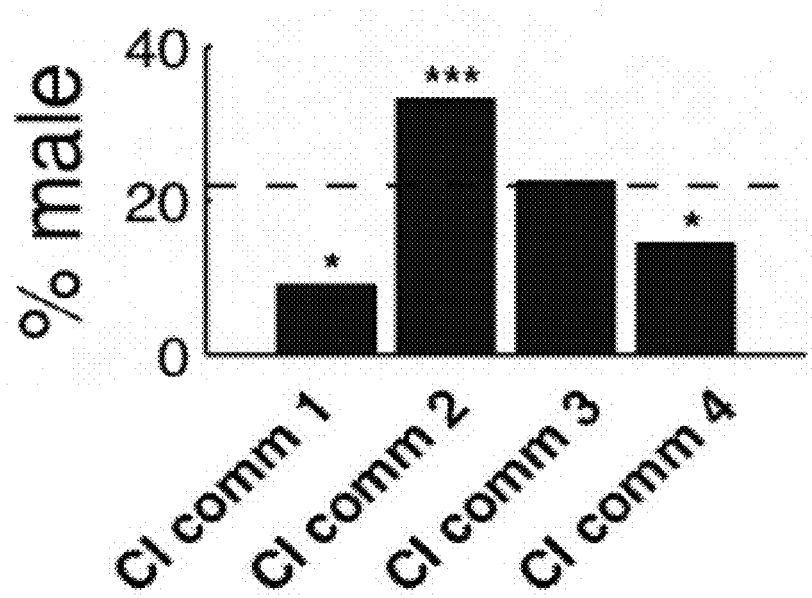
FIG. 31A-L depicts graphs showing CI classifications correspond to antibiotic resistance and patient sex.
Figure 31B:
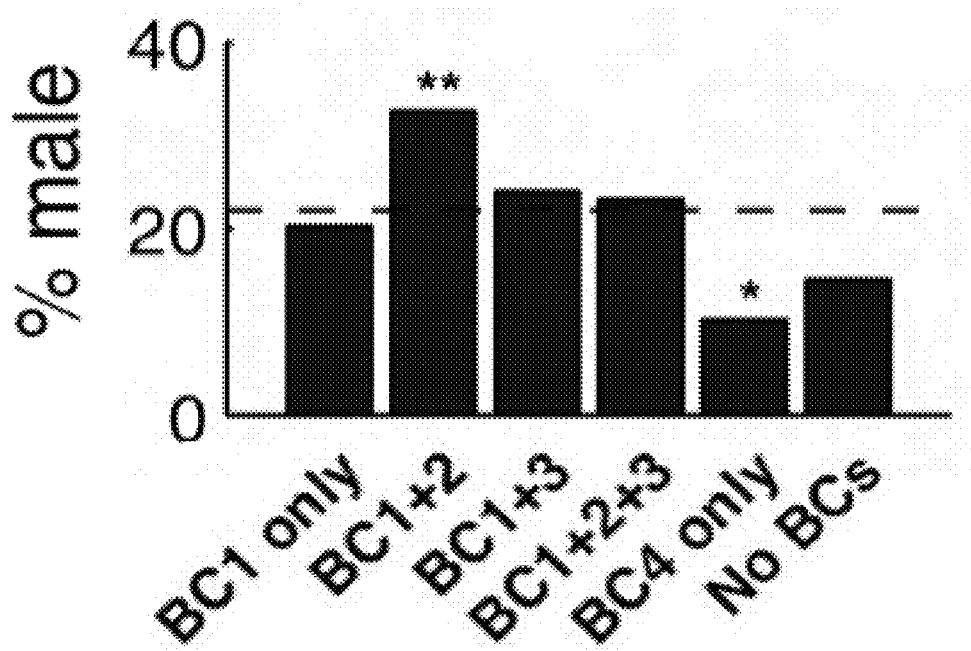
Figure 31C:
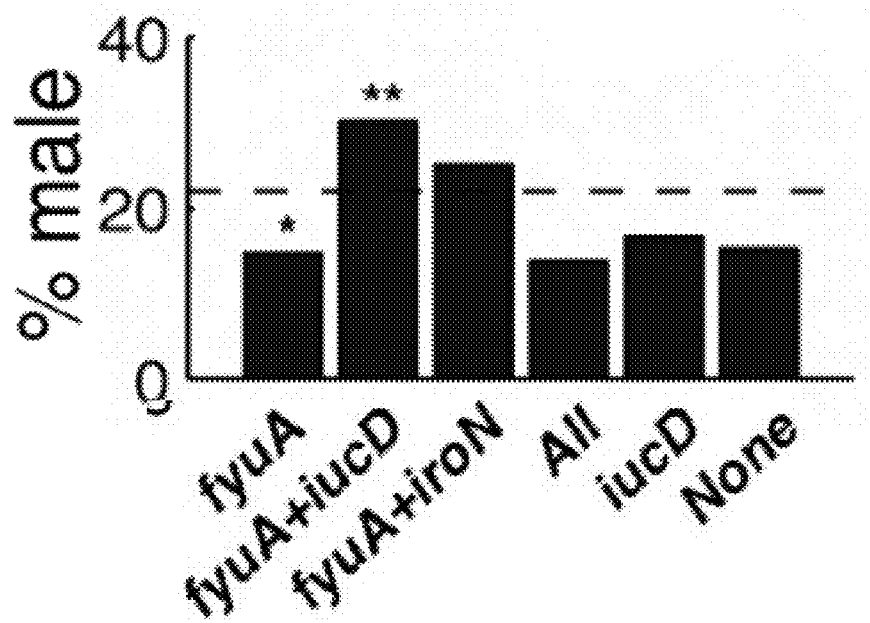
Figure 31D:
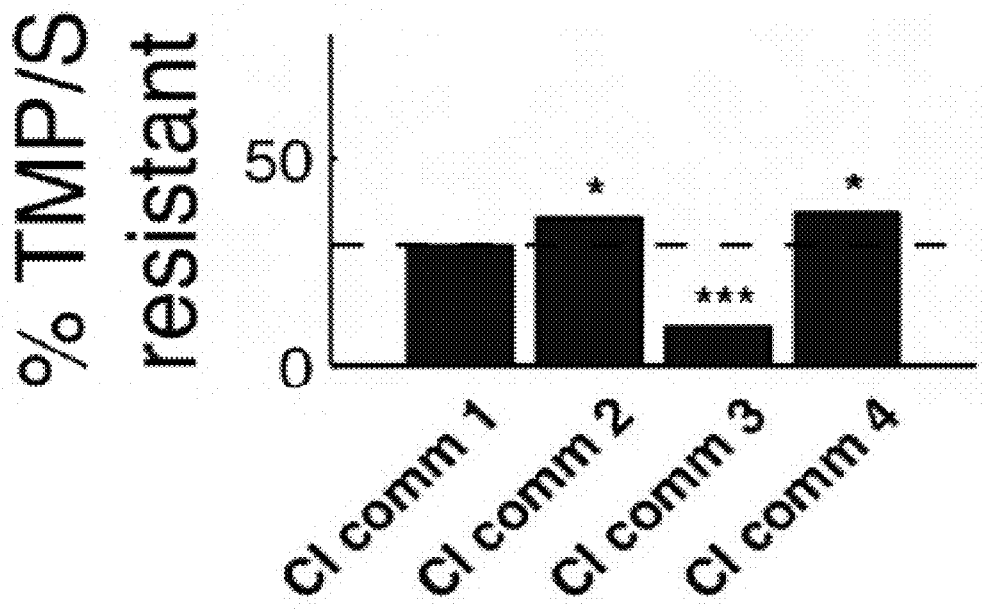
Figure 31E:
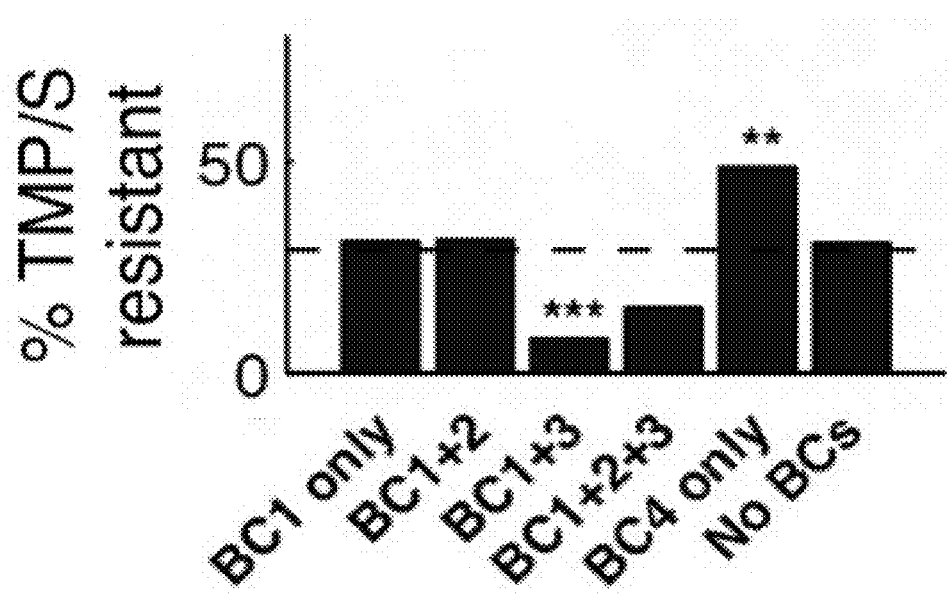
Figure 31F:
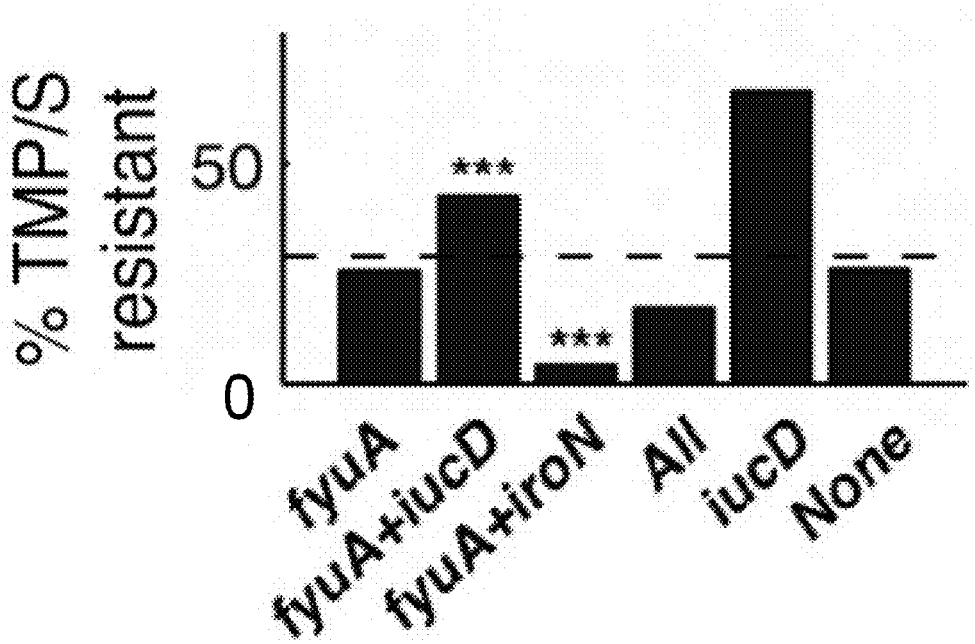
Figure 31G:
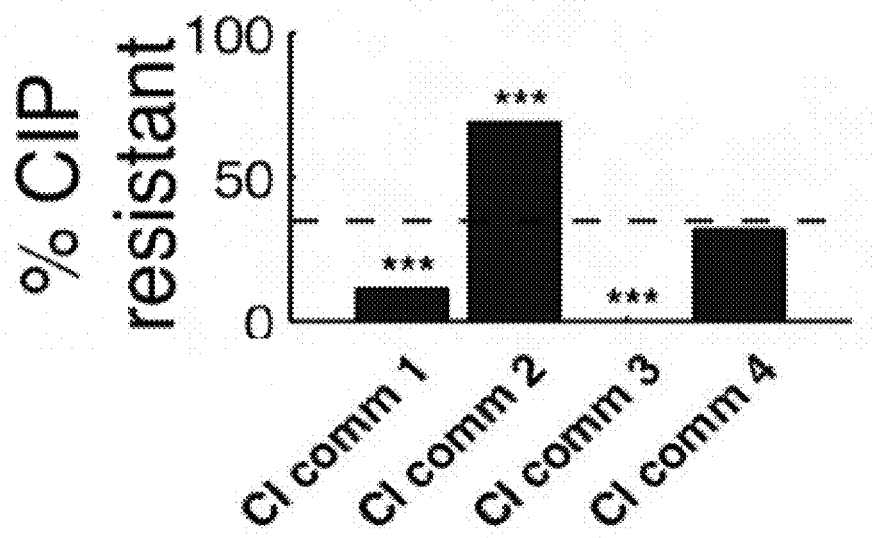
Figure 31H:
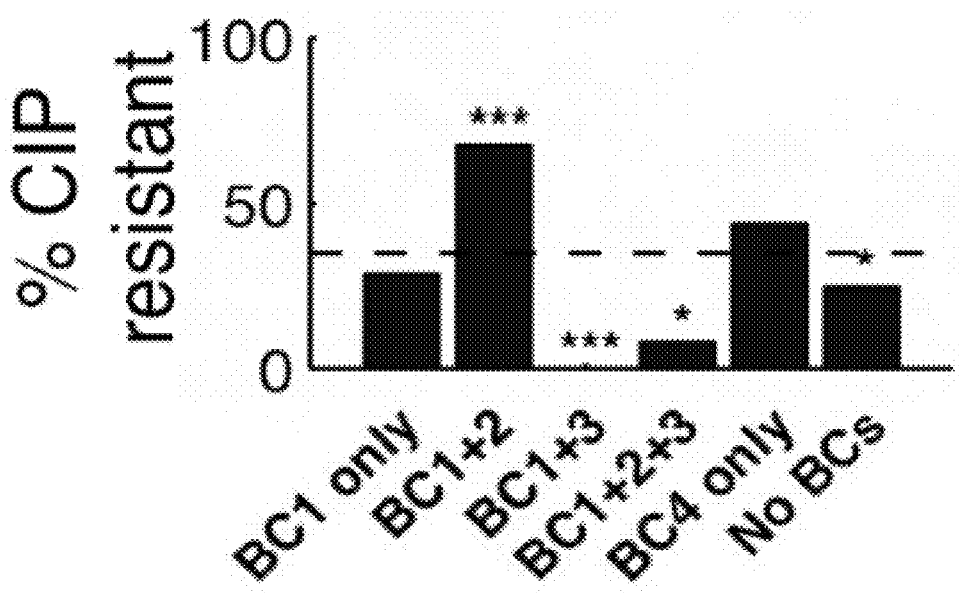
Figure 31I:
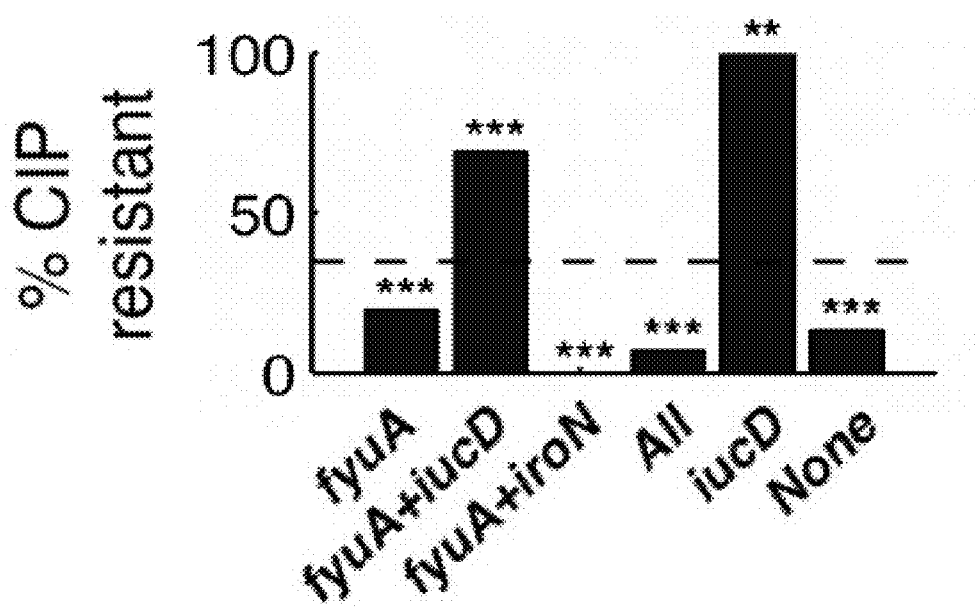
Figure 31J:
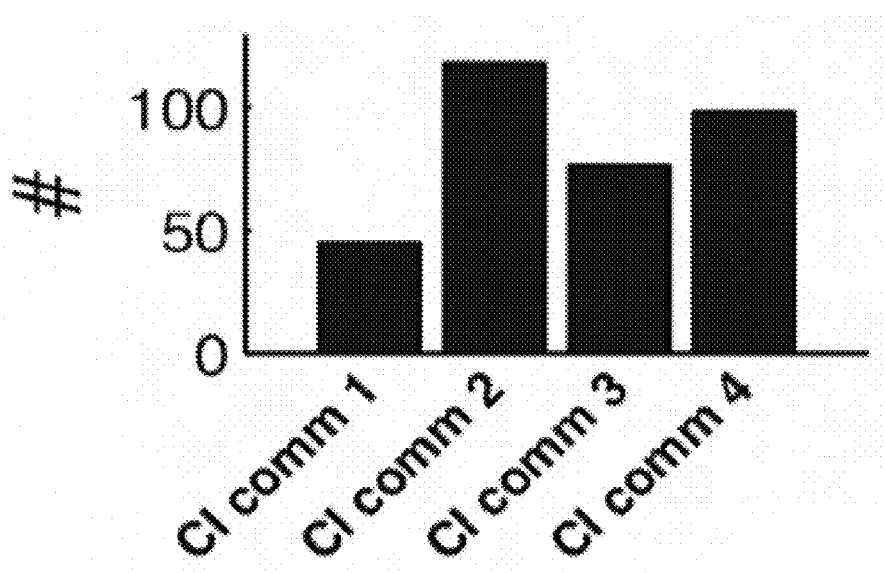
Figure 31K:
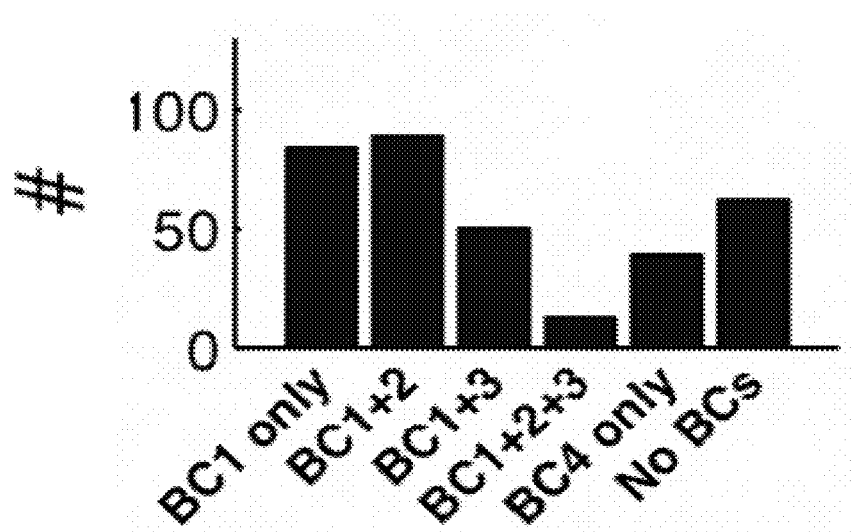
Figure 31L:
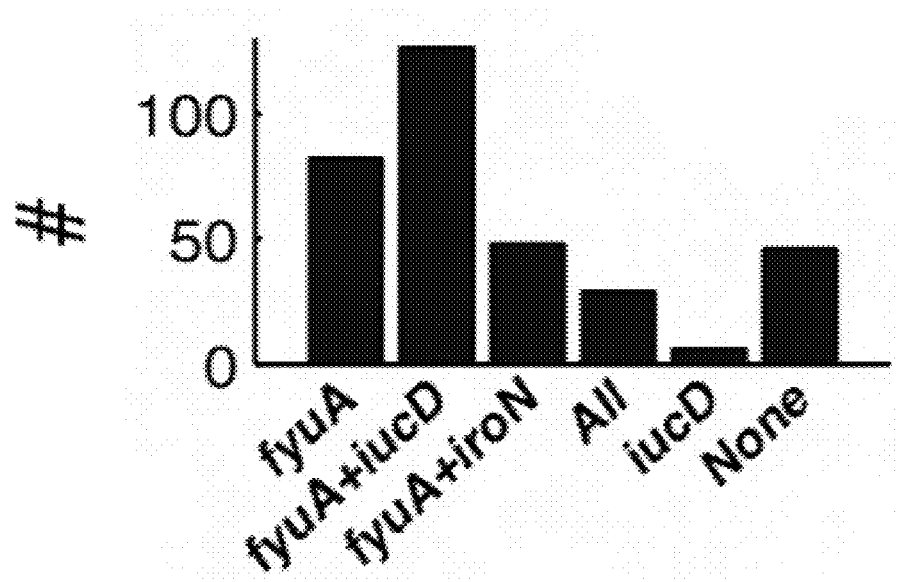

The groups identified by both network community detection and biclustering are defined by VFs encoding specific combinations of siderophores, toxins, and adhesins. Among single functional classes, siderophore genotypes effectively distinguish these communities and biclusters from one another. *E. coli* siderophores exhibit diverse structures and properties and likely represent evolutionary adaptive radiation such that one siderophore system may represent a gain-of-function while another may represent functional redundancy.[14,15] Siderophore systems have also been subject to the most extensive targeted drug development studies in bacteria.[6,16] We therefore examined siderophore genotypes as an independent way to characterize UPEC strategists. Overlaying representative siderophore types on the force-directed layout (FIG. 30C) reveals this non-random siderophore gene distribution. We observed that a specific siderophore genotype characterizes each CI community (CI community 1 is 88.9% fyuA only; CI community 2 is 93.2% fyuA+iucD; community 3 is 51.3% fyuA+iroN; CI community 4 is 46.9% none). Similarly, a dominant siderophore gene marks each BC (BCs 1 and 4 are 61.9% and 34.5% fyuA only, respectively; BC 1+2 is 94.4% fyuA+iucD; BC 3 is 100% iroN). Siderophore genotypes thus identify discrete virulence strategists similarly to the network community detection and bicluster analysis.

Example 26

Virulence Strategists and Patient Sex

To assess the four virulence strategists' clinical significance, we first investigated associations with patient sex, an organizing principle in UTI medical management. The abundant fyuA+iucD strategists (CI community 2, BCs 1+2) are highly associated with male sex (33.1%, 32.6%, and 30.2%, respectively, compared to the 22% male study population, each deviation statistically significant as indicated in FIG. 31). Female sex, classically a UTI-susceptible population, is predominantly associated with fyuA strategists (CI community 1 and BC 4; 8.9% and 10.3% male, respectively). Sex preferences among different virulence strategists reflect the availability of sex-dependent host environments such as the vaginal mucosa, the prostate and its secretions, urethral length, sex differences in immune defenses, hormonal differences, or a combination thereof.

Example 27

Virulence Strategists and Antibiotic Resistance

To determine whether the four virulence strategists are linked with antibiotic resistance, we investigated associations with phenotypic resistance to the two frequently used oral antibiotics trimethoprim-sulfamethoxazole (TMP/S) and ciprofloxacin (CIP) (FIG. 31). The abundant fyuA+iucD strategists (CI community 2 and BC 1+2; 68.6% and 73.2% total siderophore genotypes, respectively) are highly associated with CIP resistance and moderately with TMP/S resistance (FIG. 31). Conversely, the fyuA+iroN siderophore genotype (CI community 3, BC 1+3) is highly susceptible to both CIP and TMP/S. These results indicate that virulence strategies are linked to antibiotic responses. This may reflect selective pressures related to each strategist's preferred niches or a more facile evolutionary route to resistance in fyuA+iucD siderophore genotype. Intriguingly, fluoroquinolone-resistant extended-spectrum β-lactamase (ESBL) strains fit within this fyuA+iucD group and may have emerged from within it.

Example 28

Multivariate Analysis

Since virulence strategists were associated with both patient sex and antibiotic resistance (FIG. 31), we used nested multivariate logistic regression analyses to determine whether virulence strategies and patient sex contribute independently to antibiotic resistance (Table 6). Incremental addition of VF groupings to patient sex in the nested model reveals that VF groupings (CI communities, biclusters, or siderophore genotype) are associated independently with antibiotic resistance. To determine which virulence strategists are associated with resistance we conducted logistic regression analyses with models including each one of the three grouping strategies. In these analyses, male sex and fyuA+iucD siderophore genotype (CI community 2, BC 1+2) independently predict CIP resistance, while TMP/S resistance is associated with the fyuA+iucD siderophore genotype (but not CI community 2 or BC 1+2). Conversely, fyuA+iroN siderophore genotype (CI community 3, BC 1+3) and BC 1, BC 1+2, and BC 1+2+3, but not patient sex, are each predictors of TMP/S susceptibility. Virulence strategies therefore predict antibiotic resistance independently of the sex of the patients from whom they were recovered.

TABLE 6

Patient sex and *E. coli* virulence groups are predictors of ciprofloxacin (CIP) and trimethoprim/sulfa (TMP/S) resistance. In the nested multivariate analyses, lower deviance indicates improved fit to the model. In the logistic regression analyses, odds ratios (OR) of resistance per covariate are shown (with 95% confidence intervals). Only the statistically significant variables from each model are listed for clarity.

| Antibiotic | Nested multivariate analysis model | Deviance | Logistic regression analysis Covariate | OR |
|---|---|---|---|---|
| CIP | Sex | 415*** | Male | 3.5 (2.0-6.0)*** |
|  | Sex + CI communities | 287*** | C2 | 15.0 (6.0-47.0)*** |
|  |  |  | Male | 3.9 (1.9-8.2)*** |
|  |  |  | C4 | 4.0 (1.4-11.0)* |
|  | Sex + biclusters | 322*** | Male | 4.7 (2.4-9.6)*** |
|  |  |  | BC 1 + 2 | 2.1 (1.0-4.7)* |
|  |  |  | BC 1 | 0.4 (0.2-0.9)* |
|  | Sex + siderophore genotype | 294*** | fyuA + iucD | 8.0 (5.0-15.0)*** |
|  |  |  | Male | 4.1 (2.1-8.6)*** |
| TMP/S | Sex | 405 |  |  |
|  | Sex + CI communities | 382*** | C3 | 0.2 (0.1-0.4)*** |
|  | Sex + biclusters | 380*** | BC 1 + 3 | 0.1 (0.0-0.3)*** |
|  |  |  | BC 1 + 2 + 3 | 0.1 (0.0-0.5)* |
|  |  |  | BC 1 | 0.5 (0.2-0.9)* |
|  |  |  | BC 1 + 2 | 0.4 (0.2-0.9)* |
|  | Sex + siderophore genotype | 373*** | fyuA + iucD | 2.0 (1.4-3.7)** |
|  |  |  | fyuA + iroN | 0.1 (0.0-0.5)** |

*$p < 0.05$;
**$p < 0.01$;
***$p < 0.00001$.

Discussion for Example 19-28

Here we use mathematical clustering analyses to identify relationships between microbial virulence strategies, antibiotic resistance, and host sex in clinical *E. coli* infections. Statistically robust linkages between VFs confirm that UPEC deploy these genes in modular combinations consistent with an evolved virulence superstructure. This is also the first report of sex differences in UPEC virulence factor composition, which may reflect pathogenic adaptations to sex-associated host environments. Strong associations between virulence and antibiotic resistance suggest future antivirulence therapies focused on defeating resistant urinary pathogens.

Figure 32A:
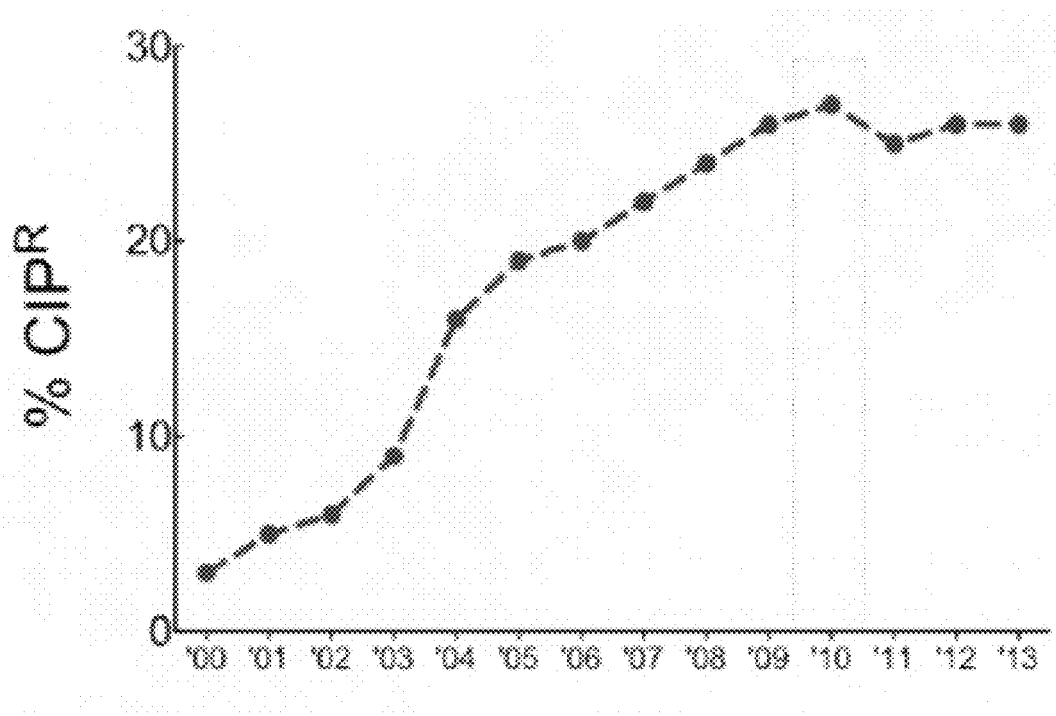
FIG. 32A-C depicts graphs showing siderophore genotypes as correlates of CIP resistance ($CIP^R$).
Figure 32B:
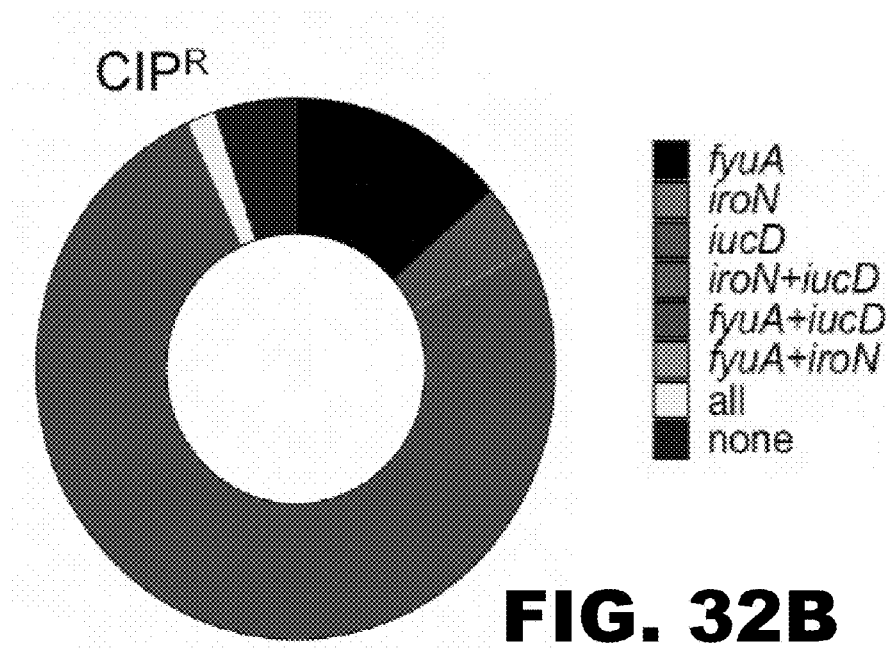
Figure 32C:
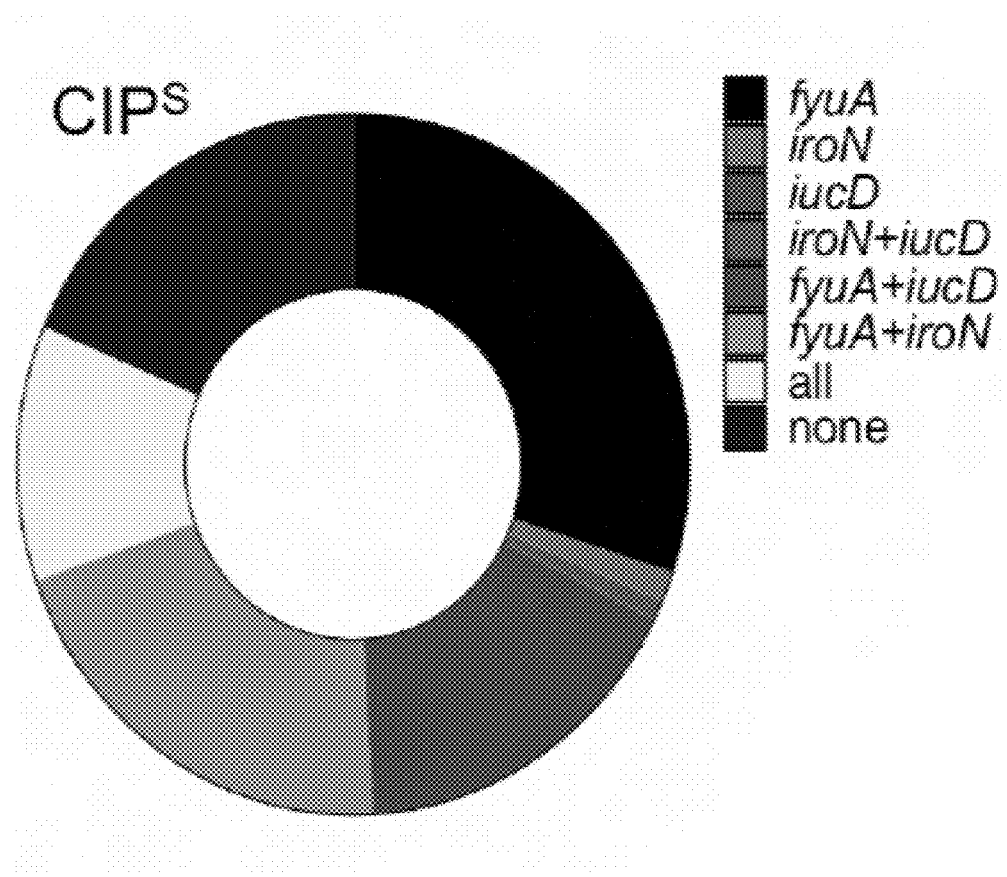

The striking increase in ciprofloxacin resistant ($CIP^R$) isolates over the past 15 years (FIG. 32A) prompts a closer look at the strong association between virulence strategy and $CIP^R$. Virulence strategists are disproportionately distributed among resistant isolates, such that 75% $CIP^R$ isolates possess fyuA+iucD, while none are the fyuA+iroN siderophore genotype (FIG. 32B,C). These data suggest that *E. coli* fluoroquinolone (FQ) resistance is preferentially evolving within strains with the fyuA+iucD siderophore genotype. This association is further supported by retrospective identification of aerobactin genes (iucD, iutA) in previously reported FQ-resistant *E. coli* strains ST131, ST1193, and 015:K52:H1.[17-19] This virulence-resistance association's origin is unclear but may have arisen from clinical practices favoring FQ treatment of males (shown here to be disproportionately infected with the fyuA+iucD siderophore genotype) or possibly from FQ-associated fitness gains in Gram-negative bacteria.

The strong positive and negative associations between virulence strategy and antibiotic resistance identify high priority antivirulence therapeutic targets. A successful virulence-targeting therapeutic strategy may target multiple evolutionarily co-associated VFs such as those described here. Natural examples of such targeted agents include pesticin and its derivatives that selectively kill fyuA-expressing *E. coli*, and albomycin, which delivers a toxin through N-hydroxamate importers similar to those that import aerobactin.[20,21] Siderophore biosynthesis inhibitors, "Trojan horse" siderophore conjugates, or adhesin inhibitors might be further developed to target specific strategists.[22-24] A rapid diagnostic that differentiates between virulence strategists could guide antivirulence therapeutic selection by physicians. Such a diagnostic would be especially valuable for TMP/S and FQ resistant clinical isolates, which lack simple genetic markers analogous to mecA or vanA.

The stereotypical VF distributions observed here suggest that UPEC virulence evolves by acquiring synergistic VF combinations. In this paradigm, virulence depends on the manner in which specific VFs are combined rather than the sum total of virulence factors present. These virulence strategist groups contain both B2 and non-B2 strains, indicative of an organizational level distinct from phylogenetic type. These distinctive VF combinations may reflect general adaptations to a subset of niches within a host or specialized adaptations to sex-specific host niches. VFs associated with iucD may be better adapted to prostate tissue while VFs associated with fyuA may represent adaptations to infection microenvironments common to all hosts. The relatively rare coexistence of iucD and iroN-associated VFs may reflect a degree of functional redundancy in which metabolic costs override the advantages of extra VFs.

The VF network identified here thus provides a framework for the design of future combinatorial antivirulence therapies that target specific patient populations. New agents intended to defeat antibiotic resistance should be tested in model UPEC strains exhibiting resistance-associated virulence strategies. Although the VFs assessed here are likely an incomplete list, we expect that genome sequencing guided by these results will help identify additional strategy-specific VFs in an otherwise genetically diverse population. The epidemiologic and mathematical approach illustrated in this study should help construct future combinatorial antivirulence therapeutic strategies against antibiotic resistant pathogens.

Methods for Examples 19-28

Study Design, Data Collection, Laboratory Analyses, and Definitions

The samples were collected as part of a Washington University Institutional Review Board-approved prospective study of patients with *E. coli* bacteriuria (>$5 \times 10^4$ colony forming units per milliliter) described by Marschall et al.[11] Strains without associated blood culture data were not excluded from this study. Briefly, clinical isolates were collected from male and female patients with significant bacteriuria. Bacterial DNA was extracted using a QIAamp DNA mini kit (Qiagen, Valencia, Calif.). DNA probes for virulence genes were conducted as previously described[11], and the presence of these genes was determined by dot-blot hybridization using a microarray system as described elsewhere (Table 1). *E. coli* phylogenetic group was determined from hybridization results using the triple genotyping method of Clermont et al.[25] Antimicrobial susceptibility was determined using disk diffusion tests. Bacteriuria was defined as? $5 \times 10^4$ colony forming units (CFU)/mL in non-catheterized patients and $\geq 5 \times 10^3$ CFU/mL in catheterized patients, as well as by using the patients' documented urinary symptoms. Pyelonephritis was defined as the presence of flank pain and tenderness and/or fever; sepsis and sepsis-induced hypotension were defined using established clinical criteria. The Microbiology Laboratory at Barnes Jewish Hospital provided clinical antibiogram data.

Network Analysis:

The (bipartite) clinical-isolates-by-genes binary data array was projected onto two separate (unipartite) network representations, one each for the clinical isolates and for the VFs. The VF network—connected by similar co-occurrences across the clinical isolate population—was defined by statistically significant positive correlation coefficients between VF pairs. Statistical significance was determined by Fisher exact tests on 2×2 contingency tables; for each pair of genes the 2×2 contingency table of the number of expressed and not-expressed outcomes for each of these two genes was tabulated, and then a Fisher exact test was used to determine whether or not the two genes appeared independently within the population of clinical isolates, conditional on their observed marginal frequencies in the population. A 1.5% p-value threshold (one-tailed on the right, without correction for multiple testing) was chosen to ensure that the resulting network of VFs was a single connected component. An edge was defined as present between any pair of positively correlated genes that satisfied the threshold, and then the positive weight of that edge was set by the correlation coefficient. In order to continue to respect the diversity of background VF expression frequencies, we define the network of clinical isolates in terms of the column-standardized version of the clinical-isolates-by-VFs data array—that is, each column is centered to zero and rescaled to unit variance. The resulting column-standardized matrix M yielded the full matrix of correlation coefficients between VFs through the expression $M^T M/(n-1)$, where n is the number of clinical isolates. For symmetry, we defined the clinical isolates adjacency matrix—whose (i,j) element indicates the presence and weight of the edge connecting nodes i and j—from the matrix product $MM^T$, thresholding the elements to retain all positive elements of the resulting matrix product. We set the diagonals of both adjacency matrices to zero (no self-loops).

Community detection of the clinical isolate and VF networks was performed by maximizing modularity with a resolution parameter, by a generalized implementation of the Louvain method followed by Kernighan-Lin node-swapping steps.[9,10,26,27] By varying the resolution parameter, graphs were partitioned into various numbers of communities, and robust regions of the resolution parameter space with common results were sought. Through this procedure, a collection of nested VF network partitions was identified (as visualized in the main text). For the network of clinical isolates, closely similar 4-community partitions were identified in a range of resolution parameters straddling the default unit value, so we restricted our attention to a 4-community partition found at that default resolution.

Biclustering:

Biclustering is a popular statistical tool for exploratory analysis of high dimensional data.[28] Given a matrix of genes by isolates, the goal of biclustering is to group the rows and columns to find 'dense' regions of the matrix, i.e., groups of VFs similarly expressed by subsets of isolates. The expression profile is a binary structure where values for each clinical isolate indicate expression of a VF ('0'=absence, '1'=presence). A binary version of LAS (large average submatrices) was used to exhaustively search the 337×16 condition matrix for all statistically significant biclusters of large average expression.[13] The method operates in an iterative-residual fashion, and is driven by a Bonferroni-based significance score that trades off between submatrix size and average value. The method identified statistically significant large average biclusters, in the sense that the VFs are expressed across the collection of clinical isolates more often than expected within the entire population. The significance of an identified k×1 bicluster U is measure through a binary score function $$S(U) = -\log\left[\binom{m}{k}\binom{n}{\ell}F(k\ell - \tau; k\ell, 1-p)\right]$$

where $F(\tau; kl; 1-p)$ gives the null probability that the kl entries of U have $\tau$ or more 1s. The probability inside the logarithm is a Bonferroni-corrected p-value associated with observing a submatrix with an average at least as large as U. The algorithm was set to find biclusters with score greater than or equal to 100.

Nested Model/Logistic Regression:

A multivariate logistic regression model was used to identify covariates significantly associated with antibiotic resistance. The fitted model included indicator (0/1) covariates for sex, community containment, bicluster containment, and siderophore content. The covariates with statistically significant coefficients (p-value<0.10) for each antibiotic (CIP and TMP/S) are shown in Table 5. A nested models approach was used to determine the significance of variability in antibiotic resistance (CIP and TMP/S) explained by the inclusion of covariates describing sex, community containment, bicluster containment, and siderophore type. The null model contained only the mean response for resistance to CIP and TMP/S, respectively. Sequentially, each of the above covariates was added to the null model and the variability explained in the model was recorded. To test the significance of the added covariate type, an analysis of deviance was employed wherein a $\chi^2$ test was used to test the reduction in deviance from the null model. The models and test results are shown in Table 4.

REFERENCES FOR EXAMPLES 19-28

1. Litwin M S, Saigal C S, Yano E M, et al. Urologic diseases in America Project: analytical methods and principal findings. *The Journal of urology* 2005; 173(3): 933-7.
2. Ronald A R, Nicolle L E, Stamm E, et al. Urinary tract infection in adults: research priorities and strategies. *International journal of antimicrobial agents* 2001; 17(4): 343-8.
3. Cai T, Mazzoli S, Mondaini N, et al. The role of asymptomatic bacteriuria in young women with recurrent urinary tract infections: to treat or not to treat? *Clinical infectious diseases: an official publication of the Infectious Diseases Society of America* 2012; 55(6): 771-7.
4. Fischbach M A, Walsh C T. Antibiotics for emerging pathogens. *Science* 2009; 325(5944): 108993.

5. Wiles T J, Kulesus R R, Mulvey M A. Origins and virulence mechanisms of uropathogenic *Escherichia coli*. *Experimental and molecular pathology* 2008; 85(1): 11-9.
6. Brumbaugh A R, Mobley H L. Preventing urinary tract infection: progress toward an effective *Escherichia coli* vaccine. *Expert review of vaccines* 2012; 11(6): 663-76.
7. Clatworthy A E, Pierson E, Hung D T. Targeting virulence: a new paradigm for antimicrobial therapy. *Nature chemical biology* 2007; 3(9): 541-8.
8. Silverman J A, Schreiber H Lt, Hooton T M, Hultgren S J. From physiology to pharmacy: developments in the pathogenesis and treatment of recurrent urinary tract infections. *Current urology reports* 2013; 14(5): 448-56.
9. Fortunato S. Community detection in graphs. *Physics Reports* 2010; 486(3-5): 75-174.
10. Porter M A, Onnela J P, Mucha P J. Communities in Networks. *Notices of the AMS* 2009; 56(9): 1082-97 & 164-66.
11. Marschall J, Zhang L, Foxman B, Warren D K, Henderson J P, Program CDCPE. Both host and pathogen factors predispose to *Escherichia coli* urinary-source bacteremia in hospitalized patients. *Clinical infectious diseases: an official publication of the Infectious Diseases Society of America* 2012; 54(12): 1692-8.
12. Johnson J R, Kuskowski M A, Gajewski A, et al. Extended virulence genotypes and phylogenetic background of *Escherichia coli* isolates from patients with cystitis, pyelonephritis, or prostatitis. *The Journal of infectious diseases* 2005; 191(1): 46-50.
13. Shabalin A A, Weigman V J, Perou C M, Nobel A B. Finding large average submatrices in high dimensional data. *The Annals of Applied Statistics* 2009; 3(3): 985-1012.
14. Chaturvedi K S, Hung C S, Crowley J R, Stapleton A E, Henderson J P. The siderophore yersiniabactin binds copper to protect pathogens during infection. *Nature chemical biology* 2012; 8(8): 731-6.
15. Henderson J P, Crowley J R, Pinkner J S, et al. Quantitative metabolomics reveals an epigenetic blueprint for iron acquisition in uropathogenic *Escherichia coli*. *PLoS pathogens* 2009; 5(2): e1000305.
16. Gorska A, Sloderbach A, Marszall M P. Siderophore-drug complexes: potential medicinal applications of the 'Trojan horse' strategy. *Trends in pharmacological sciences* 2014; 35(9): 442-9.
17. Olesen B, Frimodt-Moller J, Leihof R F, et al. Temporal trends in antimicrobial resistance and virulence-associated traits within the *escherichia coli* sequence type 131 clonal group and its H30 and H30-Rx subclones, 1968 to 2012. *Antimicrobial agents and chemotherapy* 2014; 58(11): 6886-95.
18. Olesen B, Scheutz F, Menard M, et al. Three-decade epidemiological analysis of *Escherichia coli* 015:K52:H1. *Journal of clinical microbiology* 2009; 47(6): 1857-62.
19. Platell J L, Trott D J, Johnson J R, et al. Prominence of an 075 clonal group (clonal complex 14) among non-ST131 fluoroquinolone-resistant *Escherichia coli* causing extraintestinal infections in humans and dogs in Australia. *Antimicrobial agents and chemotherapy* 2012; 56(7): 3898-904.
20. Lukacik P, Barnard T J, Keller P W, et al. Structural engineering of a phage lysin that targets gram-negative pathogens. *Proceedings of the National Academy of Sciences of the United States of America* 2012; 109(25): 9857-62.
21. Pramanik A, Stroeher U H, Krejci J, et al. Albomycin is an effective antibiotic, as exemplified with *Yersinia enterocolitica* and *Streptococcus pneumoniae*. *International journal of medical microbiology: IJMM* 2007; 297(6): 459-69.
22. Cusumano C K, Pinkner J S, Han Z, et al. Treatment and prevention of urinary tract infection with orally active FimH inhibitors. *Science translational medicine* 2011; 3(109): 109ra15.
23. Engelhart C A, Aldrich C C. Synthesis of chromone, quinolone, and benzoxazinone sulfonamide nucleosides as conformationally constrained inhibitors of adenylating enzymes required for siderophore biosynthesis. *The Journal of organic chemistry* 2013; 78(15): 7470-81.
24. Zheng T, Nolan E M. Enterobactin-mediated delivery of beta-lactam antibiotics enhances antibacterial activity against pathogenic *Escherichia coli*. *Journal of the American Chemical Society* 2014; 136(27): 9677-91.
25. Clermont O, Bonacorsi S, Bingen E. Rapid and simple determination of the *Escherichia coli* phylogenetic group. *Applied and environmental microbiology* 2000; 66(10): 4555-8.
26. Jutla I S, Lucas G S, Mucha P J. A generalized louvain method for community detection implemented in MATLAB (http://netwiki.amath.unc.edu/GenLouvain). 2011.
27. Reichardt J, Bornholdt S. Statistical mechanics of community detection. *Phys Rev E* 2006; 74(1).
28. Madeira S C, Oliveira A L. Biclustering algorithms for biological data analysis: a survey. *IEEE/ACM Transactions on Computational Biology and Bioinformatics* 2004; 1: 24-45

What is claimed is:

1. A method for detecting the presence of yersiniabactin-expressing bacteria in a subject, the method comprising the steps of:
 a) obtaining a sample from the subject;
 b) analyzing the sample, in vitro, by mass spectrometry for the presence or absence of hydroxyphenyl-thiazolinyl-thiazolinyl (HPTT), wherein the detection of a peak with m/z 307 detects HPTT; and
 c) identifying the presence of yersiniabactin-expressing bacteria in the subject when HPTT is present in the sample.

2. The method of claim 1, wherein the sample is a urine sample.

3. The method of claim 1, wherein the yersiniabactin-expressing bacteria is uropathogenic bacteria.

4. The method of claim 1, wherein the yersiniabactin-expressing bacteria is uropathogenic *Escherichia coli*.

5. The method of claim 1, wherein the sample is analyzed in conjunction with liquid chromatography.

6. The method of claim 1, wherein the subject has recurrent urinary tract infections.

* * * * *